(12) United States Patent
Paik et al.

(10) Patent No.: US 11,894,114 B2
(45) Date of Patent: Feb. 6, 2024

(54) COMPLEX IMAGE DATA ANALYSIS USING ARTIFICIAL INTELLIGENCE AND MACHINE LEARNING ALGORITHMS

(71) Applicant: Sirona Medical, Inc., San Francisco, CA (US)

(72) Inventors: David Seungwon Paik, Half Moon Bay, CA (US); Vernon Marshall, San Francisco, CA (US); Mark D. Longo, San Francisco, CA (US); Cameron Andrews, San Francisco, CA (US); Kojo Worai Osei, San Francisco, CA (US); Berk Norman, San Francisco, CA (US); Ankit Goyal, San Francisco, CA (US)

(73) Assignee: Sirona Medical, Inc., San Francisco, CA (US)

( * ) Notice: Subject to any disclaimer, the term of this patent is extended or adjusted under 35 U.S.C. 154(b) by 392 days.

(21) Appl. No.: 17/143,808

(22) Filed: Jan. 7, 2021

(65) Prior Publication Data
US 2021/0216822 A1    Jul. 15, 2021

Related U.S. Application Data

(63) Continuation of application No. PCT/US2020/053840, filed on Oct. 1, 2020.
(Continued)

(51) Int. Cl.
*G06N 3/08* (2023.01)
*G16H 15/00* (2018.01)
(Continued)

(52) U.S. Cl.
CPC ............. *G16H 15/00* (2018.01); *G06F 3/013* (2013.01); *G06F 3/167* (2013.01);
(Continued)

(58) Field of Classification Search
CPC ........ G16H 15/00; G16H 30/40; G06F 3/013; G06F 3/167; G06F 18/2148; G06F 18/22;
(Continued)

(56) References Cited

U.S. PATENT DOCUMENTS 10,248,759 B2 * 4/2019 Larcom ................. G16H 50/70
2009/0028403 A1   1/2009 Bar-Aviv et al.
(Continued)

FOREIGN PATENT DOCUMENTS

WO   WO-2018093865 A1   5/2018
WO   WO-2018222755 A1   12/2018
(Continued)

OTHER PUBLICATIONS

Canny, Collision detection for moving polyhedra. IEEE Trans Pattern Anal Mach Intell.8(2):200-209 (1986).
Chen et al., DeepLab: Semantic Image Segmentation with Deep Convolutional Nets, Atrous Convolution, and Fully Connected CRFs. IEEE Trans Pattern Anal Mach Intell 40(4):834-848 (2018).
(Continued)

*Primary Examiner* — Charlotte M Baker
(74) *Attorney, Agent, or Firm* — Wilson Sonsini Goodrich & Rosati

(57) ABSTRACT

Disclosed herein are systems, methods, and software for providing a platform for complex image data analysis using artificial intelligence and/or machine learning algorithms. One or more subsystems allow for the capturing of user input such as eye gaze and dictation for automated generation of findings. Additional features include quality metric tracking and feedback, and worklist management system and communications queueing.

19 Claims, 29 Drawing Sheets

Related U.S. Application Data

(60) Provisional application No. 62/909,027, filed on Oct. 1, 2019.

(51) Int. Cl.

| | | |
|---|---|---|
| *G06T 7/11* | (2017.01) | |
| *G06F 3/01* | (2006.01) | |
| *G06F 3/16* | (2006.01) | |
| *G06N 3/04* | (2023.01) | |
| *G10L 15/22* | (2006.01) | |
| *G06V 10/94* | (2022.01) | |
| *G06F 18/214* | (2023.01) | |
| *G06F 18/22* | (2023.01) | |
| *G06F 18/40* | (2023.01) | |

(52) U.S. Cl.
CPC .......... *G06F 18/2148* (2023.01); *G06F 18/22* (2023.01); *G06F 18/41* (2023.01); *G06N 3/04* (2013.01); *G06N 3/08* (2013.01); *G06T 7/11* (2017.01); *G06V 10/95* (2022.01); *G10L 15/22* (2013.01); *G06T 2200/24* (2013.01); *G06T 2207/30041* (2013.01); *G06V 2201/03* (2022.01)

(58) Field of Classification Search
CPC ............ G06F 18/41; G06N 3/04; G06N 3/08; G06T 7/11; G06T 2200/24; G06T 2207/30041; G06T 2207/10056; G06T 2207/10068; G06T 2207/10072; G06T 2207/10116; G06T 2207/10132; G06T 2207/30004; G06T 7/0012; G06V 10/95; G06V 2201/03; G10L 15/22
USPC ........................................................ 382/128
See application file for complete search history.

(56) References Cited

U.S. PATENT DOCUMENTS

| | | |
|---|---|---|
| 2013/0151286 A1 | 6/2013 | Kablotsky et al. |
| 2013/0251233 A1 | 9/2013 | Yang et al. |
| 2016/0253314 A1 | 9/2016 | Pottier et al. |
| 2016/0350919 A1 | 12/2016 | Steigauf et al. |
| 2016/0364862 A1 | 12/2016 | Reicher et al. |
| 2017/0358241 A1 | 12/2017 | Wexler et al. |
| 2018/0039761 A1 | 2/2018 | Gaskin et al. |
| 2018/0055468 A1 | 3/2018 | Reicher |
| 2018/0342055 A1 | 11/2018 | Lyman et al. |
| 2021/0097644 A1 | 4/2021 | Sommerlade et al. |
| 2021/0169417 A1 | 6/2021 | Burton |

FOREIGN PATENT DOCUMENTS

| | | |
|---|---|---|
| WO | WO-2021067624 A1 | 4/2021 |
| WO | WO-2022212771 A2 | 10/2022 |

OTHER PUBLICATIONS

Durand et al., MR imaging features of common variant spinal anatomy. Magn Reson Imaging Clin N Am 18(4):717-726 (2010).
Long et al., Fully Convolutional Networks for Semantic Segmentation. arXiv (2015). 10 pages.
Ringler et al., Syntactic and semantic errors in radiology reports associated with speech recognition software. Health Informatics Journal 23(1): 3-13 (2017).
Sistrom, Conceptual Approach for the Design of Radiology Reporting Interfaces: The Talking Template. J Digit Imaging 18(3): 176-187 (2005).
Szegedy et al., Going Deeper with Convolutions. arXiv. 12 pages (2014).
Wei et al., Convolutional Pose Machines. arXiv 9 pages (2016).
PCT/US2020/053840 International Preliminary Report on Patentability dated Apr. 14, 2022.
PCT/US2020/053840 International Search Report and Written Opinion dated Mar. 12, 2021.

* cited by examiner

FIG. 10
Clinical Workflow
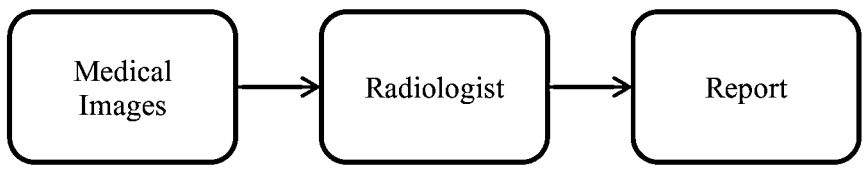
Current Peer Review
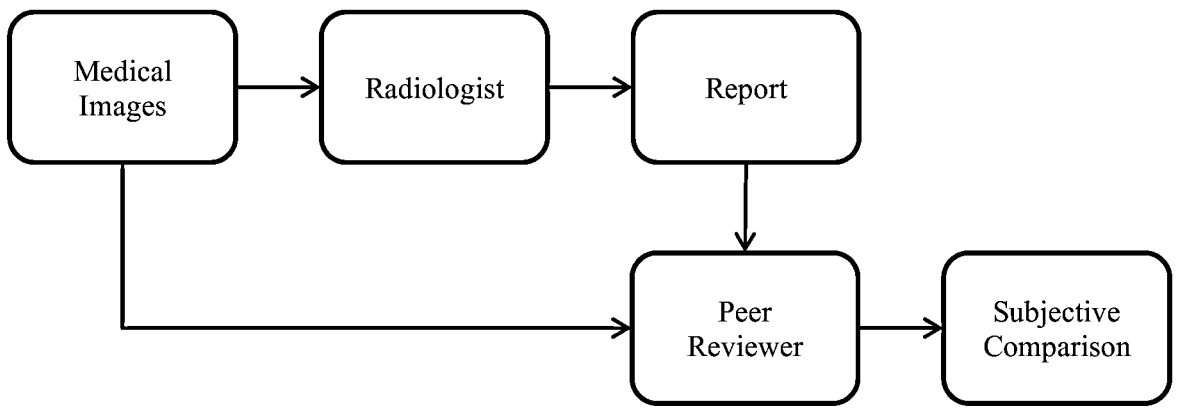

NLP pipeline 1: Label Extraction

NLP pipeline 2: Report Generation

$$\nabla I \cong (\nabla G) * I$$

$$g(x) = \frac{1}{1+|\nabla I|} \quad or \quad g(x) = e^{-|\nabla I|}$$

$$D = \sum_{i=1}^{N} d_i^2$$

COMPLEX IMAGE DATA ANALYSIS USING ARTIFICIAL INTELLIGENCE AND MACHINE LEARNING ALGORITHMS

CROSS-REFERENCE

This application is a continuation of International Patent Application No. PCT/US2020/053840, filed on Oct. 1, 2020, which claims the benefit of the U.S. Provisional Patent Application No. 62/909,027, filed on Oct. 1, 2019, the entire disclosure of which is incorporated herein by reference.

BACKGROUND

Improvements in medical imaging technology has allowed for faster and more accurate diagnoses without resorting to invasive procedures. The wide array of available imaging techniques such as X-ray, ultrasound, magnetic resonance imaging (MRI) and computed tomography (CT) provide enhanced diagnosis of various possible ailments. However, despite improvements in imaging technology, the interpretation of medical images is a predominantly manual process with limits on speed and efficiency because of the reliance on a human to interpret the image and laboriously enter findings into the medical report.

SUMMARY

Described herein are systems, software, and methods for interpreting medical images and generating reports. In some aspects, the systems, software, and methods described herein represent a single interface to the various subsystems of the radiology technology stack (e.g., RIS, PACS, AI, reporting, etc.). The system can provide a unified experience to a user such as a radiologist and provide support and analytics that would otherwise not be possible under a fragmented tech stack. In some cases, the system includes a plurality of subsystems such as those described herein.

Medical image interpretation is a process in which the clinician receives as inputs, the set of medical images and associated clinical information (e.g., medical history, indication for imaging), and produces a textual report that includes findings (a list of all notable observations) and impressions (e.g., a ranked-order summary of the clinically important findings for the referring physician to be aware of). Existing radiology technology stacks share various deficiencies. First, the technology stack is highly fragmented, often relying upon disparate applications with very limited communication between applications. Second, in part due to the lack of integration between the PACS image viewer and the reporting software, these applications are displayed on different monitors on a multi-head computer display setup requiring the user to divert their gaze away from the image being interpreted. This has been dubbed the "look away problem" (Sistrom C L, J Dig Imag 2005). While speech-to-text dictation of reports is intended to solve this problem, in practice it falls far short since users either continue to look away or make clerical errors by dictating into the wrong template fields without looking (Ringler M D, et al., Health Informatics Journal 2017). Even where the user uses the "next field" and "previous field" buttons or verbal commands on the dictaphone, errors can still occur. Without visual feedback, the text is often placed into the incorrect section of the report template.

Disclosed herein are computer-assistance algorithms used to assist human readers in the task of image interpretation, which can incorporate one or more of artificial intelligence (AI), deep learning (DL), machine learning (ML), computer-aided detection/diagnosis (CADe/CADx), and other algorithms. Disclosed herein are systems, software, and methods for presenting the AI output to a clinician and to aid in producing a report. In some aspects, the system is also used to generate analytics for the purposes of business management, quality assurance, and self-improvement.

Disclosed herein are systems, software, and methods for providing AI-assisted image segmentation and/or labeling, including the labeling of anatomic variants. For example, a medical image such as an X-ray can be automatically segmented and labeled for vertebra with the ability to handle anatomic variants of spinal anatomy. While normal anatomic features can be detectable by an algorithm, the presence of anatomic variants may lead to incorrect labeling, for example, an anomalous number of vertebrae or the presence of transitional vertebrae in a subject. Accordingly, accounting for anatomic variants enables more accurate labeling, which is important for successfully shifting the workload of medical image interpretation from the clinician onto the computing system and for accurate reporting to the referring physician. Image analysis algorithm(s) can be utilized to perform the segmentation and/or labeling.

Within the field of medical imaging, a medical imaging scanner (e.g., MRI) produces a set of one or more images for review by clinicians. There can be a number of functionalities that are provided by one or more information subsystems. The RIS (Radiology Information System) handles various non-image information and functions such as order entry, pre-authorization, patient demographic and insurance information, scheduling, resource management, examination performance tracking, reporting distribution, billing and reimbursement, etc. Often, the RIS system handles the worklist of patients whose studies are awaiting interpretation. Image archival and viewing is often referred to as PACS (Picture Archiving and Communications System) where the clinician is able to scroll through stacks of images that correspond to a specific patient study. Some PACS systems offer some integration of software assistance. In some instances, software assistance is offered through a specialized stand-alone workstation. Reporting can be performed through human or computerized speech-to-text transcription with keyboard-based editing. The reporting system is often a stand-alone system.

In some aspects, AI systems triage exams, prioritizing interpretation if an urgent finding such as an intracranial hemorrhage is detected. Other AI algorithms that detect possible findings of interest present the reader with annotations on the image where suspicious regions are found. AI algorithms that are designed to segment specific anatomic regions present the segmented region to the user and may provide additional quantitative metrics based on that region.

One or more of the algorithms, programs, and functions utilized in the systems, software, and methods disclosed herein can be integrated into a single technology stack with a unified user interface allowing for efficient communication and seamless transitioning from one functionality to another. For example, a medical image may be evaluated using artificial intelligence to detect one or more segmented features in the image, which are analyzed to generate a textual description of a finding that a user may be prompted to accept. The accepted finding can be automatically incorporated into a medical report, and the user or subsequent consumers of the report may browse the report with the selected finding text linked back to the location of the finding in the image. These different modules or functionalities can be integrated through a single unified user interface instead of distinct user interfaces and/or applications or programs. Accordingly, the present disclosure provides tools for a complete radiology workflow that can include multi-modality image review functionality, patient worklist, and dictation and transcription services. Accordingly, the present disclosure addresses the various deficiencies in the existing radiology technology stack. As an illustrative example, disclosed herein is a computer based system or platform, comprising: (a) a processor; (b) a display configured to show a graphical user interface for displaying a medical image; (c) a non-transitory computer readable storage medium encoded with instructions that, when executed by the processor, cause the processor to provide: (i) a module for AI-assisted image segmentation and labeling; (ii) a module for AI-assisted dictation of findings and/or measurements, comparison, and query; (iii) a module for bi-directional dynamic linking of findings, (iv) a module for AI finding display and interaction, (v) a module for tracking and analyzing AI assistance, (vi) a module providing a communications hub for users, (vii) a module providing worklist management, (viii) a module for AI-enabled quality metrics, (ix) a module for AI-assisted self-improvement, and (x) a module for hanging protocols. The overall system or platform can be configured for medical report generation with one or more of the individual modules or subsystems configured to carry out specific processes that effectuate and/or are related to report generation. Each of these modules (which can also be referred to as systems or subsystems of the overall system or platform) can be configured to operate together, for example, in a single technology stack.

Disclosed herein is a computer based system for medical report generation, comprising: (a) a processor; (b) a display configured to show a graphical user interface for evaluating a medical image; (c) a non-transitory computer readable storage medium encoded with a computer program that causes said processor to: (i) generate a medical report including a computer-generated finding related to said medical image when a user accepts inclusion of said computer-generated finding within said report. In some embodiments, the system comprises an image analysis algorithm configured to generate said computer-generated finding, wherein said image analysis algorithm comprises an image segmentation algorithm for partitioning said medical image into multiple pixel segments corresponding to a plurality of image features. In some embodiments, said image analysis algorithm comprises an annotation algorithm that annotates at least one image feature of said plurality of image features. In some embodiments, said plurality of image features are organized in a hierarchy. In some embodiments, each of said plurality of features corresponds to an anatomical structure, a tissue type, a tumor or tissue abnormality, a contrast agent, or any combination thereof. In some embodiments, said plurality of features comprises one or more of nerve, blood vessel, lymphatic vessel, organ, joint, bone, muscle, cartilage, lymph, blood, adipose, ligament, or tendon. In some embodiments, said medical report comprises one or more sentences or phrases describing or assessing said at least one feature. In some embodiments, said system further comprises an audio detection component configured to detect or record an input that indicates when said user accepts inclusion of said computer-generated finding. In some embodiments, said medical image is a radiographic image, a magnetic resonance imaging (MRI) image, an ultrasound image, an endoscopy image, an elastography image, a thermogram image, a positron emission tomography (PET) image, a single photon emission computed tomography (SPECT) image, an optical coherence tomography (OCT) image, a computed tomography (CT) image, a microscopy image, or a medical photography image. In some embodiments, said user is a healthcare provider. In some embodiments, said healthcare provider is a radiologist, a radiologic technician or assistant, a surgeon, a family doctor, an internal medicine physician, a pediatrician, an obstetrician/gynecologist, a dermatologist, an infectious disease physician, a nephrologist, an ophthalmologist, a pulmonologist, a neurologist, an anesthesiologist, an oncologist, a nurse, or a physical therapist. In some embodiments, said computer program is further configured to cause said processor to analyze said image using a machine learning classifier algorithm, thereby generating a result comprising said computer-generated finding. In some embodiments, said computer-generated finding comprises an identification or evaluation of a pathology. In some embodiments, said identification or evaluation of said pathology comprises at least one of a severity, quantity (e.g., number of lung nodules), measurement (e.g., length, area, and/or volume of a lung nodule), presence, or absence of said pathology or a sign or symptom thereof. In some embodiments, said computer-generated finding is included in said medical report when said finding comprises a positive identification or description of said pathology. In some embodiments, said system uses a cloud-based server or network to perform at least one of analysis of said medical image and generation of said report. In some embodiments, said processor is configured to provide a worklist management interface allowing said user to reserve one or more cases comprising one or more images from a plurality of cases available for review by a group of users. In some embodiments, said processor is configured to determine congruence between said computer-generated finding and a user-finding included in said report. In some embodiments, said processor is configured to automatically populate a portion of said medical report based on a determination of congruence between said feature and said input. In some cases, said processor is configured to present said computer-generated finding to said user for acceptance and optionally editing, wherein an accepted computer-generated finding is automatically populated into said portion of said report. In some cases, said processor is configured to perform a quality metric assessment of said report. In some cases, said quality metric assessment comprises using natural language processing of said report to generate a list of one or more findings and analyzing said list of one or more findings to generate one or more quality metrics. In some cases, said processor is configured to collect analytics on user interaction with said system and provide feedback for improving efficiency or quality.

Disclosed herein is a computer-implemented method for medical report generation, comprising: (a) displaying a medical image; (b) generating a medical report including a computer-generated finding related to said medical image when a user accepts inclusion of said computer-generated finding within said report. In some embodiments, the method uses an image analysis algorithm configured to generate said computer generated finding, wherein said image analysis algorithm comprises an image segmentation algorithm for partitioning said medical image into multiple pixel segments corresponding to a plurality of image features. In some embodiments, said image analysis algorithm comprises an annotation algorithm that annotates at least one image feature of said plurality of image features. In some embodiments, said plurality of image features are organized in a hierarchy. In some embodiments, each of said plurality of features corresponds to an anatomical structure, a tissue type, a tumor or tissue abnormality, a contrast agent, or any combination thereof. In some embodiments, said plurality of features comprises one or more of nerve, blood vessel, lymphatic vessel, organ, joint, bone, muscle, cartilage, lymph, blood, adipose, ligament, or tendon. In some embodiments, said medical report comprises one or more sentences or phrases describing or assessing said at least one feature. In some embodiments, said system further comprises an audio detection component configured to detect or record an input that indicates when said user accepts inclusion of said computer-generated finding. In some embodiments, said medical image is a radiographic image, a magnetic resonance imaging (MRI) image, an ultrasound image, an endoscopy image, an elastography image, a thermogram image, a positron emission tomography (PET) image, a single photon emission computed tomography (SPECT) image, an optical coherence tomography (OCT) image, a computed tomography (CT) image, a microscopy image, or a medical photography image. In some embodiments, said user is a healthcare provider. In some embodiments, said healthcare provider is a radiologist, a radiologic technician or assistant, a surgeon, a family doctor, an internal medicine physician, a pediatrician, an obstetrician/gynecologist, a dermatologist, an infectious disease physician, a nephrologist, an ophthalmologist, a pulmonologist, a neurologist, an anesthesiologist, an oncologist, a nurse, or a physical therapist. In some embodiments, said method comprises analyzing said image using a machine learning classifier algorithm, thereby generating a result comprising said computer-generated finding. In some embodiments, said computer-generated finding comprises an identification or evaluation of a pathology. In some embodiments, said identification or evaluation of said pathology comprises at least one of a severity, quantity, measurement, presence, or absence of said pathology or a sign or symptom thereof. In some embodiments, said computer-generated finding is included in said medical report when said finding comprises a positive identification or said pathology. In some embodiments, said system uses a cloud-based server or network to perform at least one of analysis of said medical image and generation of said report. In some embodiments, said method comprises providing a worklist management interface allowing said user to reserve one or more cases comprising one or more images from a plurality of cases available for review. In some embodiments, said method comprises determining congruence between said computer-generated finding and a user-finding included in said report. In some embodiments, said method comprises automatically populating a portion of said medical report based on a determination of congruence between said feature and said input. In some cases, said processor is configured to present said computer-generated finding to said user for acceptance and optionally editing, wherein an accepted computer-generated finding is automatically populated into said portion of said report. In some cases, said processor is configured to perform a quality metric assessment of said report. In some cases, said quality metric assessment comprises using natural language processing of said report to generate a list of one or more findings and analyzing said list of one or more findings to generate one or more quality metrics. In some cases, said processor is configured to collect analytics on user interaction with said system and provide feedback for improving efficiency or quality.

Disclosed herein is a computer based system for evaluating a medical image, comprising: (a) a processor; (b) a display; (c) an eye-tracking component coupled to said processor and configured to track a position or a movement of an eye of a user viewing said medical image; (d) a non-transitory computer readable storage medium encoded with a computer program that causes said processor to: (i) display said medical image on said display; (ii) detect said position or said movement of said eye of said user with said eye-tracking component; (iii) analyze said medical image and identify a plurality of features within said medical image; (iv) determine a feature of said plurality of features upon which said user has directed their vision, based at least in part on said position or said movement of said eye of said user; (v) receive an input from said user; and (vi) associate said feature with said input from said user. In some embodiments, said feature and said input from said user are associated based on matching or overlapping time-stamps of said feature and said input. In some embodiments, said system further comprises an audio detection component communicatively coupled to said processor and configured to detect or record one or more sounds spoken by said user that form at least part of said input. In some embodiments, said computer program is configured to cause said processor to analyze said one or more sounds using a speech recognition algorithm to identify one or more words spoken by said user. In some embodiments, said computer program is configured to cause said processor to generate one or more sentences or phrases for insertion into a medical report based at least in part on said one or more words spoken by said user. In some embodiments, said computer program is further configured to cause said processor to automatically generate at least a portion of a medical report based at least in part on said feature and said input. In some embodiments, said computer program is further configured to cause said processor to share or communicate said medical report with a third party. In some embodiments, said medical image is an X-ray radiograph image, a magnetic resonance imaging (MRI) image, an ultrasound image, an endoscopy image, an elastography image, a thermogram image, a positron emission tomography (PET) image, a single photon emission computed tomography (SPECT) image, an optical coherence tomography (OCT) image, a computed tomography (CT) image, a microscopy image, or a medical photography image. In some embodiments, said feature is an identity of an anatomical structure, a measurement of said anatomical structure, a number of said anatomical structure, or a pathology of said anatomical structure. In some embodiments, said system uses a cloud-based server or network to perform at least one of analysis of said image or generation of a portion of a report based on said location and said second input. In some embodiments, said processor is configured to provide a worklist management interface allowing said user to reserve one or more cases comprising one or more images from a plurality of cases available for review.

Disclosed herein is a computer-implemented method for evaluating a medical image, comprising: (a) displaying said medical image on a display; (b) detect a position or movement of an eye of a user with an eye-tracking component; (c) analyzing said medical image and identify a plurality of features within said medical image; (d) determining a feature of said plurality of features upon which said user has directed their vision, based at least in part on said position or said movement of said eye of said user; (e) receiving an input from said user; and (f) associating said feature with said input from said user. In some embodiments, said feature and said input from said user are associated based on matching or overlapping time-stamps of said feature and said input. In some embodiments, said method comprises using an audio detection component to detect or record one or more sounds spoken by said user that form at least part of said input. In some embodiments, said method comprises analyzing said one or more sounds using a speech recognition algorithm to identify one or more words spoken by said user. In some embodiments, said method comprises generating one or more sentences or phrases for insertion into a medical report based at least in part on said one or more words spoken by said user. In some embodiments, said method comprises automatically generating at least a portion of a medical report based at least in part on said feature and said input. In some embodiments, said method comprises sharing or communicating said medical report with a third party. In some embodiments, said medical image is an X-ray radiograph image, a magnetic resonance imaging (MRI) image, an ultrasound image, an endoscopy image, an elastography image, a thermogram image, a positron emission tomography (PET) image, a single photon emission computed tomography (SPECT) image, an optical coherence tomography (OCT) image, a computed tomography (CT) image, a microscopy image, or a medical photography image. In some embodiments, said feature is an identity of an anatomical structure, a measurement of said anatomical structure, a number of said anatomical structure, or a pathology of said anatomical structure. In some embodiments, said method comprises using a cloud-based server or network to perform at least one of analysis of said image or generation of a portion of a report based on said location and said second input. In some embodiments, said method comprises providing a worklist management interface allowing said user to reserve one or more cases comprising one or more images from a plurality of cases available for review.

Disclosed herein is a computer based report generation system, comprising: (a) a processor; (b) a display; (c) a non-transitory computer readable storage medium encoded with a computer program that causes said processor to: (i) display a medical image comprising a plurality of features on said display; (ii) receive an input from said user; (iii) associate said input with a feature from said plurality of features; and (iv) generate a medical report comprising said input, wherein said input within said medical report is associated with a tag, and wherein when said tag is engaged, said feature that is associated with said input is displayed. In some embodiments, each of said plurality of features corresponds to an anatomical structure, a tissue type, a tumor or tissue abnormality, a contrast agent, or any combination thereof. In some embodiments, said input comprises one or more spoken or written words describing or assessing said feature. In some embodiments, said medical image is a radiographic image, a magnetic resonance imaging (MRI) image, an ultrasound image, an endoscopy image, an elastography image, a thermogram image, a positron emission tomography (PET) image, a single photon emission computed tomography (SPECT) image, an optical coherence tomography (OCT) image, a microscopy image, or a medical photography image. In some embodiments, said feature and said input from said user are associated based on matching or overlapping time-stamps of said feature and said input. In some embodiments, said tag comprises a hyperlink. In some embodiments, said user is a radiologist and said medical report comprises a radiologist's report. In some embodiments, said user comprises a healthcare provider.

Disclosed herein is a computer-implemented method comprising: (a) displaying a medical image comprising a plurality of features; (a) receiving an input from a user; (c) associating said input with a feature from said plurality of features; and (d) generating a medical report comprising said input, wherein said input within said medical report is associated with a tag, and wherein when said tag is engaged, said feature that is associated with said input is displayed. In some embodiments, each of said plurality of features corresponds to an anatomical structure, a tissue type, a tumor or tissue abnormality, a contrast agent, or any combination thereof. In some embodiments, said input comprises one or more spoken or written words describing or assessing said feature. In some embodiments, said medical image is a radiographic image, a magnetic resonance imaging (MRI) image, an ultrasound image, an endoscopy image, an elastography image, a thermogram image, a positron emission tomography (PET) image, a single photon emission computed tomography (SPECT) image, an optical coherence tomography (OCT) image, a microscopy image, or a medical photography image. In some embodiments, said feature and said input from said user are associated based on matching or overlapping time-stamps of said feature and said input. In some embodiments, said tag comprises a hyperlink. In some embodiments, said user is a radiologist and said medical report comprises a radiologist's report. In some embodiments, said user comprises a healthcare provider.

Disclosed herein is a computer system comprising: (a) a processor; (b) a display; (c) a non-transitory computer readable storage medium encoded with a computer program that causes said processor to: (i) analyze, in response to an instruction from a user, a medical image using a machine learning software module, thereby generating a computer-finding; (ii) provide said user an option to incorporate said computer-finding into a medical report that is generated by said user; and (iii) analyze said medical report to determine whether said computer-finding is present in said medical report. In some embodiments, said machine learning software module is trained using at least one medical image and at least one corresponding medical report. In some embodiments, said machine learning software module comprises a neural network. In some embodiments, said machine learning software module comprises a classifier. In some embodiments, said medical image is a radiographic image, a magnetic resonance imaging (MRI) image, an ultrasound image, an endoscopy image, an elastography image, a thermogram image, a positron emission tomography (PET) image, a single photon emission computed tomography (SPECT) image, an optical coherence tomography (OCT) image, a computed tomography (CT) image, a microscopy image, or a medical photography image. In some embodiments, natural language processing is used to analyze said medical report. In some embodiments, said medical report comprises a radiology report.

Disclosed herein is a computer-implemented method comprising: (a) analyzing, in response to an instruction from a user, a medical image using a machine learning software module, thereby generating a computer-finding; (b) providing said user an option to incorporate said computer-finding into a medical report that is generated by said user; and (c) analyzing said medical report to determine whether said computer-finding is present in said medical report. In some embodiments, said machine learning software module is trained using at least one medical image and at least one corresponding medical report. In some embodiments, said machine learning software module comprises a neural network. In some embodiments, said machine learning software module comprises a classifier. In some embodiments, said medical image is a radiographic image, a magnetic resonance imaging (MRI) image, an ultrasound image, an endoscopy image, an elastography image, a thermogram image, a positron emission tomography (PET) image, a single photon emission computed tomography (SPECT) image, an optical coherence tomography (OCT) image, a computed tomography (CT) image, a microscopy image, or a medical photography image. In some embodiments, natural language processing is used to analyze said medical report. In some embodiments, said medical report comprises a radiology report.

Disclosed herein is a computer based image analysis system, comprising (a) a processor; (b) a display; (c) a non-transitory computer readable storage medium encoded with a computer program that causes said processor to: (i) receive a medical image; and (ii) provide said medical image as an input to an image analysis algorithm comprising a first module and a second module, wherein said first module generates a first output based on at least said input, and wherein said second module generates a second output based on at least said input and said first output of said first module. In some embodiments, the processor is further caused to display said medical image with said first output and said second output generated by said image analysis algorithm. In some embodiments, said image analysis algorithm comprises a neural network architecture. In some embodiments, said first module and said second module each comprise one or more layers of neurons. In some embodiments, said neural network architecture comprises a sequence of modules, wherein each succeeding module in the sequence of generates an output based on said medical image and an output of a preceding module. In some embodiments, said sequence of modules are arranged in order of analytical difficulty with each succeeding module having a higher difficulty output than each preceding module. In some embodiments, said neural network architecture comprises skip connections between artificial neuron layers. In some embodiments, said skip connections occur across different modules in the sequence of modules of the neural network architecture. In some embodiments, said first output and said second output each comprise one or more segments or labels corresponding to said medical image. In some embodiments, each module of said image analysis algorithm comprises a classifier. In some embodiments, said medical image is a radiographic image, a magnetic resonance imaging (MRI) image, an ultrasound image, an endoscopy image, an elastography image, a thermogram image, a positron emission tomography (PET) image, a single photon emission computed tomography (SPECT) image, an optical coherence tomography (OCT) image, a computed tomography (CT) image, a microscopy image, or a medical photography image. In some embodiments, the processor is further caused to generate a medical report comprising one or more computer-findings based on one or more of said first output and said second output. In some embodiments, said medical report comprises a radiology report.

Disclosed herein is a computer implemented method, comprising: (i) receiving a medical image; and (ii) providing said medical image as an input to an image analysis algorithm comprising a first module and a second module, wherein said first module generates a first output based on at least said input, and wherein said second module generates a second output based on at least said input and said first output of said first module. In some embodiments, the method further comprises displaying said medical image with said first output and said second output generated by said image analysis algorithm. In some embodiments, said image analysis algorithm comprises a neural network architecture. In some embodiments, said first module and said second module each comprise one or more layers of neurons. In some embodiments, said neural network architecture comprises a sequence of modules, wherein each succeeding module in the sequence of generates an output based on said medical image and an output of a preceding module. In some embodiments, said sequence of modules are arranged in order of analytical difficulty with each succeeding module having a higher difficulty output than each preceding module. In some embodiments, said neural network architecture comprises skip connections between artificial neuron layers. In some embodiments, said skip connections occur across different modules in the sequence of modules of the neural network architecture. In some embodiments, said first output and said second output each comprise one or more segments or labels corresponding to said medical image. In some embodiments, each module of said image analysis algorithm comprises a classifier. In some embodiments, said medical image is a radiographic image, a magnetic resonance imaging (MRI) image, an ultrasound image, an endoscopy image, an elastography image, a thermogram image, a positron emission tomography (PET) image, a single photon emission computed tomography (SPECT) image, an optical coherence tomography (OCT) image, a computed tomography (CT) image, a microscopy image, or a medical photography image. In some embodiments, the method further comprises generating a medical report comprising one or more computer-findings based on one or more of said first output and said second output. In some embodiments, said medical report comprises a radiology report.

Disclosed herein is a computer system configured to provide a hanging protocol, comprising (a) a processor; (b) a display; (c) a non-transitory computer readable storage medium encoded with a computer program that causes said processor to: (i) receive user input defining one or more criteria for optimization; and provide a hanging protocol based on said one or more criteria. In some embodiments, the system is configured to obtain an image study or image series comprising one or more images; receive user input defining one or more criteria for optimization; and provide a hanging protocol optimized for said image study based on said one or more criteria. In some embodiments, the hanging protocol is not optimized based on hard coding (e.g., preset rules establishing requisite criteria) of criteria that is allowed or not allowed. In some embodiments, the hanging protocol is optimized based on numerical optimization. In some embodiments, the criteria correspond to one or more study attributes. In some embodiments, the criteria comprise one or more prior image studies. In some embodiments, the criteria comprise one or more prior image studies comprising one or more images or image series. In some embodiments, one or more prior image studies are selected by a user to establish criteria. In some embodiments, the hanging protocol is optimized based on one or more attributes extracted from the one or more prior image studies. In some embodiments, optimization of the hanging protocol comprises selection of an optimal hanging protocol from a plurality of hanging protocols based on one or more attributes extracted from one or more prior image studies. In some embodiments, optimization of the hanging protocol comprises obtaining information from at least one of imaging order, clinical text, metadata (e.g., DICOM metadata), or image data (e.g., DICOM pixel data) for the image study. In some embodiments, optimization of the hanging protocol comprises using a natural language processing algorithm to extract one or more relevant features from the imaging order, clinical text, or both. In some embodiments, optimization of the hanging protocol comprises extracting relevant features from the image data using a computer vision algorithm. In some embodiments, the computer vision algorithm is configured to identify or extract visual features that provide information about study attributes. In some embodiments, optimization of the hanging protocol extracting features from the metadata (e.g., DICOM metadata). In some embodiments, optimization of the hanging protocol comprises providing extracted features as input to a machine learning classifier to generate as output one or more attributes. In some embodiments, the hanging protocol is optimized according to the one or more attributes generated by the machine learning classifier.

In some embodiments, disclosed herein is a method for providing a hanging protocol, comprising: receiving user input defining one or more criteria for optimization; and providing a hanging protocol based on said one or more criteria. In some embodiments, disclosed herein is a method for providing a hanging protocol, comprising: obtaining an image study or image series comprising one or more images; receiving user input defining one or more criteria for optimization; and providing a hanging protocol optimized for said image study based on said one or more criteria. In some embodiments, the hanging protocol is not optimized based on hard coding (e.g., preset rules establishing requisite criteria) of criteria that is allowed or not allowed. In some embodiments, the hanging protocol is optimized based on numerical optimization. The hanging protocol systems, software, and methods can be used in combination with any of the other systems, software, and methods disclosed herein to the extent they relate to viewing, reviewing, analyzing, or otherwise interacting with images (e.g., AI-assisted findings, automated report generation, etc.). As an illustrative example, a user may use a system that performs AI-assisted image segmentation and generation of findings for automated/semi-automated report generation, which utilizes a hanging protocol system/subsystem for provisioning the display and layout of images as part of the review of the medical image. In some embodiments, the criteria correspond to one or more study attributes. In some embodiments, the criteria comprise one or more prior image studies. In some embodiments, the criteria comprise one or more prior image studies comprising one or more images or image series. In some embodiments, one or more prior image studies are selected by a user to establish criteria. As an illustrative example, a user selects several exemplar image studies or image series relating to chest X-rays to set criteria for future chest X-ray image studies or image series. The relevant features from these prior image studies or image series are extracted and used to determine the one or more attributes used to optimize the hanging protocol that is ultimately used for the current image study or image series. In some embodiments, the hanging protocol is optimized based on one or more attributes extracted from the one or more prior image studies. In some embodiments, optimization of the hanging protocol comprises selection of an optimal hanging protocol from a plurality of hanging protocols based on one or more attributes extracted from one or more prior image studies. In some embodiments, optimization of the hanging protocol comprises obtaining information from at least one of imaging order, clinical text, metadata (e.g., DICOM metadata), or image data (e.g., DICOM pixel data) for the image study. In some embodiments, optimization of the hanging protocol comprises using a natural language processing algorithm to extract one or more relevant features from the imaging order, clinical text, or both. In some embodiments, optimization of the hanging protocol comprises extracting relevant features from the image data using a computer vision algorithm. For example, the computer vision algorithm can be configured to identify or extract visual features that provide information about study attributes. In some embodiments, optimization of the hanging protocol extracting features from the metadata (e.g., DICOM metadata). In some embodiments, optimization of the hanging protocol comprises providing extracted features as input to a machine learning classifier to generate as output one or more attributes. In some embodiments, the hanging protocol is optimized according to the one or more attributes generated by the machine learning classifier.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 10 shows the traditional clinical workflow for producing a radiology report and the workflow for peer review of the report.

DETAILED DESCRIPTION

Figure 1:
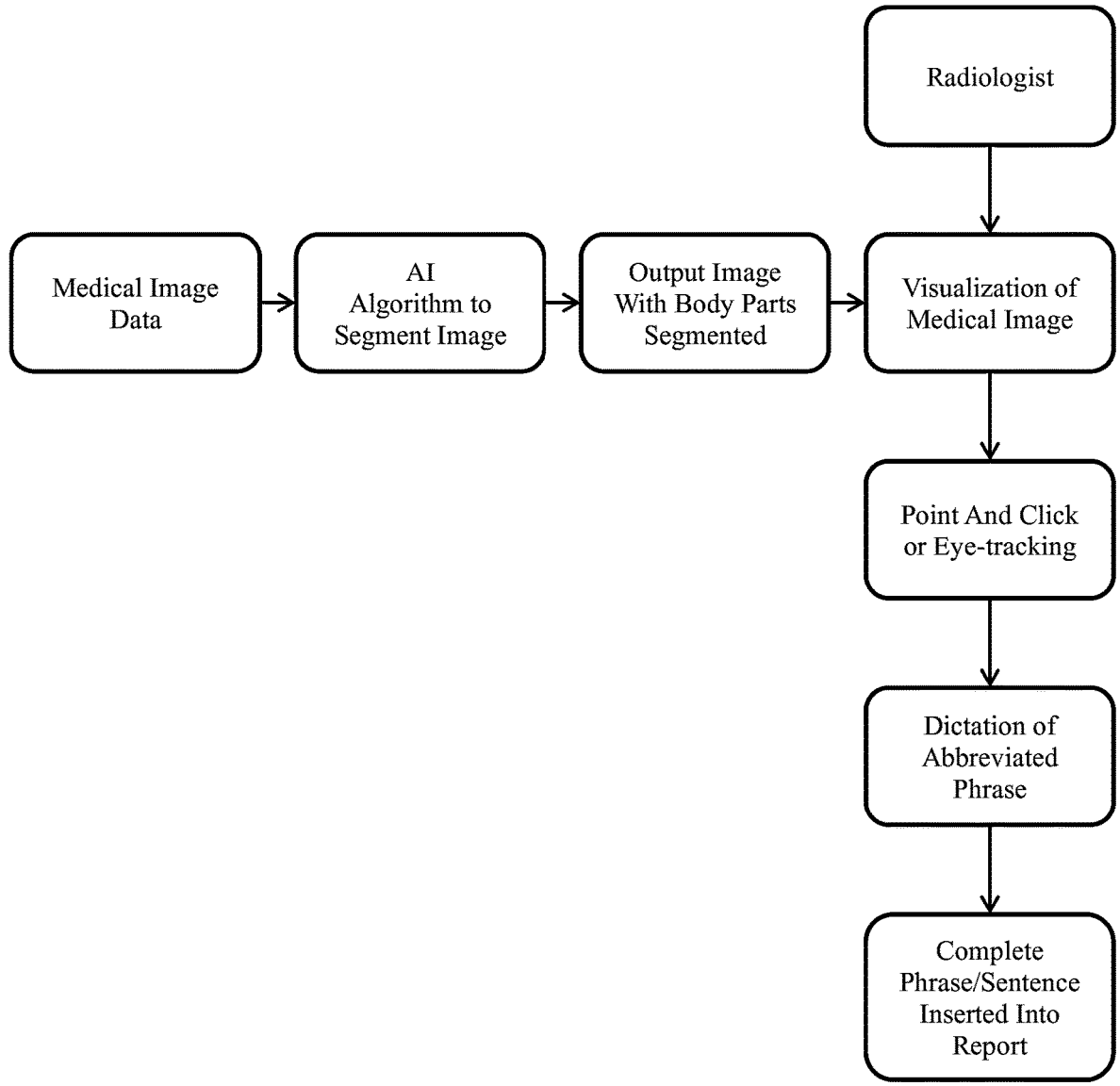
FIG. 1 shows a flow chart illustrating a non-limiting example of a process for segmentation and labeling of a medical image using an AI algorithm, visualization, and capture & analysis of user interaction to generate a finding for insertion into a report.

Described herein are systems, software, and methods for facilitating AI-assisted interpretation and reporting of medical images. Medical images can be visualized on a display, and a user such as a radiologist is able to interpret the images using a streamlined process to efficiently generate findings for insertion into a medical report. User input can include movement or position of the mouse or other input device, alternatively or in combination with gaze fixation point input detected using eye-tracking equipment and software. The user input can enable the system to detect what portion of an image the user is selecting or looking at. The portion of the image may be segmented and labeled according to an image segmentation algorithm, which can be configured to account for anatomic variants. In addition, user dictation of an evaluation or interpretation of the selected portion of the image can be converted into text through audio detection and analysis algorithms. The combination of user input and dictation may be used to generate a clinical finding corresponding to the selected portion of the image. The finding can be constructed based on the clinical context inferred from the user input at the time of the dictation (e.g., shared timestamp), for example, specifying the anatomic segment the user was "looking at" or "pointing at" (e.g., L4-L5 disc) when dictating an analysis (e.g., "disc herniation") along with any useful measurement(s) (e.g., dimension(s) of the disc). Once the findings text has been generated, the system may present the user with the option to amend and/or confirm the finding before insertion into the medical report, which is optionally integrated with a payment/charge subsystem that processes the charge based on user confirmation. Algorithms can be applied to the findings in a report to determine congruence or discordance between AI-generated findings and the user dictation/input, which may be provided to help the user with amending/confirming the findings when finalizing the report. The final report can be configured to infer and/or link one or more findings to the clinical context within which they were generated, for example, linking a finding to the most informative image and/or image segment used to arrive at the finding (e.g., tagging a finding with a hyperlink to the image and input used to generate the finding). This enables a subsequent viewer of the report to visualize the same information used by the original user or radiologist to allow for a more informed assessment or confirmation of the original finding. In addition, the system can provide intelligent worklist management and/or communications prioritization and queueing to improve workflow efficiency (e.g., for image studies and/or image series). The system can use automated generation and tracking of quality measures to provide assessment and feedback of user/radiologist performance. User interaction with the system itself may also be captured to improve performance. In some cases, the system generates or provides hanging protocols based on various criteria for optimal image placement. The systems, software, and methods can include any combination of the processes and/or functions described herein.

Accordingly, the systems, software, and methods disclosed herein can incorporate one or more of the processes or subsystems disclosed herein, including but not limited to, AI-assisted image segmentation and labeling, AI-assisted dictation of findings and/or measurements, comparison, and query, bi-directional dynamic linking of findings, AI finding display and interaction, tracking and analyzing AI assistance, communications hub for radiologists, worklist management, AI-enabled quality metrics, AI-assisted self-improvement, and AI for hanging protocols. Algorithms that can be used in the processes or subsystems include various models such as computer vision and natural language processing algorithms disclosed herein. Accordingly, the present disclosure contemplates any combination of the systems/subsystems and methods disclosed herein including the foregoing list of subsystems and methods described in this paragraph.

Disclosed herein is a computer based system for medical report generation, comprising: (a) a processor; (b) a display configured to show a graphical user interface for evaluating a medical image; (c) a non-transitory computer readable storage medium encoded with a computer program that causes said processor to: (i) generate a medical report including a computer-generated finding related to said medical image when a user accepts inclusion of said computer-generated finding within said report.

Disclosed herein is a computer-implemented method for medical report generation, comprising: (a) displaying a medical image; (b) generating a medical report including a computer-generated finding related to said medical image when a user accepts inclusion of said computer-generated finding within said report.

Disclosed herein is a computer based system for evaluating a medical image, comprising: (a) a processor; (b) a display; (c) an eye-tracking component coupled to said processor and configured to track a position or a movement of an eye of a user viewing said medical image; (d) a non-transitory computer readable storage medium encoded with a computer program that causes said processor to: (i) display said medical image on said display; (ii) detect said position or said movement of said eye of said user with said eye-tracking component; (iii) analyze said medical image and identify a plurality of features within said medical image; (iv) determine a feature of said plurality of features upon which said user has directed their vision, based at least in part on said position or said movement of said eye of said user; (v) receive an input from said user; and (vi) associate said feature with said input from said user.

Disclosed herein is a computer-implemented method for evaluating a medical image, comprising: (a) displaying said medical image on a display; (b) detect a position or movement of an eye of a user with an eye-tracking component; (c) analyzing said medical image and identify a plurality of features within said medical image; (d) determining a feature of said plurality of features upon which said user has directed their vision, based at least in part on said position or said movement of said eye of said user; (e) receiving an input from said user; and (f) associating said feature with said input from said user.

Disclosed herein is a computer based report generation system, comprising: (a) a processor; (b) a display; (c) a non-transitory computer readable storage medium encoded with a computer program that causes said processor to: (i) display a medical image comprising a plurality of features on said display; (ii) receive an input from said user; (iii) associate said input with a feature from said plurality of features; and (iv) generate a medical report comprising said input, wherein said input within said medical report is associated with a tag, and wherein when said tag is engaged, said feature that is associated with said input is displayed.

Disclosed herein is a computer-implemented method comprising: (a) displaying a medical image comprising a plurality of features; (a) receiving an input from a user; (c) associating said input with a feature from said plurality of features; and (d) generating a medical report comprising said input, wherein said input within said medical report is associated with a tag, and wherein when said tag is engaged, said feature that is associated with said input is displayed.

Disclosed herein is a computer system comprising: (a) a processor; (b) a display; (c) a non-transitory computer readable storage medium encoded with a computer program that causes said processor to: (i) analyze, in response to an instruction from a user, a medical image using a machine learning software module, thereby generating a computer-finding; (ii) provide said user an option to incorporate said computer-finding into a medical report that is generated by said user; and (iii) analyze said medical report to determine whether said computer-finding is present in said medical report.

Disclosed herein is a computer-implemented method comprising: (a) analyzing, in response to an instruction from a user, a medical image using a machine learning software module, thereby generating a computer-finding; (b) providing said user an option to incorporate said computer-finding into a medical report that is generated by said user; and (c) analyzing said medical report to determine whether said computer-finding is present in said medical report.

AI-Assisted Image Segmentation and Labeling

Described herein are systems, software, and methods for facilitating AI-assisted interpretation and reporting of medical images. In some cases, the systems, software, and methods provide AI-assisted image segmentation and/or labeling, including the labeling of anatomic variants). These processes can be implemented via a system, subsystem, or module, which can be stand-alone or part of a larger platform or system as disclosed herein. Medical images such as, for example, X-rays or MRIs can be evaluated using an image segmentation algorithm to partition the image into one or more regions. The regions can be sets of pixels that correspond to objects or boundaries that share certain anatomic characteristics. For example, an X-ray image of human vertebrae can be segmented to partition the image into segments that correspond to the individual bones. Segmentation provides a representation of a medical image that can be medically relevant, and thus suitable for inclusion within an analysis or report. The segments in an image can be defined according to one or more labels assigned to the individual pixels. Accordingly, the pixels that make up a vertebra segment would share a common label for the vertebra. Segmented portions of the image and/or labels applied the image or its segmented portions can be used as computer-findings.

In some cases, image segmentation is performed by an image segmentation module. The image segmentation module may be a component module of an anatomic navigator module.

In some cases, image segmentation generates one or more regions that encompass at least a portion of the entire image, or alternatively or in combination, one or more contours or edges detected in the image. These regions or contours are made up of pixels that share one or more similar characteristics or properties. Non-limiting examples of such characteristics include color, density, intensity, and texture. Adjacent regions are generally detected based on differences in one or more such characteristics. In some cases, image segmentation is performed based on a single characteristic, or alternatively, a combination of one or more characteristics. The medical image can be a 2D image or a 3D image or higher dimensional if time or other parameters vary across volumes.

Image segmentation and labeling of detailed human anatomy is difficult, especially given the natural variation in anatomy and the possible presence of pathology. This difficulty is especially apparent in cases where there are numerous distinct regions to be segmented and labeled (e.g., spine with 24 vertebrae and 23 intervertebral discs) such that the task goes beyond foreground vs. background (2 classes). Additionally, some anatomic structures may be significantly more subtle than others in a given imaging modality. Accordingly, disclosed herein are systems, software, and methods that comprise a progressive reasoning approach that is capable of solving a set of easy to difficult problems by learning to solve the easy problems and then progressively using those inferences in order to inform progressively more difficult problems until the entire set of problems is solved.

In some embodiments, image segmentation is performed on multiple anatomic parts that takes into account anatomic variants where the number of anatomic components, the shape/morphology of those components, or the spatial relationship between those components may vary from patient to patient.

In some cases, the image segmentation algorithm is configured to detect anatomic variants. While a subject will usually have the predominant anatomic structure, there exist variants that a deficient algorithm can fail to account for. As an example, the spine is split into different sections with different numbers of vertebrae or segments. The vertebrae typically include 7 cervical vertebrae, 12 thoracic vertebrae, 5 lumbar vertebrae, 5 sacral vertebrae, and 4 coccygeal vertebrae for a total of 33 vertebrae. However, variations in the spinal anatomy are fairly common and many of them can potentially cause confusion in the labeling of the vertebrae.

According to Durand et al (Mag Res Imaging Clin N Am 18 2010), there are several classes of anatomic variants. The first class is variants of formation due to failures of development including hemivertebrae and wedge vertebrae. The second class is variants of segmentation where contiguous vertebral bodies fail to separate during development including block vertebrae, unilateral bar vertebrae, and atlantooccipital fusion. The third class of variants is variants of fusion and cleft formation including os odontoideum, butterfly vertebra, spina bifida occulta, and limbus vertebrae. Examples of miscellaneous variants include fatty filum terminale, persistent notochord, Schmorl's nodes, and transitional vertebrae. These variants are manifested as either changes in the general appearance of each vertebrae, changes in the overall layout and configuration of vertebrae, and possibly even changes in the numbers and labels of vertebrae.

The clinical significance of radiographically mislabeled vertebrae cannot be overstated as an incorrect vertebral label could cause a surgical procedure or injection at the wrong level. Another complicating factor is that if a patient has an anatomic variant, then clinical correlation of symptoms may be erroneous as well. Thus, in the field of automated image segmentation, the ability to accurately segment medical images including images of anatomic variants is of great importance.

Accordingly, disclosed herein are systems, software, and methods for performing image segmentation using segmentation algorithms that are configured to detect anatomic variants. In some cases, localizer or scout images are used to enhance image segmentation. These are generally lower resolution but wider field of view images that are acquired for the purposes of properly positioning the higher resolution diagnostic image acquisition. As an example, if the entire spine is not within the field of view of the image series being analyzed, a shift of the labels by one or more vertebrae is more likely, especially in the presence of anatomic variants. In some cases, large field of view localizer images are used, especially sagittal, if they have been acquired to identify the overall sequence and identity of vertebrae. A putative labeling of vertebrae can be made from the localizer image in the cranial to caudal direction. If the image series share the same DICOM frame of reference UID, then a shared coordinate system may be assumed, and putative labels transferred directly. If the image series do not share a frame of reference, then the images can be registered with each other in order to establish a shared frame of reference. In some embodiments, large field of view, low-resolution localizer/scout images are used in order to provide greater context than the diagnostic smaller field of view images. For instance, determining the correct labels of the vertebrae usually involves counting from either end of the spine (either the C1 vertebra or the sacrum).

Figure 22:
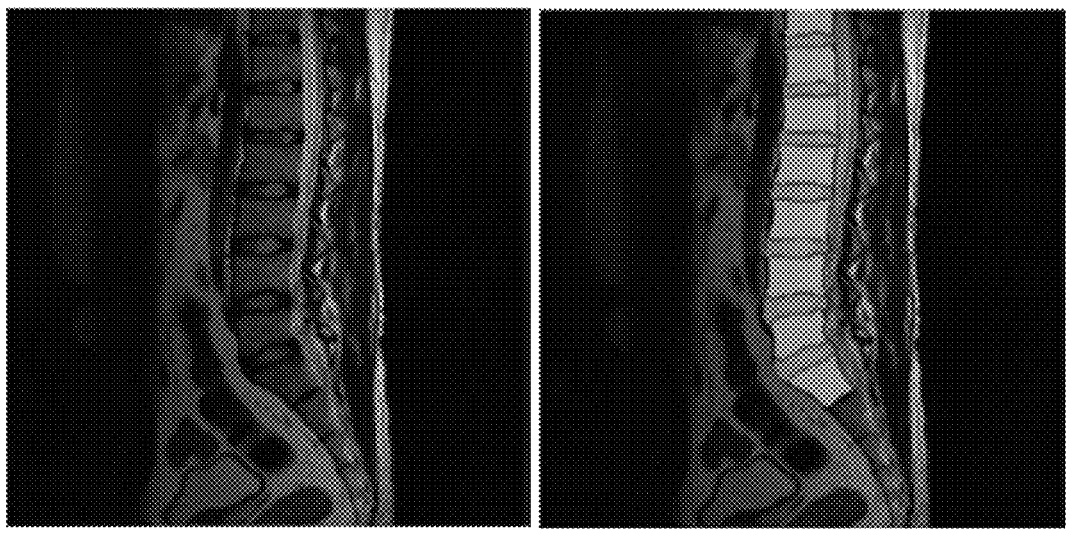
FIG. 22 shows an illustrative example of a medical image with all the visible vertebrae segmented as a single class and all of the visible discs are segmented as a single class with no attempt to distinguish between individual vertebrae.

In some cases, image segmentation is performed on an image of the spine. As an example, input images to the segmentation module are MRI T2-weighted sagittal images of the spine. Image segmentation can be performed to distinguish between the following four classes: vertebra, intervertebral disc, spinal cord, and background. At this stage, the visible vertebrae are segmented as a single class and the visible discs are segmented as a single class with no attempt to distinguish between individual vertebrae (FIG. 22).

Image segmentation can be performed using a variety of techniques including convolutional neural networks (CNN). As an illustrative example, image segmentation is performed using a 2.5D fully convolutional network (FCN) using cross entropy loss with an Adam optimizer (Long J et al., arXiv 2015). In some cases, images are resized and intensity normalized. Hyperparameter search is performed via a grid search. Regularizations include early stopping criteria, batch normalization, and dropout. In some cases, a single FCN model is used for segmentation of cervical, thoracic, and lumbar spine imaging studies. As shown in FIG. 22, the anatomic navigator shows spine segmentation with the original source images shown on left and computed segmentation shown on right with vertebral bodies in yellow and intervertebral discs in blue.

In some cases, the segmentation algorithm performs optimization of label assignment to define the anatomic class of each region. Localizer images typically have a wider field of view which allows for the identification of a reference point from which to start numbering the anatomy (e.g., C1 vertebra numbering in the caudal direction or S1 vertebra numbering in the cranial direction). In one case, the labels are determined from the localizer first and then transferred to the series under consideration. In another case, there is a dynamic adjustment of labels using both global information from the localizer and more localized information from the series under consideration such that the labels would be adjusted in both localizer and the series under consideration.

In some cases, the assignment of vertebral labels to individual regions within the several image series is posed as an optimization problem that is solved with dynamic programming or other optimization framework. Analogous to a sequence alignment problem of two DNA sequences, the two sequences to be aligned are the sequence vertebral bodies identified in the images and the sequence of vertebral labels. The scoring function can contain a sequence-to-sequence score that computes a cost of each vertebral label to each image region. For instance, if a particular image region contained a vertebra with an inferiorly projecting spinous process, the algorithm may assign it a greater score for a match with a thoracic vertebral label (T1-T12) than for other matches. The scoring function can also contain an intra-sequence score for both image regions and for vertebral labels. For image regions, if the piecewise linear sequence of centroids zigs back and forth (containing acute angles), then it may receive a lower score than if relatively straight (obtuse angles) are used. For the sequence of vertebral labels, out of order sequences (e.g., T5-T7-T6) may receive much lower scores.

Figure 23:
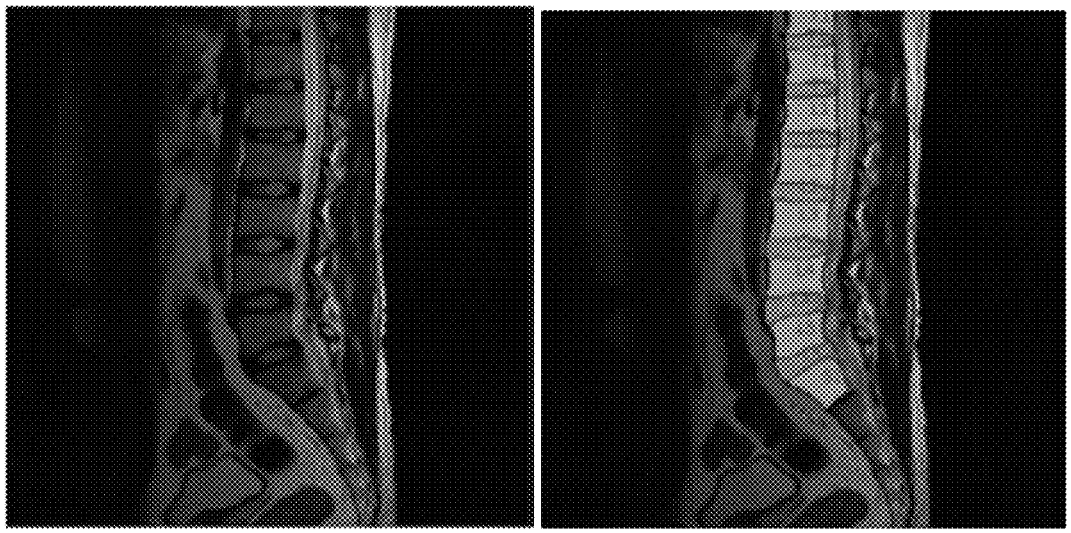
FIG. 23 shows an illustrative example of a medical image with labeling of the segmented spine that subdivides the region representing all vertebrae into individual vertebrae and the region representing all intervertebral discs into individual discs with the original source image shown on left and labeled segmented image shown on right.

In one example of image labeling of the spine, the region representing all vertebrae are subdivided into individual vertebrae (C1 through S1) and the region representing all intervertebral discs into individual discs (C2-C3 through L5-S1). An example of spinal labeling is shown in FIG. 23. Points corresponding to left/right foramen and left/right facet joints are placed at each intervertebral disc level. For lumbar studies, a single point may be placed at the conus medullaris. The user may turn on or off visualization any of these regions/points and/or text labels if so desired. In some cases, the entire spine model with labels is visualized in 3D. Vertebra and disc labeling can be performed using various machine learning algorithms, for example, a network such as a convolutional neural network (CNN). An illustrative non-limiting example is a 2.5D DeepLab v3 neural network using cross entropy loss with an Adam optimizer (Chen L C et al., IEEE PAMI 2018). Images can be resized and the intensity normalized. Hyperparameter search can be performed via a grid search. Regularizations may include early stopping criteria, batch normalization, and dropout. Landmark detection of left/right foramen, left/right facet joints, and conus can be performed using a Convolutional Pose Machine (CPM), which combines the long-range image sequence advantages of pose machines with the feature detection and spatial context awareness advantages of convolutional neural networks (Wei S E et al., arXiv 2016). These networks can be evaluated through Euclidean distance metrics and Percentage Correct Keypoint (PCK) metrics.

In some cases, the segmentation and/or labeling algorithm is a machine learning algorithm such as, for example, a deep learning neural network configured to segment and/or label anatomic structures or features in one or more medical images. Further description of the image segmentation and/or labeling algorithms can be found throughout the present disclosure, such as relating to computer vision.

Figure 25:
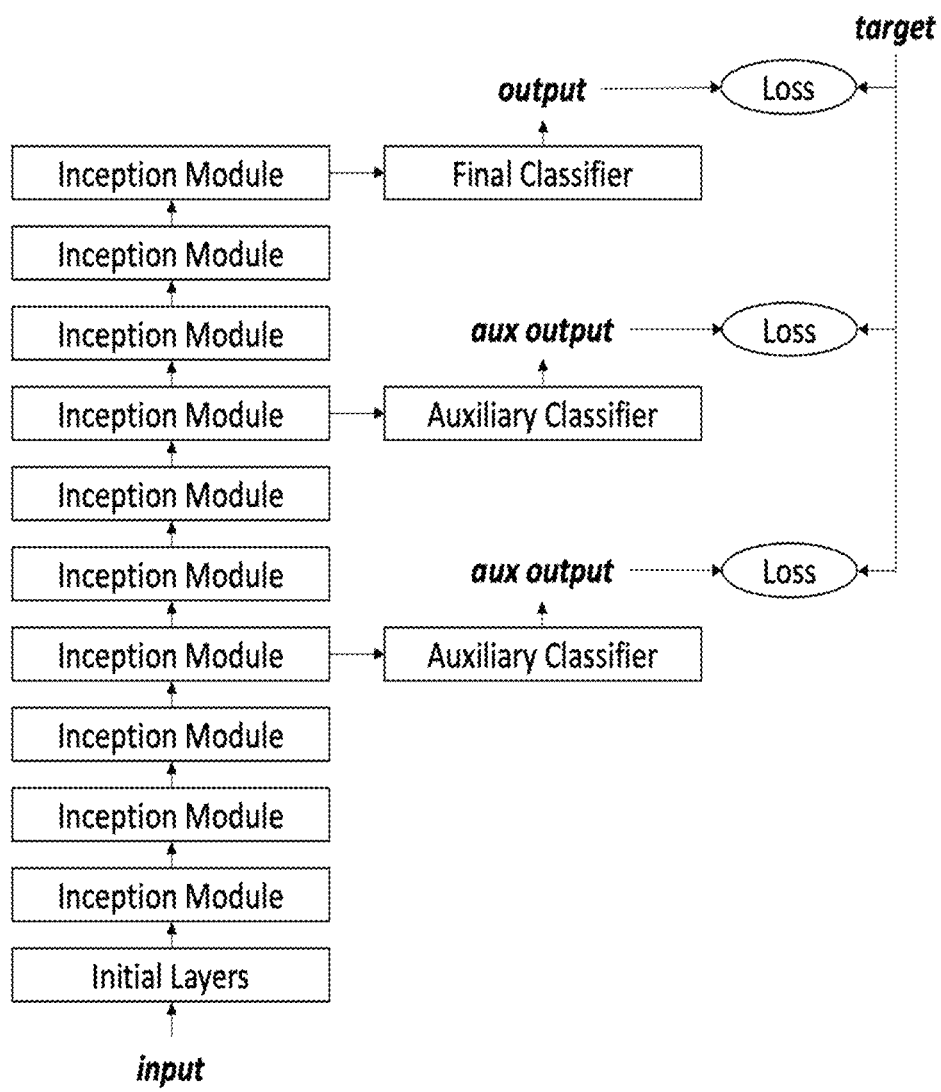
FIG. 25 shows an illustrative diagram of the relationship between layers and modules with classifiers used to generate an output.

In some embodiments, a neural network architecture is used to perform image segmentation and anatomic structure or feature labeling. An example of a neural network architecture is Inception, which has been used to successfully solve various machine learning problems (Szegedy, et al., 2014). Amongst other innovations, this architecture addresses the problem of disappearing gradients during backpropagation by adding auxiliary classifiers at intermediate modules from input to output. Each module consists of one or more artificial neural layers. These auxiliary classifiers, which also consist of one or more artificial neural layers, inject gradient values into the earlier modules where they would otherwise have been greatly diminished starting from the output. Notably, in this architecture, all of the classifier outputs are identical. FIG. 25 shows an abstracted neural network architecture for Inception. Auxiliary classifiers are added at intermediate modules in order to increase the gradient signal that gets propagated from output back to input. During training, the targets used for computing the loss function are identical between final classifier and auxiliary classifiers.

Disclosed herein are systems, software, and methods for performing image segmentation and/or labeling using a progressive reasoning approach that provides various advantages over existing approaches such as the use of auxiliary classifiers in Inception. As an illustrative example, a neural network architecture incorporating progressive reasoning can be used to provide greater segmentation and/or labeling accuracy for complex images. In some embodiments, the algorithm for performing image segmentation and/or labeling comprises an image analysis architecture made up of a series of modules in which each module analyzes a respective component of the image to generate a corresponding output. The first module performs an analysis of the input data (e.g., image data) and generates an output. Each succeeding module can analyze both the input data or a portion thereof along with the output of the preceding module to generate a next output. Thus, the earlier outputs are used in the subsequent reasoning process unlike the use of auxiliary classifiers in Inception where the intermediate outputs are used in a much narrower way, only to contribute to the loss function. The modules can be arranged in a sequence of increasing difficulty of the analytical task such that the incorporation of the output of each preceding module into the analysis performed by each succeeding module enhances the accuracy of the analysis of the succeeding module.

Figure 26:
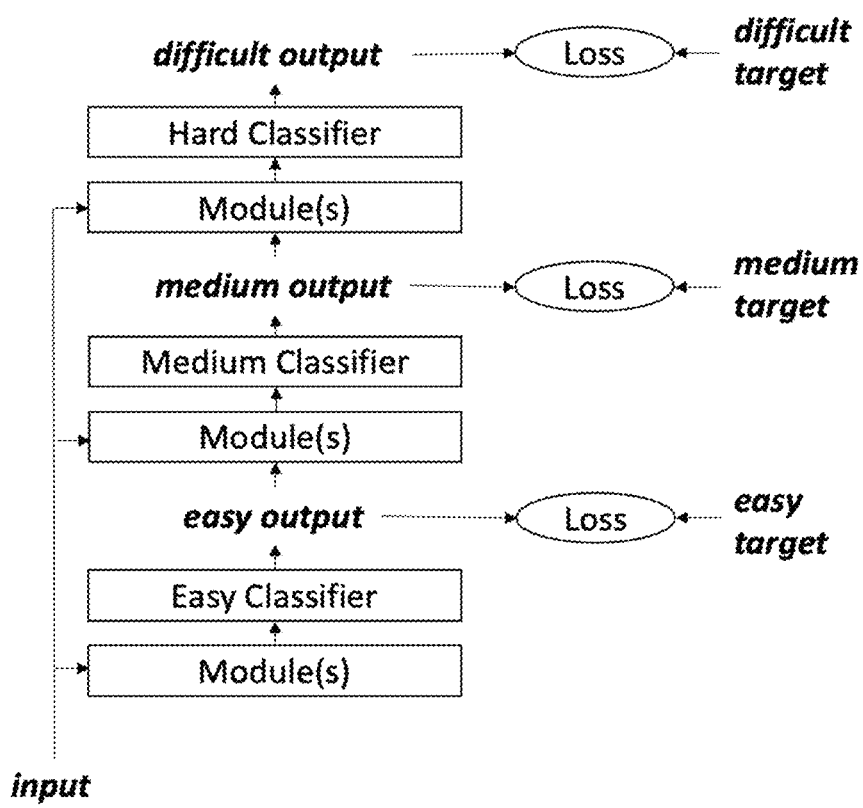
FIG. 26 shows an illustrative neural network architecture for progressive reasoning comprising skip connections (not shown) between artificial neuron layers.
Figure 27:
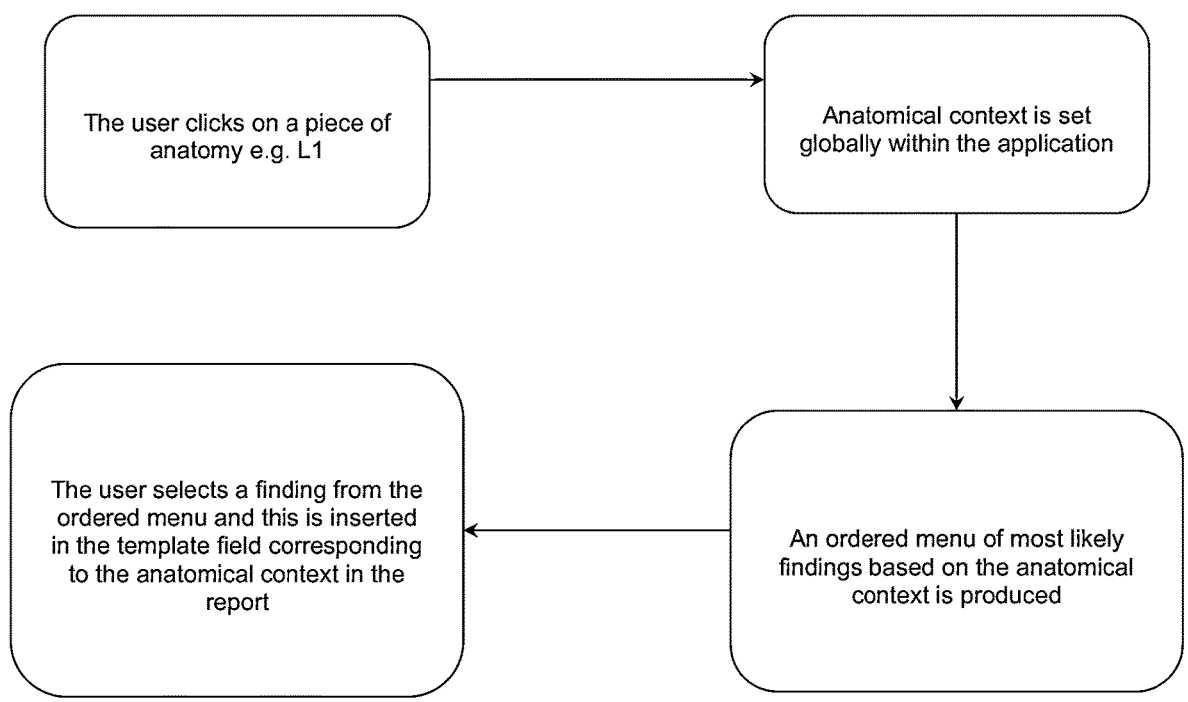
FIG. 27 shows a flow chart illustrating AI-assisted findings during report generation.

FIG. 26 provides an abstracted diagram of a non-limiting embodiment of a neural architecture for progressive reasoning. As shown, the neural architecture employs a series of three modules analyzing the original image and the output of the preceding module. In this embodiment, the levels of output are divided into easy, medium, and difficult in terms of task complexity. An arbitrary number of complexity levels could be used with this architecture, for example, at least 2, 3, 4, 5, 6, 7, 8, 9, or 10 or more levels. Subsequent to the first level, the original input images or image data can be concatenated with the previous level output to become input to the next level. Note also that gradients are back-propagated across each level as well. The assignment of complexity level to various anatomic regions may be estimated manually by taking into consideration the subtlety of appearance and reliance upon nearby anatomic structures to localize the anatomic region. Alternatively, this could be determined quantitatively by ranking segmentation accuracy given a neural network that does not use progressive reasoning whereby lower accuracy anatomic regions would be considered more difficult.

The "progressive reasoning" approach can be applied to almost any neural network architecture that is applied to problems with multiple desired outputs. For instance, the outputs may represent numerous anatomic regions in a multiple category image segmentation task. Some of the outputs may be relatively easy to determine, while others are difficult to determine for both human experts and for algorithms. An example would be in segmentation of multiple regions of a knee MRI, in which the bones (femur, patella, tibia, fibula) are generally easy to delineate while cartilage may be of medium difficulty, and ligaments (PCL, ACL, MCL, LCL) may be most difficult.

Another example is in the segmentation and labeling of vertebra in an MRI or CT image. One of the difficulties in this task is that the vertebrae have a similar appearance which makes labeling prone to the problem of being off by one (or more) in the labeling. Most human interpretation begins by identifying the end of the spine (either C1/C2 below the base of the skull in cervical spine or S1 at the sacrum in lumbar spine) from which the counting begins. As an illustrative example, the progressive reasoning approach uses the end (C1/C2 or S1) as the easy task and then progressively solves the task of segmenting and labeling each vertebrae in sequence from there (proceeding either caudally or cranially, respectively). To limit the number of difficulty levels, vertebrae may be progressively considered in groups of 2-4. Similar examples can be found for every combination of anatomy and image acquisition modality. Non-limiting examples of the anatomy that can be imaged for segmentation and/or labeling according to the methods disclosed herein include the head, brain, torso, abdomen, heart, lung, prostate, breast, lymph, thyroid, spleen, adrenal gland, colon, rectum, bladder, ovaries, skin, liver, spine, bone, pancreas, cervix, salivary gland, sebaceous gland, testis, thymus gland, penis, uterus, and other anatomical regions, organs, or tissues. In some embodiments, the image includes a large portion of the body such as the torso or a limb (e.g., arm or leg). In some embodiments, the image includes an organ system, for example, the cardiovascular system, the skeletal system, the gastrointestinal system, endocrine system, or the nervous system. The anatomic region, organ, or tissue can be diseased or injured or include one or more artifacts or features of disease or injury. For example, a mammogram may include image features indicative of a tumor, or an X-ray of an arm may include image features indicative of a broken humerus.

Various types of images can be analyzed as described according to the present disclosure, for example, magnetic resonance imaging (MRI), CT (computerized tomography), CAT (computerized axial tomography), positron emission tomography (PET), single photon emission computed tomography (SPECT), ultrasound, X-ray images, and other types of medical images.

Another example of multiple desired outputs may involve different tasks applied to the same input data. For instance, the easy output may be the image segmentation task, the medium output might be labeling the anatomic regions, and the difficult task might be detecting pathology within those regions. This progressive reasoning architecture could also be applied assuming that the information inferenced at the earlier stages is informative for the later more difficult stages. The graded difficulty stages are not limited to 3 and can be any arbitrary number based on the level of specificity desired.

In some embodiments, the loss functions for each of these stages is computed separately and contribute additively or non-linearly to an overall loss function. For instance, the losses might be a linear combination with possibly smaller coefficients for the earlier losses. Alternatively, the losses might be raised to a power prior to linear combination.

In some embodiments, the input to the easy stage is the raw input for the overall task. In the case of image segmentation, the raw input would be the source images themselves. In some embodiments, the raw input is pre-processed prior to analysis by an image segmentation and/or labeling algorithm. The pre-processing can include one or more steps, for example, resizing the image(s) to a standard size, converting color image(s) to grayscale, or removing noise from the image(s). In some embodiments, at subsequent stages, the input to the succeeding module is a layer-wise concatenation of the original input or raw input and the output of the prior stage(s) or module(s). For example, a prior output may be the softmax output for a multiclass classifier. Accordingly, subsequent modules are able to take into account the previously inferred outputs to add information for the progressively more difficult problems. In some embodiments, a neural network is used, wherein the neural network comprises a plurality of modules and a plurality of classifiers. Each module can consist of one or more layers of artificial neurons. A classifier can also consist of one or more layers of neurons with the distinction being that the classifier generates an output indicative of a decision or classification of the input (e.g., image or pixel(s)).

An excessive number of difficulty levels may be disadvantageous since it would lead to an excessive number of overall layers to the neural network. Hence, in some embodiments, each level of difficulty contains multiple individual tasks or classes to be segmented. In order to generalize this approach to various application domains, one advantageous approach is to develop and use a computational ontology for describing the various classes to be segmented. In particular, the ontology has rich hierarchical relationships so that classes of similar difficulty can easily be identified. For instance, the ontology identifies all bones as belonging to one difficulty class while all cartilage and all ligaments belong to their own respective difficulty classes.

In some embodiments, the neural network architecture for progressive reasoning comprises skip connections between artificial neuron layers. The skip connections can occur anywhere, for example, across modules and classifiers in different difficulty layers. Although these skip connections are not shown in FIG. 26, various neural network architectures can be used that are consistent with this approach. An advantage of this approach is that previously computed feature maps can be used by subsequent layers to obviate the need for the network to have to re-learn features across these boundaries which is inefficient.

The progressive reasoning architecture disclosed herein can be applied to almost any neural network backbone structure where the specific implementation of each of the module(s) layers and classifier layers can be substituted with almost any other neural network layers.

AI-Assisted Dictation of Findings and/or Measurements, Comparison, and Query

Described herein are systems, software, and methods for facilitating AI-assisted interpretation and reporting of medical images. In some cases, the systems, software, and methods detect user interaction with the image (e.g., mouse movement or eye movement) and verbal actions (e.g., dictation) and generating an AI-assisted finding/measurement based on the combined input. An AI-based image segmentation algorithm as described herein can automatically or semi-automatically detect and label portions (e.g., anatomic regions) of a medical image. The system allows a user who is viewing the segmented image on a display to interact with the image such as by pointing at the image with a mouse cursor (e.g., at a labeled segment). The user can dictate one or more statements corresponding or relating to the image, for example, a medical statement or finding with respect to the portion or segment of the image that the cursor is pointing at. In some instances, the system comprises a microphone or audio detection component for detecting the dictation, and converts it to the corresponding text. The system can combine the inputs (cursor & dictation) to generate an AI-assisted finding/measurement. For example, when a user points the cursor at or looks at the L5 vertebra on an X-ray and verbally states "fracture", the system generates a finding (e.g., a sentence) that is inserted into the medical report for the X-ray image that states the L5 vertebra has a fracture. A non-limiting example of this process is shown in the flow chart in FIG. 1. The flow chart shows the medical image being segmented and labeled using an AI algorithm (e.g., a neural network trained using a machine learning algorithm), which is then visualized for the user. The user's interaction with the image can be detected using point-and-click or eye tracking along with dictation of a phrase, which is converted into a complete phrase or sentence and inserted into a report. These processes can be implemented via a system, subsystem, or module, which can be stand-alone or part of a larger platform or system as disclosed herein.

One advantage of the systems, software, and methods disclosed herein is that AI-assisted medical report generation enables for the faster and more streamlined analysis of medical images and generation of the corresponding medical reports. During the process of reading an exam, radiologists often dictate findings verbatim into a speech to text transcription system, which includes specifying anatomic location. This involves verbally saying the part of the anatomy for which they are dictating and crafting full sentences about the anatomy's finding, which can be time consuming.

Accordingly, the present disclosure incorporates image segmentation and user input/interaction to overcome the time-consuming nature of the conventional dictation process. Specifically, AI-based image segmentation of anatomic regions and redundant inputs (e.g., mouse click, eye tracking) allow radiologists to select a segmented area and speak an abbreviated or shortened phrase, and have the location and clinical context inferred by where they are pointing/looking, resulting in a complete sentence being inserted into the clinical report. The medical image(s) can be automatically segmented into relevant anatomic regions and labeled including coded and/or plain-text descriptions of the anatomy. The segmentation algorithm can be provided the raw input images as well as any available meta-data regarding what part of the body has been scanned. Accordingly, when the radiologist or user points to or looks at the portion of an image that is segmented and labeled and dictates their phrase, the corresponding finding can be automatically incorporated into the report. This allows for computer-findings to be incorporated into the report along with human-findings. For example, the segmentation and label of the portion of the image may be the computer-finding portion of the overall finding, while the human-dictated portion may be the human-finding. As an illustrative example, if a user points or looks at a neuroforamen (labeled C2-C3 foramen by the segmentation/labeling algorithm) on a medical image and says "stenosis", then a finding may be generated that states "neuroforaminal stenosis at the C2-C3 level", thus incorporating both human and computer findings.

In some cases, disclosed herein is AI-assisted dictation of a finding. One use of this information is when the user is dictating a finding at a specific anatomic location. For instance, the finding of "disc bulge at the T1-T2 vertebral level" would normally involve having to explicitly dictate "T1-T2 vertebral level". By using the image segmentation as described above along with either the mouse pointer location in the image or using eye-tracking software to determine the image location, the user would no longer need to dictate the location, and the AI-assisted reporting would only need "disc bulge" to be dictated while either pointing at or looking at the T1-T2 disc. Of course, any finding type could be substituted for "disc bulge".

Figure 2:
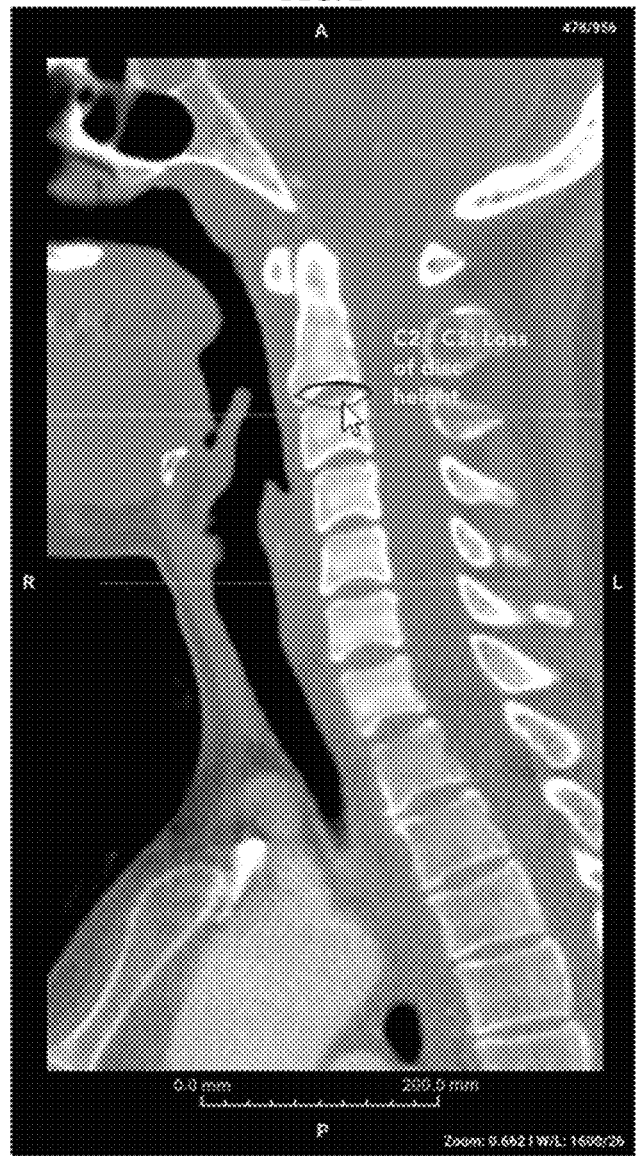
FIG. 2 shows an illustrative example of a medical image of a C2-C3 loss of disc height.

The user's dictation can be converted into the corresponding text to be incorporated into a medical report. The dictation can be literally converted into text verbatim, and alternatively or in combination, the text or dictation can be "translated" or "interpreted" to generate the final text that is incorporated into a report. The system may be configured with an algorithm that converts captured audio into text/words and/or translates or interprets the audio/text/words into a new format or configuration. Accordingly, in some cases, the system comprises an algorithm configured to detect a shorthand or slang from the spoken audio and convert the audio into the long-form or appropriate format (e.g., plain English) for a medical report. For example, a user may speak "compression fracture" (e.g., a human-finding) while pointing the cursor or gazing at a segment of an X-ray image labeled "C5 vertebra" (e.g., a computer-finding), and the system automatically generates a written finding that is incorporated into the medical report for the X-ray image that states, "Compression fracture is seen at the C5 vertebra". FIG. 2 illustrates an example of a medical image with an anatomical portion identified by the encircling line, and a corresponding label "C2-C3: loss of disc height" positioned adjacent to the anatomical portion.

In some cases, disclosed herein is AI-assisted dictation of a measurement. This can be implemented through an automated measurement system. Many of the findings within a typical radiology report are noting the presence of a particular finding at a specific anatomic location with some level of severity. Another common type of finding is a quantitative measurement of some anatomy that is out of the expected range of values. Currently, the user would switch to a measurement tool and then explicitly draw a line segment over the image in order to make the linear measurement. Then, they would dictate the measurement verbatim, for example, "Full-thickness tears of the entire supraspinatus and infraspinatus tendon footprints with the tear defect measuring 4.4 cm medial to lateral×5.2 cm AP". By contrast, the present disclosure enables the user to either point at (without having to explicitly set the start and end points of the line segment) or look at the relevant anatomy and give a command to measure (e.g., a verbal command to "measure this"). Non-limiting examples of commands include auto-measure ("measure this"), comparative case flow ("compare this"), and image query ("what is this?", CADx, CBIR). Accordingly, by using the anatomic segmentation, the AI system would know which portion of the anatomy to measure using the segmented anatomy as the boundaries for diametrically opposed ray casting to make define the line segment from which to make the linear measurement. Then, the AI system can automatically construct the sentence to be inserted into the report. One example in the context of oncological imaging would be to apply the maximal height/width measurements of the RECIST ("Response evaluation criteria in solid tumors") system.

While dictation can be used to command the system, non-verbal commands are available alone or in combination. For example, a user may use the mouse and/or keyboard to point and click on the medical image to select a segment and/or to cause the system to measure the anatomic feature or segment. In some cases, the user can indicate a location on the medical image using a stylus or finger such as in the case of a touchscreen display.

In some embodiments, each piece of anatomy in the system has a tag which describes the type of anatomy. This is a unique identifier for each type of anatomy in the software's ontology. This identifier is what is used to set the anatomic context globally such that all other user actions occur in this context. In some cases, when a user selects (e.g., using the mouse or eye-tracking) a part of the anatomy shown on the image, the user is presented with a list possible clinical findings relevant to that part of the anatomy. In one embodiment, the list comprises possible findings in decreasing order of prevalence without consideration of the imaging appearance for this particular patient. In some cases, the list is curtailed at a user adjustable length (e.g., top 10 findings).

In another embodiment, the list of findings is generated by a computer aided detection/diagnosis module that creates a list of possible findings at that particular region of the image where the inference is specific to this particular patient. A score or probability can be generated for each possible finding and the findings are optionally presented in decreasing order of score or probability. The computer aided detection can be an output generated by an image analysis algorithm. In some embodiments, the output is a predicted or detected feature or pathology that is generated using an image analysis algorithm comprising a neural network architecture configured for progressive reasoning. As an illustrative example, a neural network is made up of a sequence of modules with classifiers that generate input based on an input medical image and the output generated by the previous classifier. In this example, the classifiers of this neural network carry out image segmentation, labeling of the segmented parts of the image, and then identifies pathologies for the labeled segments (e.g., a lesion, stenosis, fracture, etc.) in sequence with the segmentation output being used in combination with the original image by a classifier that performs labeling of the identified image segments, and the classifier identifying pathologies using the labeled image segments and the original image.

In some embodiments, when the user selects a particular finding (e.g., from the list of possible findings), a structured representation of the finding is generated. One possible way of representing this finding is through a knowledge graph that represents various concepts such as the anatomic location and the type of observation. For each location or observation, various modifiers which are also concepts may be associated with it such as sub-anatomic location or severity of the observation. In the knowledge graph, each concept is a node and a directed arc between two nodes denotes a relationship. For instance, "C2-C3 foramen" has_observation "stenosis" and "stenosis" has_severity "mild".

In some embodiments, the structured representation of the imaging finding is converted into natural text for insertion into the report. In some cases, this natural text representation is created by querying a database of previous imaging findings and their structured representation as a knowledge graph. Alternatively or in combination, the natural text representation can be created through a simple set of production rules given the structure of the knowledge graph. In the example from the previous paragraph, a query might return "A mild neuroforaminal stenosis is observed at the C2-3 level" from an existing database of parsed findings while a production rule like "<anatomy> has <severity> <observation>" might return "C2-C3 foramen has mild stenosis."

In some embodiments, disclosed herein is AI-assisted auto-measure function. Currently, linear medical image measurements are made using a digital ruler where the user clicks one point to anchor the ruler and then drags out a line segment such that when they release the mouse button, the ruler is then set and it visually displays the length. However, this interaction can be inaccurate, especially if measuring small objects such as a suspected tumor at low image magnification where the object extends only a few screen pixels, thereby making the measured lengths highly quantized. This also adds to the tediousness of the task since the user must control the mouse with very high precision.

In some embodiments, the auto-measure tool is semi-manual, in which once the measurement tool is activated, a magnified version of the image near the mouse pointer is overlaid on the non-magnified image and the mouse movements in manipulating the ruler endpoints is done in the magnified image in order to avoid the problem described above. Additionally, assistance is provided to ensure that the ruler endpoint is placed as close to images in the image as possible. This is accomplished by computing an edge potential map of the image, I, which can be calculated using the formula shown in FIG. 28A. The image gradient can be computed using convolution with derivative of Gaussian kernels, G, as used in the well-known Canny edge detector (Canny, IEEE TPAMI 1986). The edge potential map, g, can be computed using any function that varies inversely with image gradient magnitude such as the formula shown in FIG. 28B.

Figures 28A, 28B, 28C:
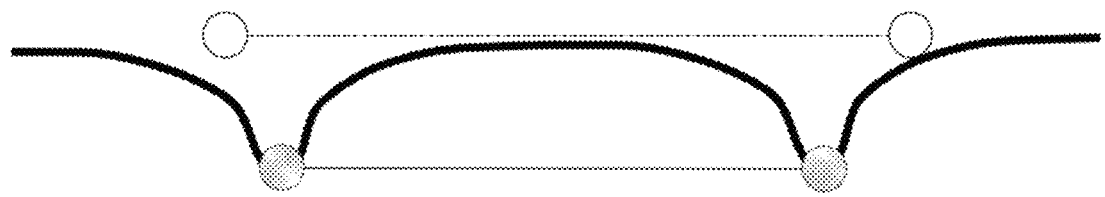
FIG. 28A shows an example of a formula for calculating an edge potential map of an image.
FIG. 28B shows an example of a formula or function that varies inversely with image gradient magnitude for calculating an edge potential map.
FIG. 28C shows an illustrative example of calculated endpoints.

In some embodiments, from the original position of the placed ruler endpoint, the desired endpoints are computed by performing a line search along the line defined by the two ruler endpoints. The edge potential map can be used to allow the ruler endpoints to fall into the local minimum, at which point they become the desired endpoints. Thus, as long as the ruler endpoints are initially placed in proximity to an image edge, they can automatically find the edge and stick to it. FIG. 28C shows an illustrative example of calculated endpoints.

In some embodiments, the auto-measure tool is fully automated, in which the user only needs to define a single point on the image to initiate the tool. Linear measurements can be made at numerous angles and the user may choose either the single longest for a 1D measurement, or the longest measurement and the measurement(s) perpendicular to it for a 2D or 3D measurement. This automated measurement can be defined by a mouse click (e.g., including trackball click, touchpad click, or any other equivalent device) or by other computer input devices such as, for example, an eye-tracking device.

The automatic measurement can be performed based on the initially placed point. As an illustrative example, the initially placed point is placed generally near the center of the object, and a star shaped pattern is used to perform directional line searches at various angles (e.g., every 45 degrees). In this example, each search is terminated when a local minimum of sufficient depth (e.g., <50% of the edge potential at the initial point) is reached.

For both the semi-manual and the fully automated measurement methods, the user may adjust the measurement in an automated fashion by either using voice input to increase/decrease the desired endpoints (e.g., saying "larger" or "smaller"). Alternatively or in combination, the mouse scroll wheel (or some other suitable user input) can be used for similar effect.

In some embodiments, disclosed herein is AI-assisted comparison to prior study, which can be referred to as comparative case flow. The present systems, software, and methods can allow a user to make comparisons of the specific anatomy being queried (by pointing at or looking at) between the current imaging study and any available prior studies. Currently, if prior study(s) are available, the user must manually find the same anatomy in both scans and then create findings or measurements in the current and prior studies in order to make a comparison. Accordingly, it would be desirable to have linked scrolling such that scrolling the image slices in the current image stack causes the prior image stack to scroll while preserving the anatomic location between the two image stacks. Current implementations use image to image registrations to perform this task. Image registration consists of determining a transformation of one image's coordinate system to another image's coordinate system such that the same anatomy will have the same coordinates in the fixed image as in the moving image. Rigid transforms (translation and rotation only) or non-rigid transforms may be used to accomplish this with the latter requiring significant computational resources.

Figures 29A, 29B:
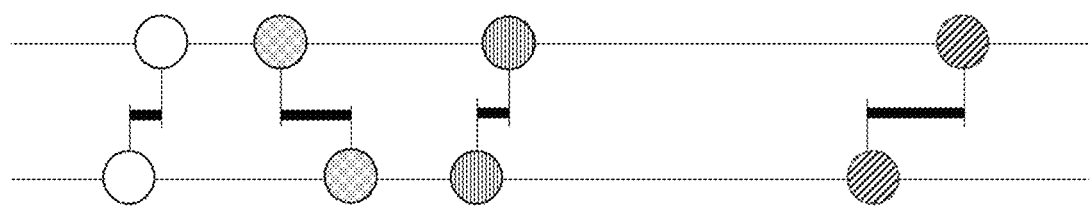
FIG. 29A shows a formula that can compute the squared sum, D, of the distances between matching pairs of anatomic regions.
FIG. 29B shows an illustrative example of an image comparison approach with four anatomic region centroids (circles) computed and projected onto the lines perpendicular to each image stack (thin horizontal lines) for both fixed (above) and moving (below) image stacks.

Accordingly, disclosed herein are systems, methods, and software for AI-assisted comparison to prior study or comparative case flow that utilize anatomic segmentation and labeling. For both the current and prior image stacks, the segmentation and labeling of the relevant anatomy can be computed. Compared to the general case of 3D to 3D image registration, a simplifying assumption can be made such that the registration is 1D where given an image in one image stack, the nearest matching image in the other image stack is desired without full 3D rotation. In some cases, the current image in the fixed image stack is selected by the user, and the requirement is to find the image in the moving image stack that is closest in matching the anatomy of the fixed image. In order to consider this as a 1D problem, centroid of each 3D anatomic labeled region can be computed and then projected onto the line perpendicular to the image stack. This is done for both fixed and moving image stacks. The distances between matching pairs of anatomic regions, di, are computed and their squared sum, D, can be computed according to the formula shown in FIG. 29A. This sum can be minimized in order to find the optimal 1D translation between the fixed image and the moving image. FIG. 29B shows an illustrative example of this approach with four anatomic region centroids (circles) computed and projected onto the lines perpendicular to each image stack (thin horizontal lines) for both fixed (above) and moving (below) image stacks. The pairwise distances are shown in thick horizontal lines.

Accordingly, by using the anatomic segmentation, the user can give the command "compare this" and the AI system would determine the matching anatomic location across current and prior study(s) and then optionally provide a list of the finding/measurement for each study. For quantitative measurements, the system can make a quantitative comparison (for instance, percent change) and generate the text and insert into the report automatically (e.g., a computer-finding that is a quantitative measurement).

In some embodiments, disclosed herein is AI-assisted query, which can be referred to as an image query function. The present systems, software, and methods allow for AI-assisted querying of specific regions of the image. If a user (e.g., radiologist) saw an area of the image with a possible abnormality, he/she can simply point at or look at the region and say, "what's this?", and be presented with a list of possible findings associated with that area of the image (e.g., computer-findings of predicted pathologies for a segmented & labeled anatomic part). The possible findings can be generated using an AI vision system or module comprising one or more algorithms or models for image analysis. In some embodiments, the AI-assisted query function is configured to find a broad spectrum of imaging abnormality categories. For example, in MRI of the spine, there may be approximately 50 different abnormality categories that can be observed, and detection of these abnormality categories can be made using a variety of different machine learning architectures. In some embodiments, specific models are generated for each abnormality category. For example, one approach would be to build and train 50 different detection models for the 50 different abnormality categories. In some embodiments, a single multi-task model or algorithm is generated to detect the various abnormality categories. For example, a single model can be trained to detect 50 different types of abnormalities using a multi-task learning (MTL) approach. In some embodiments, a combination of the multiple individual models and the single multi-task model approaches are used (e.g., multi-task model for related categories and multiple single models for unrelated categories). Additional descriptors such as severity may also be inferred by the model for each candidate abnormality (e.g., a lesion detected in the spine may have a corresponding severity score or indicator).

The image query function disclosed herein enables an image to be queried to obtain the results of the multiple abnormality category detections. At any point during image interpretation, the user may initiate a query using a designated mouse button, a keyboard hotkey, voice command ("What's this?"), or any other suitable user input. At the time of query, the image position can be defined either using the mouse or by other computer input devices such as an eye-tracking device. In some embodiments, when a candidate abnormality category (e.g., a candidate lesion) is close enough to the designated image location and has a probability or score above a given threshold, this result is presented to the user and a full text sentence describing this finding is generated (e.g., a computer-finding). In some cases, the user will then be prompted to either accept or reject the sentence into the findings section of the medical report.

Accordingly, an AI vision system or module as disclosed herein can comprise one or more algorithms or models that provide for numerous possible findings that could be returned at any given point in the image. For example, a given point in the image would have a map of probabilities (or probability-like quantities) for each possible finding. Given the point specified by the user, the AI system can return a rank-ordered list of possible findings in decreasing order. The list may be truncated at a given probability level or length. With a verbal "yes" or "no" command or by clicking on the appropriate button, the user is able to choose whether or not the AI system should automatically generate the text for this finding and insert it into the report. In some cases, the systems, software, and methods disclosed herein are augmented with content-based image retrieval (CBIR) functionality such that the region being queried can be used to find similar images within a pre-populated database with corresponding findings or diagnoses. Then, the user would be able to determine by visual similarity which of the CBIR results matches the current query and as above, the report text would be automatically generated and inserted into the report. For example, the retrieval of similar images labeled with the true finding may help the user decide what the finding under consideration actually is.

Alternatively or in combination with mouse cursor detection, eye-tracking can be used to obtain input indicative of one or more gaze fixation points. This allows user interaction with the image to be detected without requiring the user to manipulate a mouse, trackpad, keyword, or other physical input device (e.g., a finger or stylus on a touchscreen). The system can include eye-tracking one or more device(s) for measuring eye position and/or eye movement. In some cases, the system utilizes an eye tracking algorithm to extrapolate the user's gaze fixation point(s) on a medical image. The image may be displayed on a computer screen or display, or alternatively, on a projected image. The eye tracking device can be a camera or other optical sensor. In some cases, the system comprises a light emitting device that projects light (e.g., infrared) onto the eye(s) of a user. An optical sensor then detects the light that is reflected off the eye(s). The pattern of reflected light detected by the optical sensor can be used to calculate the corresponding gaze fixation point. The light can be a near-infrared (IR) light, which has the advantage of not being invisible to human eyes. A video-based eye tracking system can take an image of the corneal reflection of the reflected light and the pupil. The corneal reflection and pupil can be used as features to determine the eye position and/or movement for purposes of identifying the gaze fixation point. This system can be setup on a display or monitor, for example, the light emitting device and the optical sensor both built into or attached to the display.

In some cases, the eye-tracking system is configured to detect user commands based on eye tracking input. User commands can include various input commands that are available using conventional input devices such as, for example, a mouse, keyboard, trackpad, joystick, controller, or stylus. Non-limiting examples of user commands that can be conveyed using eye tracking input include selection or de-selection (e.g., of a region or feature on a medical image), scrolling, magnification (e.g., zooming in, zooming out), switching between images, and opening or closing an image. The eye tracking input can be pre-programmed to correspond to specific commands. Alternatively or in combination, one or more eye tracking input can be customized to correspond to commands specified by a user. The eye tracking input can include one or more actions such as blinking (e.g., blinking to freeze the indicator of gaze fixation point on the screen), number of blinks (e.g., multiple blinks in quick succession), and gazing in specific directions. For example, a user may gaze in a particular direction or towards the edge of the medical image to scroll in that direction. The user may need to maintain the gaze for a minimum duration (e.g., 0.5 s, 1 s, 2 s, etc.) to initiate the scrolling or other command. Similarly, the system can be configured to require the blink be maintained for a minimum duration in order to effectuate the user command.

Accordingly, the systems, software, and methods disclosed herein enable users to point their mouse or use eye-tracking software/hardware to identify a feature or segment on a medical image and speak an abbreviated phrase, and have the location and clinical context inferred by where they are pointing/looking, resulting in a complete sentence being inserted into the clinical report. Thus, the "point" and/or "look" mechanisms can be used to initiate clinical measurements with the location being inferred by mouse or eye location using AI-based segmentation.

Bi-Directional Dynamic Linking of Findings

Described herein are systems, software, and methods for facilitating AI-assisted interpretation and reporting of medical images. In some cases, the systems, software, and methods provide bi-directional dynamic linking of findings in a report. Findings dictated by users can include an image/area/volume in which they are visualized (e.g., axial slice 13). These images are often referred to as "key images" or "bookmarks" and may be noted in the report in order to allow for referring physicians (or radiologists performing future follow up exams) to more easily find the lesion or region being discussed. The task of diagnostic interpretation of a medical image may be abstracted to finding image regions containing findings of interest and then creating textual descriptions of the finding in the report. Currently, if the user is unaided in interpretation, the information linking the image region of interest to the finding text is usually implicitly given by the anatomic location provided in the text of the report. Occasionally, the user may make note of the location of the finding by specifying a key image location in the report (e.g., axial slice 13). However, this only specifies one out of three dimensions if the image is volumetric. These processes can be implemented via a system, subsystem, or module, which can be stand-alone or part of a larger platform or system as disclosed herein.

Figure 3:
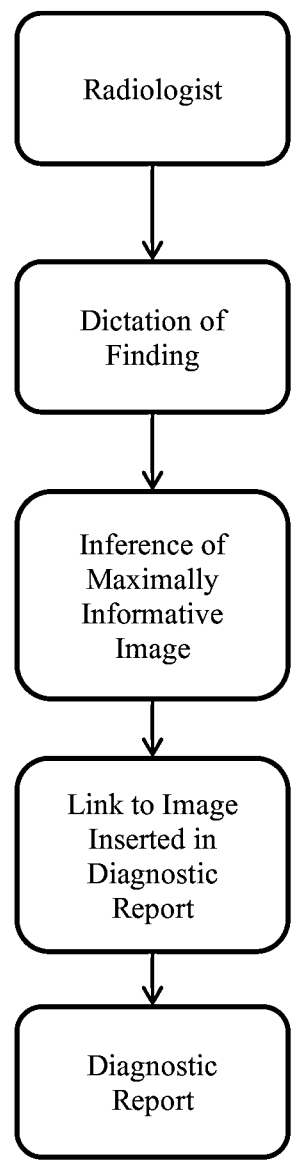
FIG. 3 shows a flow chart illustrating a non-limiting example of a process for generating a linked diagnostic report.
Figure 4:
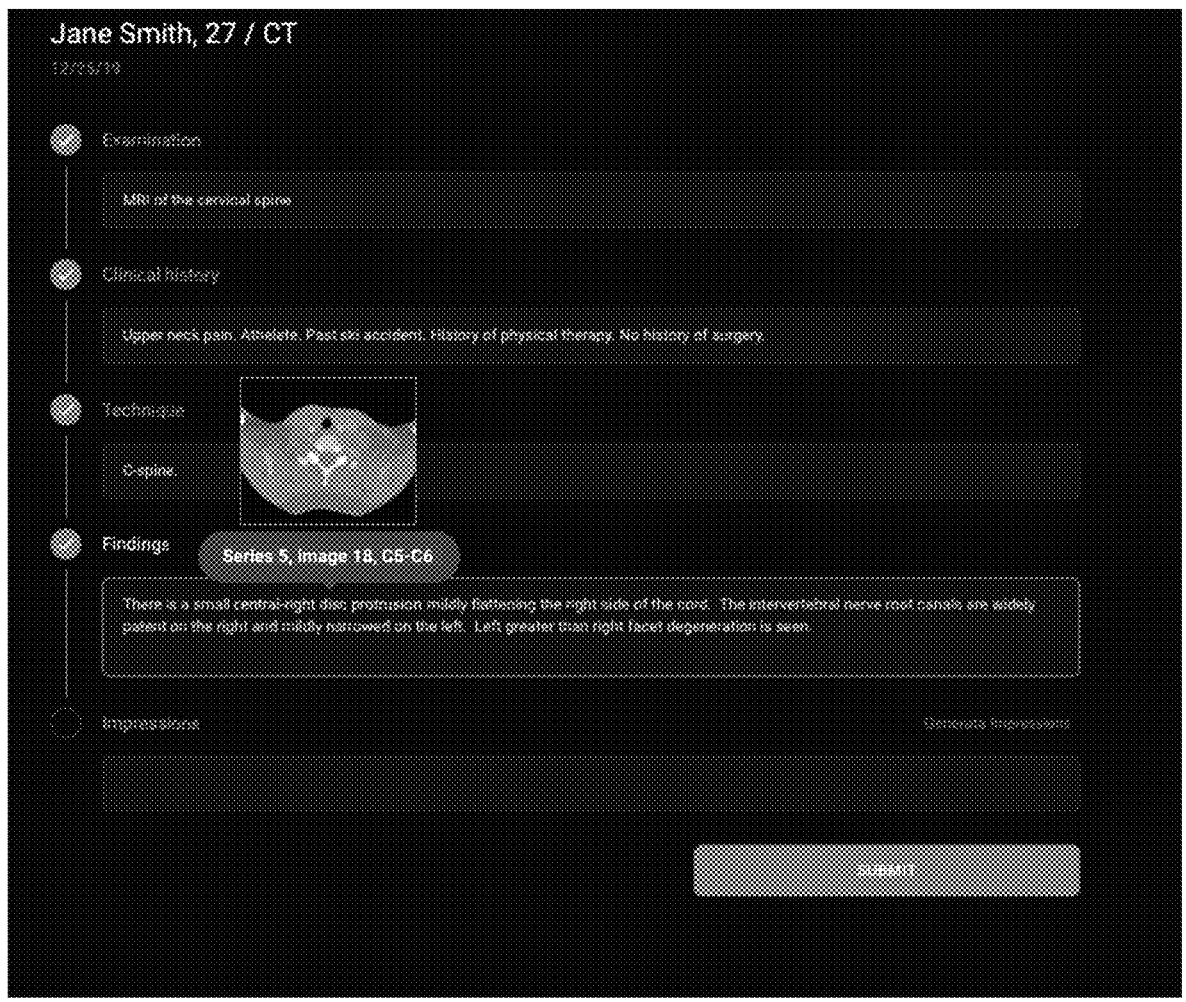
FIG. 4 shows an illustrative example of a finding with a linked inferred maximally informative image.

Accordingly, disclosed herein are systems, software, and methods for automatically inferring the (maximally) informative image and creating a link to it in the report based on the viewing and dictation context. The viewing and dictation context used to infer the informative image can include one or more of eye tracking, position of mouse, image on screen, output of AI algorithm, the image (e.g., X-Ray, CT, MRI, etc.). During diagnostic report creation, the user may have two primary modes of viewing the data, which are the input images and the output text. This subsystem makes the linkages between input image regions of interest and output findings text explicit. Recording this linkage internally within the AI output comprises recording the region of interest (e.g., a contour or bounding box) within the metadata for each AI-generated finding. This subsystem makes this linking evident to the user, which may be the user during interpretation, a subsequent user during a future follow-up exam, the referring physician, or even the patient. When the user selects an image region of interest (e.g., by mousing over or moving a mouse to a region or selecting from a list), the corresponding AI-generated text in the report can be illuminated or highlighted in a distinctive manner (e.g., text highlighted with a distinct or contrasting background color). Similarly, when the user selects a finding text in the report (e.g., by mousing over the sentence in the report or selecting from a list), the corresponding image region of interest is highlighted in a distinctive manner (e.g., the region boundary is drawn and/or the region interior is given a distinct hue). In some cases, when selection is chosen by hovering the mouse over images or text, the selection can change dynamically as the mouse pointer is moved, allowing for fast interaction not requiring any mouse clicks. A flow chart showing a non-limiting example of this process is shown in FIG. 3. An illustrative example of the inferred maximally informative image with associated link is shown in FIG. 4.

In some cases, multi-selection capability is allowed. For example, within the image, multiple image regions of interest may be selected through a lasso type tool (e.g., rectangular or free-form) and then, all the corresponding findings selected by the tool can be highlighted. If desired, all of those findings may be deleted in a single action if multi-selected. Similarly, multiple text findings may be selected by highlighting multiple regions of text (either through one long contiguous selection or through shift-click multiple text multiple selection) and then, all of the corresponding image regions of interest would be multi-selected. In some cases, multi-selection deletion is allowed.

AI Finding Display and Interaction

Figure 5:
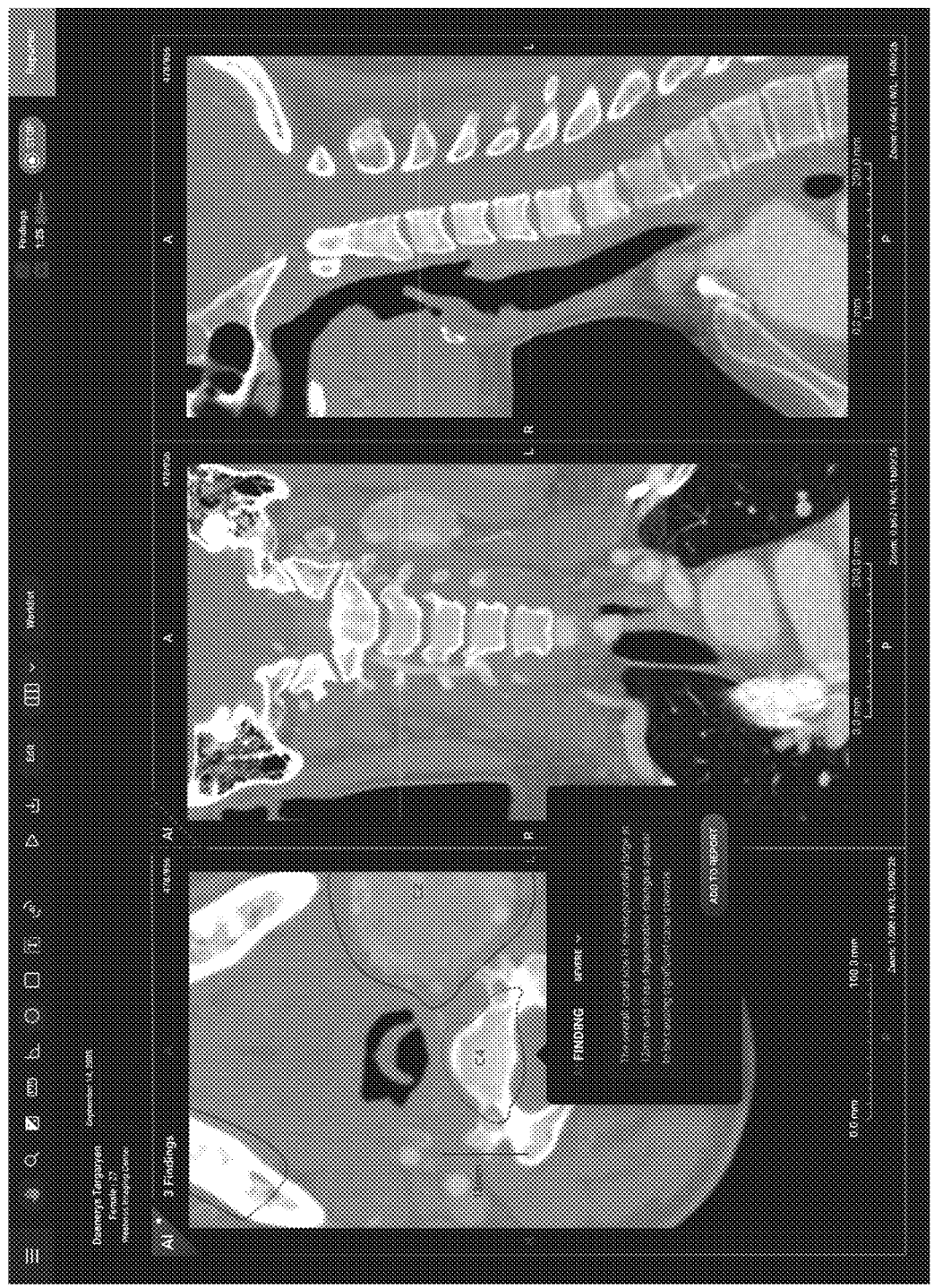
FIG. 5 shows an illustrative example of a medical image with a finding presented for a user to confirm for insertion into the medical report.

Described herein are systems, software, and methods for facilitating AI-assisted interpretation and reporting of medical images. In some cases, the systems, software, and methods comprise displaying and interacting with AI-generated findings. A list of potential findings or lesions can be presented to the user for further review to either accept or reject. The scope of this subsystem is the visual presentation of AI findings to the user as well as the interactions need to accept, edit, or reject each finding. As an example, the user or radiologists is presented with a card overlay, on top of any AI findings/diagnoses, with the associated medical text that are suggested for insertion into the diagnostic report. The user can have the ability to edit this text by voice, keyboard, or other suitable input device. FIG. 5 shows an example of a medical image with a finding presented for a user to confirm for insertion into the medical report. The finding states, "The overall canal size is developmentally large at 12 mm, and these degenerate changes appear to be causing significant canal stenosis" and is overlaid on the medical image with the corresponding segment on the image labeled "C4" with the 12 mm measurement displayed. These processes can be implemented via a system, subsystem, or module, which can be stand-alone or part of a larger platform or system as disclosed herein.

In some cases, the systems, software, and methods provide AI for finding dimensionality of an output. The AI system outputs may be grouped based on the dimensionality of the image region of interest that precipitated the finding. Pointwise findings are 0-dimensional and can arise from either anatomic landmarks (e.g., xyphoid) or may be the centroid or center of mass of a region where the boundaries may be ill-defined (e.g., an inflamed joint). Linear findings are 1-dimensional and can arise from either a pair of points that define a distance measurement (e.g., vertebral disc thickness) or from a centerline structure for a tubular structure (e.g., central vertebral canal). Planar findings are 2-dimensional and may arise from 3D regions within a 2D projected image (e.g., mediastinum in a chest x-ray) or arise from a non-manifold region of space (e.g., laryngeal inlet). Volumetric findings are 3-dimensional and may arise from 3D regions of anatomy (e.g., liver). Higher dimensional time-varying findings are also possible for 4D (and higher) datasets.

Figure 20:
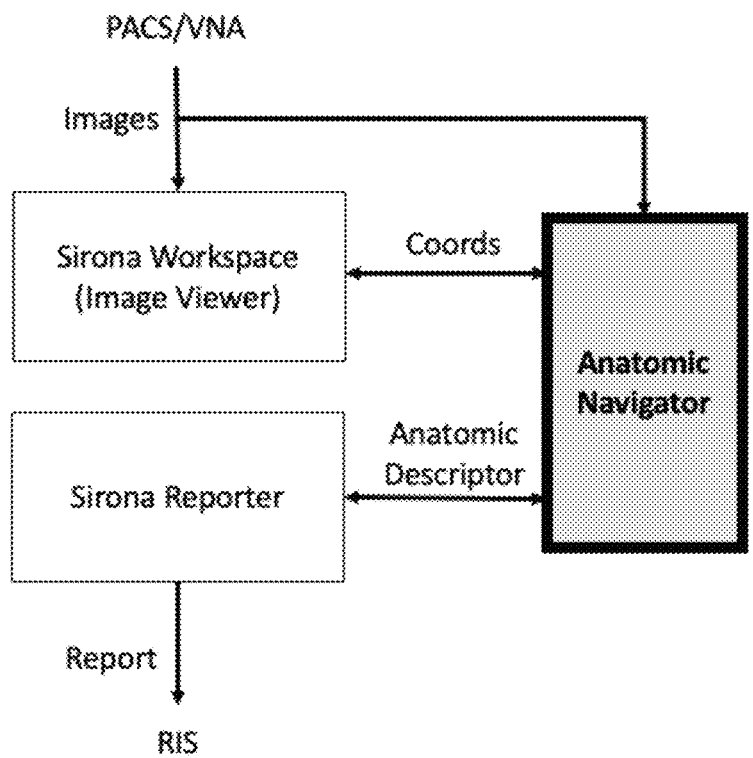
FIG. 20 shows a diagram of the workspace image viewer module, the anatomic navigator module, and the reporter module.

Described herein are systems, software, and methods that enable navigation of images for facilitating AI-assisted interpretation and reporting of medical images (can be referred to as an "anatomic navigator" or "anatomic navigator module"). In some cases, the anatomic navigator is a user interface enhancement configured to be used during reporting of radiological imaging findings, for example, MRI of the adult spine. The anatomic navigator can be used as an accessory in combination with a workspace image viewer module and can enable communication with a reporter module for radiological report generation. The workspace image viewer can display medical images, including multiple image viewports for 2D multiplanar reconstructions or 3D volume rendering, image scrolling/panning/zooming, window/level, user-generated image annotations, or any combination thereof. The reporter module can perform functions including report templates and macros, speech-to-text input, and dictaphone-based template field navigation. In some cases, the workspace image viewer and reporter are configured to operate without the anatomic navigator, with the image viewer and reporter working independently. FIG. 20 provides an illustrative diagram showing the relationship between the workspace image viewer module, the anatomic navigator module, and the reporter module.

In some cases, when enabled, the anatomic navigator can keep the image viewer and the reporter in synchrony using one of several interactions, in order to decrease errors and increase efficiency. For example, the user can perform one or more of the following: (1) select anatomic regions in images to navigate through report template fields, (2) select report template fields to navigate images, or (3) select anatomic regions by voice to navigate through both images and reports.

1) The user selects an anatomic region (e.g., L2-L3 intervertebral disc) in the image viewport. While moving the mouse pointer over an anatomic region, a translucent colored boundary with text label (e.g., "L2-L3") is dynamically displayed for visual feedback in the image viewport. When the mouse is clicked on the anatomic region, the anatomic navigator places the reporter text input cursor into the matching template field (e.g., "L2-L3:" field). Thus, the reporter text input cursor marks the point of insertion for which the new text is created in the medical report.
2) The user can move the reporter text input cursor to the desired template field using the next/previous buttons on the dictaphone or the mouse. As above, a translucent colored boundary and text label are shown for visual feedback. The anatomic navigator scrolls, pans, and zooms the image viewports to display the L2-L3 intervertebral disc and its surroundings.
3) The user can say "jump to L2-L3", for instance, and both the viewer and reporter are updated as described in 1) and 2) above.

As used herein, "anatomic descriptors" refer to the enumerated codes used to represent each of the anatomic regions, for example, that the user can select in an image, select in a report template, or say as a jump-to command. The set of anatomic descriptors includes normal anatomic structures expected in all subjects. In some cases, the set of anatomic descriptors does not include any type of pathological descriptors. A non-limiting list of anatomic descriptors is shown in Table 1.

TABLE 1

Anatomic descriptors used by anatomic navigator for the spine. For an imaging study of any given spine region, there are usually a few vertebrae and discs from adjacent regions which are in the image field of view and also labeled. Vertebrae, discs, and spinal cord are represented as a volumetric image region whereas foramen, facet joints, and conus medullaris are represented small spherical regions about a single point. L = left, R = right.

| Spinal Region | Anatomic Descriptors | | | |
| --- | --- | --- | --- | --- |
| | Vertebrae | Discs | Per-disc level | Other |
| Cervical | C1 through C7 | C1-C2 through C7-T1 | L/R Foramen L/R Facet Joint | Spinal Cord |
| Thoracic | T1 through T12 | T1-T2 through T12-L1 | L/R Foramen L/R Facet Joint | Spinal Cord |
| Lumbar | L1 through L5, S1 | L1-L2 through L5-S1 | L/R Foramen L/R Facet Joint | Spinal Cord, Conus Medullaris |

In some cases, images are pushed from the picture archive and communication software (PACS)/vendor neutral archive (VNA) to the anatomic navigator to pre-compute image segmentation and labels (see Table 1). In run-time, mouse clicks in an image viewport can be sent as 3D coordinates to the anatomic navigator, which may then look up the corresponding anatomic descriptor and send the descriptor to the reporter. When a report template field is selected, that anatomic descriptor can be sent to the anatomic navigator which determines a padded bounding box for that corresponding image region, which can be used to scroll, pan, and zoom the image viewports.

Figure 21:
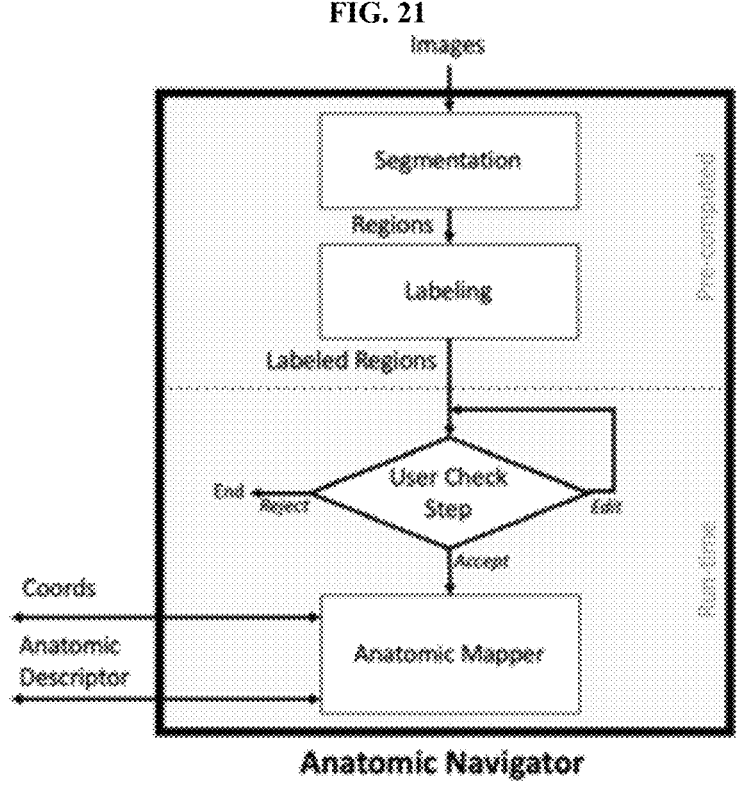
FIG. 21 shows a diagram of an anatomic navigator module with a segmentation module, a labeling module, a user check step module, and an anatomic mapper module.

The anatomic navigator module can include one or more component modules, for example, a segmentation module, a labeling module, a user check step module, and/or anatomic mapper module. FIG. 21 shows a diagram of these modules. The segmentation module can perform image segmentation on one or more medical images, while the labeling module can label segmented features within the image. The segmentation and labeling functions can be carried out as described in the present disclosure, including in the "AI-Assisted Image Segmentation and Labeling" section.

In some cases, the systems, software, and methods provide one or more modes of navigation of AI findings. The various modes of navigation can be provided through a "navigation module" or "anatomic mapper module". For the one or more modes of navigation, the anatomic mapper module may take as input the labeled image regions accepted by the user. Multiple modes of navigation can be combined to provide more than one way for a user to navigate AI findings (e.g., any combination of the modes disclosed herein).

In one mode of navigation, the system renders geometric representations of the image finding on top of tomographic images or embedding within a volumetric rendering allows the navigation of the images in usual manner (e.g., scrolling through slices in cine mode) while presenting the findings. Further information about a finding may be brought forth by hovering the mouse pointer over the region which brings up a card overlay as shown below.

Disclosed herein is a second mode of navigation presenting the user with a list of CAD findings, often in order of descending confidence or probability or in anatomic order (e.g., superior to inferior). When a finding is selected, the image display jumps to the coordinates of the finding. The user then makes the decision to accept it and add the generated text to the report or to reject it.

Disclosed herein is a third mode of navigation for reviewing the already generated report text. By selecting a sentence within the report, the image display automatically navigates to the correct coordinates showing the region within the image. In some embodiments, the user is able to select a report template field to convert the anatomic descriptor for that field into a bounding box. For example, a user selects a report template field and the anatomic descriptor for that field is converted into a padded bounding box as follows. A tight bounding box for that pixel label in the labeled segmentation map is computed as the min/max x-y-z bounds and, in order to provide the context of surrounding anatomy, an extra 50% padding is added to the bounding box in all directions. The image viewports are scrolled, panned, and zoomed to fit this bounding box. Next, each image viewport is scrolled and panned so that the bounding box center is at the center of the image viewport. The maximum zoom is then set that fully includes each padded bounding box in each image viewport.

In order to reduce the amount of "look away" back to the reporter window, visual feedback of the anatomic descriptor can be provided in real time. For example, as the mouse is moved across an image viewport, anatomic descriptors are looked up and the corresponding text is displayed as an annotation in the image viewport. Additionally or in combination, the geometry of the labeled region is displayed with a translucent colored boundary.

Disclosed herein is a fourth mode of navigation for selecting or interacting with the image in order to input or incorporate reporter text corresponding to an anatomic descriptor. As an example, the user clicks on the image and the 3D coordinates (e.g., in DICOM Reference Coordinates System within a given DICOM Frame of Reference) are mapped to an anatomic descriptor by a direct pixel lookup in the labeled segmentation map. The reporter text input cursor is then placed in the field corresponding to that descriptor. If the result is a background label, a catch-all template field (e.g., "Additional Information:") may be selected.

As used herein, the "labeled segmentation map" refers to the overlay on top of the medical image. The labeled segmentation map may have multiple classes to correspond to multiple anatomic regions in the image. In some embodiments, the labeled segmentation map is an array of pixels with one-to-one correspondence to image pixels. The value of the segmentation map can be in one of two forms. In "one hot encoding", the segmentation pixel value is a non-negative integer where each binary digit (bit) represents a different class. In "index mode", the integer value of the pixel is a number from 1-N where N is the number of classes.

Disclosed herein is a fifth mode of interaction for providing the anatomic descriptor through speech-to-text. The corresponding template field is selected, the image viewports are scrolled, panned, and zoomed appropriately, and visual feedback of the image region is provided.

In some cases, the systems, software, and methods allow adjustment of the conspicuity of the AI findings such as, for example, opacity of findings overlaid on the image. For example, users may have a range of preferences for how conspicuous the AI findings should be during their review of images for interpretation. On the one hand, users such as radiologists may wish to have very minimal intrusion of AI findings during review and thus, the various overlaid renderings of findings graphics and/or text would have very low opacity values. Optionally, the user can toggle the display of AI findings on/off with a single keyboard or mouse action (or other UI or input action such as, for example, a gesture on a touchscreen). On the other hand, other users may wish to have more prominent AI findings displayed so as to not miss any suggested findings in which case the opacity of the rendered findings would be higher. Accordingly, the system allows the user to continuously vary the opacity of the AI findings in addition to being able to toggle them on/off.

Figure 6:
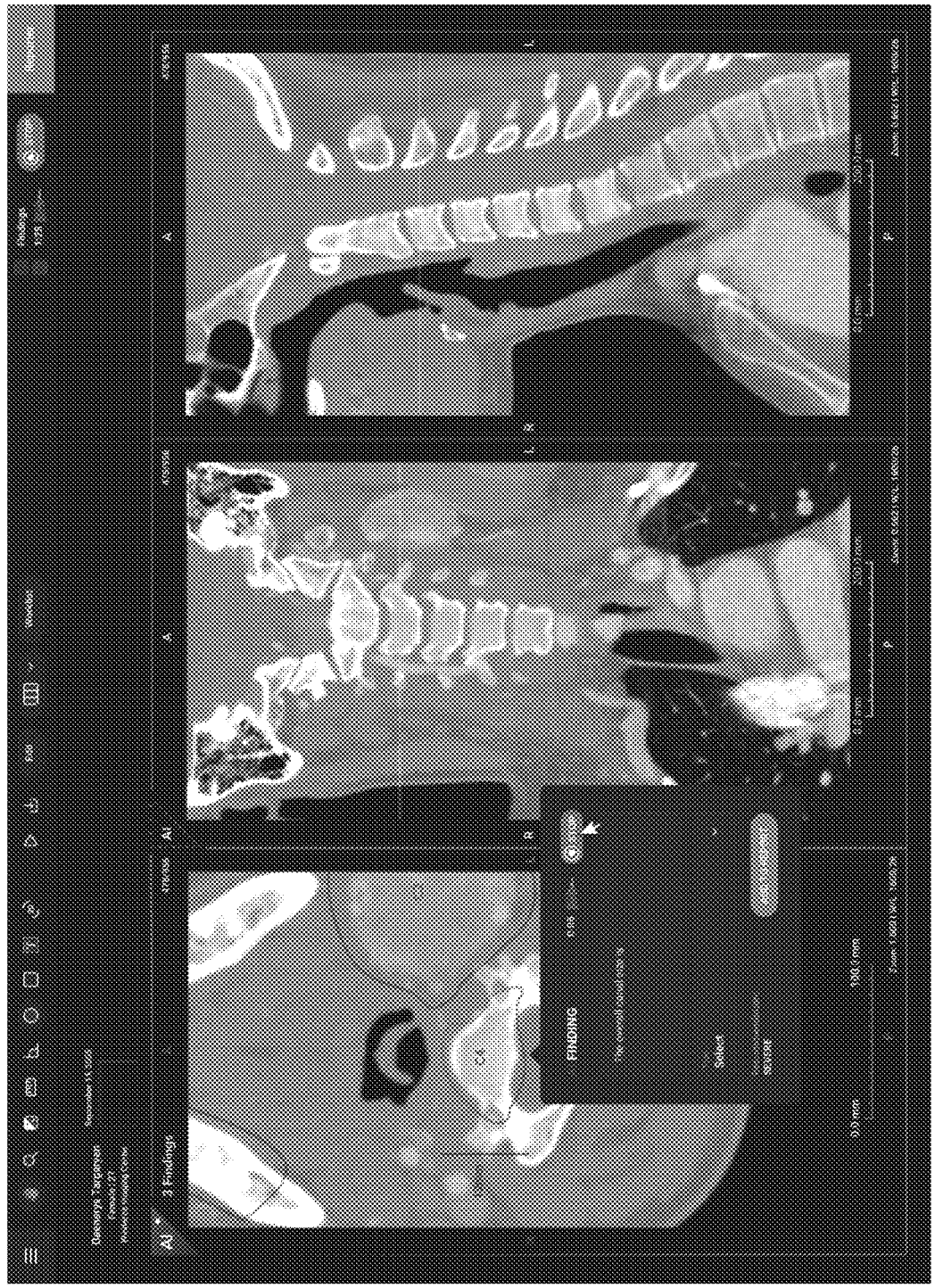
FIG. 6 shows an illustrative example of a medical image with a window for controlling the recording of user dictation to generate an AI-assisted finding.
Figure 7:
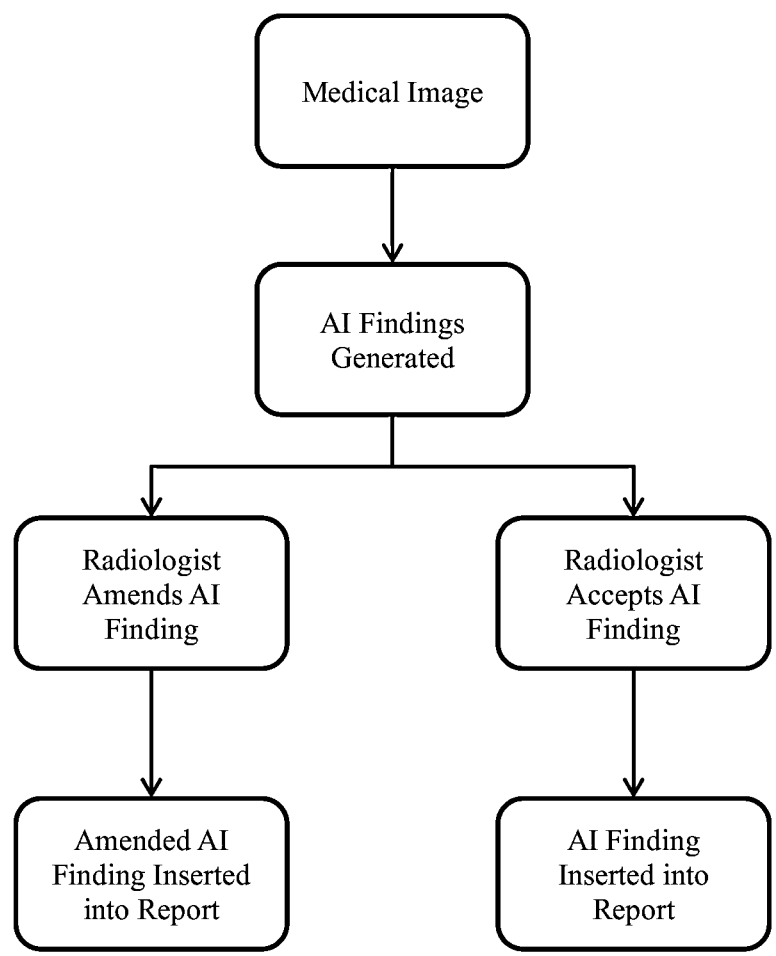
FIG. 7 shows a flow chart illustrating a non-limiting example of a process for a user to accept or amend an AI-assisted finding.

In some cases, the systems, software, and methods disclosed herein allow user interactions with AI findings. Due to the potentially large number of AI findings, the ability to quickly accept, edit, or reject them is of paramount importance in providing an efficient report generation process. Accordingly, the system allows a user to accept or reject a finding by providing a command using any of the following: (1) use keyboard, (2) use buttons on the user interface, (3) use voice by saying "yes" or "no" to provide a fast mono-syllabic option, or (4) a hand gesture recognition system. In order to edit a finding, the user may select the text they wish edit and either use the keyboard or voice dictation to replace certain text. For example, a user may say "jump to" an anatomic region, which causes the cursor to be placed into the matching field, while the image(s) are scrolled, panned, and/or zoomed to center on the anatomic region. Other input methods are also compatible with this process. FIG. 6 shows a screenshot of a medical image with a window for controlling the recording of user dictation to generate an AI-assisted finding. A flow chart illustrating a non-limiting example of the process for a user to accept or amend the AI-assisted finding is shown in FIG. 7.

Tracking and Analyzing AI Assistance

Described herein are systems, software, and methods for facilitating AI-assisted interpretation and reporting of medical images. In some cases, the systems, software, and methods provide tracking and analyzing the AI assistance. In some cases, the system only applies charges for AI findings that the user agrees with and that are entered into the report. In some instances, the system comprises an algorithm for determining congruence or discordance between the AI generated findings and findings dictated by the user. This congruence can be provided as an indicator, rating, or score that the user may consider in accepting or rejecting/amending the AI generated findings. For example, the system may utilize a combination of inputs to generate a finding, and then calculates a congruence/discordance estimate (e.g., an estimated percentage congruence) between the user's dictation and the finding. In some cases, the system utilizes natural language processing in determining the congruence/discordance. These processes can be implemented via a system, subsystem, or module, which can be stand-alone or part of a larger platform or system as disclosed herein.

Figure 8:
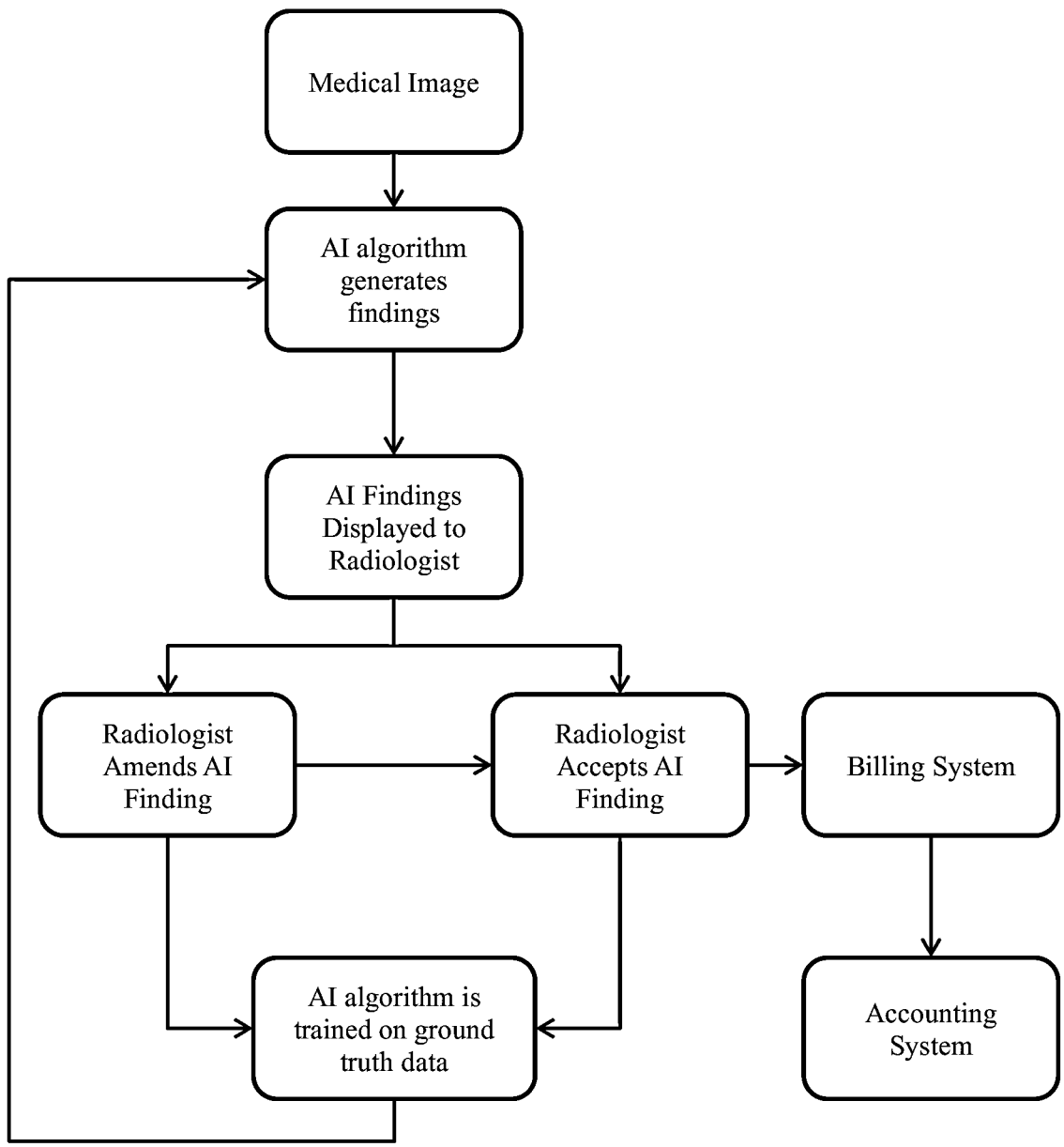
FIG. 8 shows a flow chart illustrating a non-limiting example of a process for analysis of a medical image including feedback loop for improving the AI algorithm.

In order to monitor and improve the performance of the machine learning-based computer vision algorithms and NLP algorithms and systems, the computational system can be tied to a user interface system allowing for active learning. Active learning is a process whereby ground-truth user interaction data is fed back into the algorithms' training set, helping the AI algorithm to learn from data gathered in the real world reflecting the algorithms' performance "in the wild." Accordingly, described here is system for gathering that ground truth feedback from users, and well as an NLP-based system which detects incongruence in inconsistency between a user's explicit interaction with the outputs of the AI models (through the described UI components) and the words they dictate into the diagnostic report. This system ensures that the highest-fidelity ground truth data is fed back into the algorithms for training. A non-limiting flow chart of this process is illustrated in FIG. 8. The flow chart shows the medical image being analyzed by the AI algorithm to generate findings (e.g., AI-assisted findings) for insertion into a medical report. Next, the AI findings are displayed to the user such as a radiologist who can choose to amend or accept the finding. Both decisions provide ground truth data that can be used to further train the algorithm to improve future performance. The amended finding may then be accepted. Once the finding has been accepted, the billing system may then accept the charge corresponding to the finding.

Communications Hub

Described herein are systems, software, and methods for facilitating AI-assisted interpretation and reporting of medical images. In some cases, the systems, software, and methods provide a communications hub for users such as radiologists. In some cases, the system allows queuing of communications from various channels to reduce interruptions during interpretation. Radiologists are often distracted by inbound phone calls from referring physicians, staff members, and other stakeholders in the patient's episode of care. By intelligently routing their phone calls through a VoIP system, time and context-switches can be saved by holding calls until the user is finished reading their current case. The value of minimizing interruptions has been demonstrated by the University of Iowa. The group of 10 radiologists affiliated with this university hired an assistant to hold phone calls until the radiologist was done reading his/her current case, and saved the group $600,000 in time and context-switching per year. Accordingly, the systems, software, and methods disclosed herein provide further improvement upon this process by automating the communications queue without requiring human assistance. These processes can be implemented via a system, subsystem, or module, which can be stand-alone or part of a larger platform or system as disclosed herein.

In order to effectively manage interruptions of the user during image interpretation, the described system can route all communication channels through a single control system. The channels of communication include but are not limited to: phone calls (landline and mobile), video calls or other video-based communications, screen sharing, VoIP call queuing, comments-based communication in messages, faxes, text messages, other chat and messaging (e.g., chat based communication with attachments that can open to a specific patient context), emails, voicemail, pager, social media, or other forms of communication. When the user is logged into the described system and in the midst of interpretation (e.g., a study from the worklist is currently open for interpretation), the system can selectively control which communications are allowed to interrupt the user and which ones are placed into the communications queue until either the current study interpretation is finished or the user logs off the system entirely. In some instances, the system assigns each communication a priority level. There can be two or more priority levels, such as, for example, high priority communications allowing interruption of the user, medium priority communications that are placed at the top of the queue, and low priority communications that are placed at the back/rear of the queue.

In some cases, the system provides real-time and/or asynchronous context-based communication between users such as radiologists and between radiologists and other stakeholders (e.g., referring physicians). Context-based as used herein refers to the concept of embedding patient or patient-related information within communications. Non-limiting examples of the various components for context-based communications include chat based communication with attachments that can open to a specific patient context, video based communication, screen sharing, comments-based communication in images, VoIP call queuing, or any combination thereof.

Figure 30:
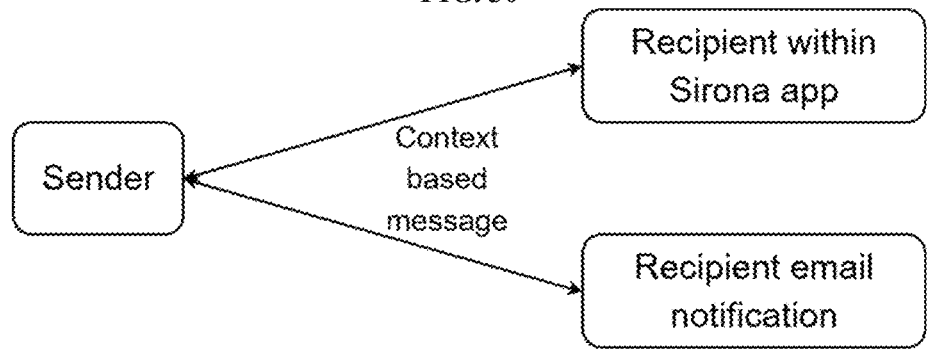
FIG. 30 shows a diagram of the transmission of the message between parties.

Disclosed herein are non-limiting embodiments illustrating how various forms of context-based communications can be implemented. In some embodiments, for chat-based communications, a sender is able to send a message to a recipient who is either using or logged into the same software application (e.g., for AI-assisted image interpretation/analysis) or receives a notification of the message via email. The sender can embed a context based link to a patient study (e.g., having one or more medical images being evaluated) which can be opened in the software application if the user has the right permission. Depending on the user's permission set and the preferences of the sender, they may see a de-identified version of the study. This de-identification can occur dynamically in real-time or be performed ahead of time before the message is sent. FIG. 30 shows a diagram of the transmission of the message between parties.

Figure 31:
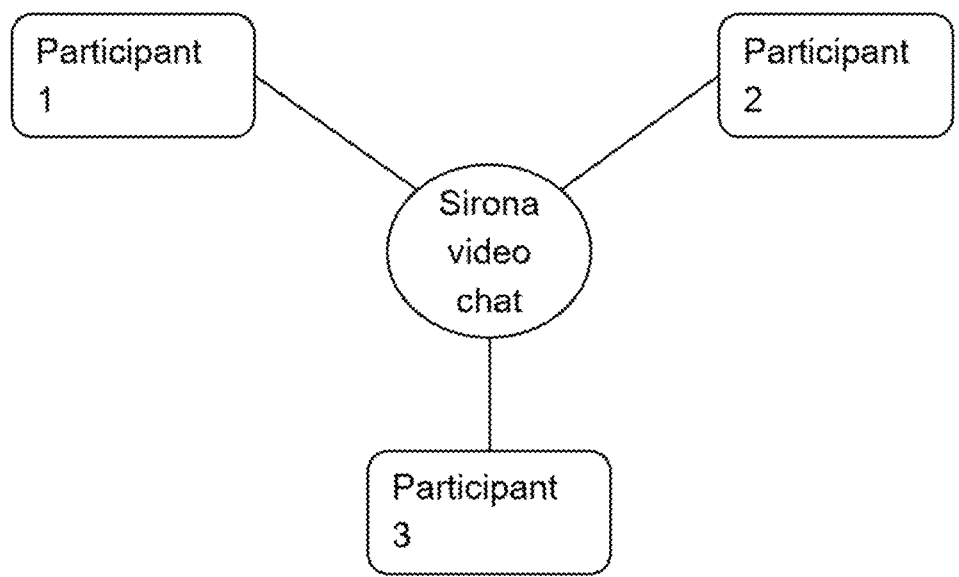
FIG. 31 shows a diagram of video-based communication and screen sharing.

In some embodiments, the user is able to initiate a video chat with other users through the communications hub. This video chat can also include screen sharing where participants can view the screen of another user. FIG. 31 shows a diagram of video-based communication and screen sharing.

In some embodiments, the user is able to utilize comments based collaboration. Users are able to leave comments on images and tag another user to request feedback. The user who is tagged may receive a notification to alert them of a collaboration request. Upon selecting or responding to the notification, they can be taken to the comment in the context of the image and can respond to the comment in a thread (e.g., clicking the notification opens up the image with the relevant portion and the corresponding comment).

Figure 32:
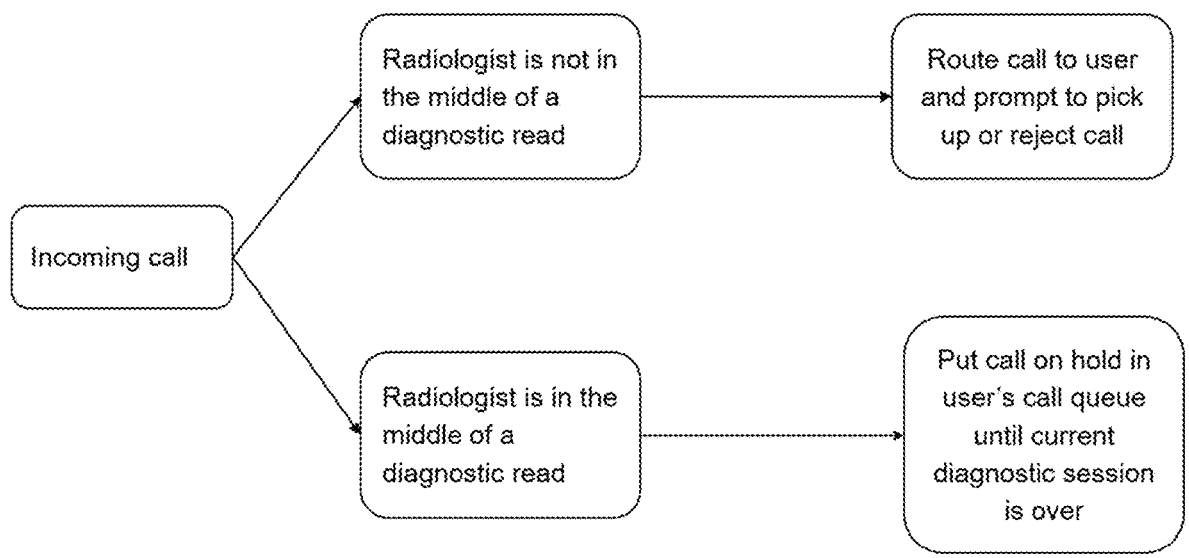
FIG. 32 shows a diagram of VoIP call queuing.

In some embodiments, the user is able to send context-based messages using VoIP call queuing. Each user on the software application or platform can receive a VoIP number which can be routed to receive their phone calls. In some cases, the system intelligently queues phone calls based on where the user is in their workflow. For example, if the user is in the middle of a diagnosis, the system will put the call on hold until the user is done with the current diagnostic session. FIG. 32 shows a diagram of VoIP call queuing.

In some cases, the logic or priority levels of which communications from whom can interrupt are manually determined or customized by the user and/or organization. For instance, phone calls from some specific phone numbers may be whitelisted in while all others queued during interpretation. Optionally, the rules may be set to allow repeated phone calls through after exceeding a set number of repeats. In other communication channels such as text messages or emails, urgent messages may be identified with certain keywords such as "URGENT" or "STAT", while queueing all others. For both audio and text messages, speech to text translation and/or natural language processing may be used in conjunction with machine learning in order to best predict the priority of incoming communications.

Figure 9:
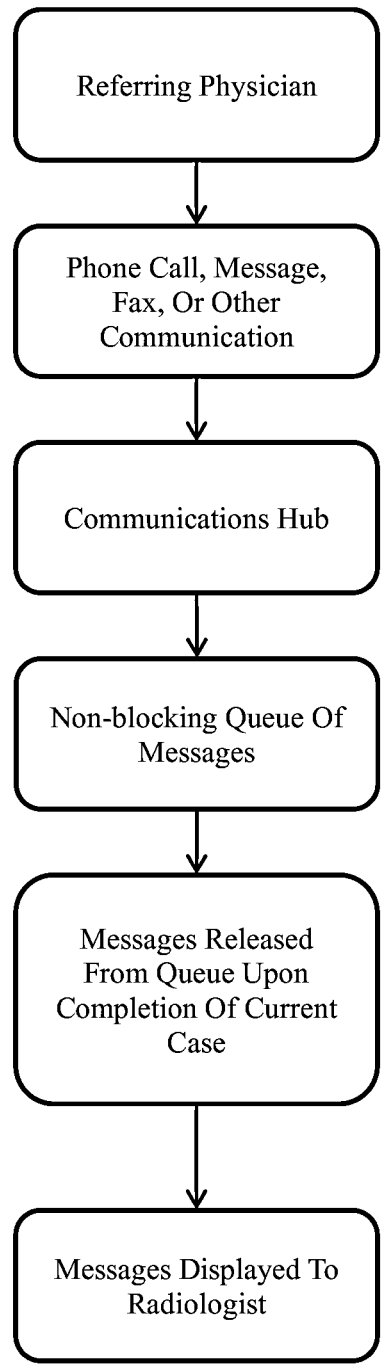
FIG. 9 shows a flow chart illustrating a non-limiting example of a process for managing and/or queueing communications.

In some cases, the logic of which communications are determined through machine learning by either asking the user after each communication whether or not the interruption was acceptable or by observing which communications are responded to during the midst of interpretation. In some cases, after interpretation is finished or the user initiates log off, the queued communications are presented, and the response is facilitated by launching the appropriate application. An example of a flow chart illustrating this process is shown on FIG. 9.

When interpretation is completed and the users is responding to or returning communications, the system is configured to be able to initialize communications such as by starting an email reply, making a voice over IP phone call, or other. Additionally, users may need to share images in real time in order to demonstrate certain clinical findings. A secure, HIPAA-compliant screenshare is made available so that the user can demonstrate to another radiologist or referring physician which portions of the images are most relevant. Alternatively or in combination with sharing the mouse pointer location, eye tracking can be used in order to demonstrate which portion of the image the user is looking at when describing a finding.

Worklist Management

Described herein are systems, software, and methods for facilitating AI-assisted interpretation and reporting of medical images. In some cases, the systems, software, and methods provide a worklist management system that allows radiologists or other users to reserve medical images for analysis. In some cases, a user is able to select a list of cases and/or images having a minimum or maximum number (e.g., at least 1, 2, 3, 4, or 5, or at most 2, 3, 4, 5, 6, 7, 8, 9, 10, 15, or 20) and reserve them, then proceed to review those cases for the next period of time, before selecting another list. This allows users to pick cases they want but discourages cherry-picking of cases by limiting the number of cases that can be reserved and by institutionally defined rules for which subspecialists review which studies. In some cases, the worklist management system is configurable by an administrator and/or radiologist.

Configurable parameters can include the minimum or maximum number of cases that can be reserved, the set time or time period when a user is allowed to reserve case(s), the minimum wait time period before a user can reserve case(s) after an earlier reservation, the type of case(s) or image(s) that a user is allowed to reserve and/or required to reserve (e.g., a user may be required to take a case that is labeled urgent), or other relevant parameters. These processes can be implemented via a system, subsystem, or module, which can be stand-alone or part of a larger platform or system as disclosed herein.

In a medical imaging group practice setting, there are typically multiple patients' imaging studies queued and awaiting interpretation at any given time with multiple physicians available to begin interpretation. In order to prevent two physicians from interpreting the same study, a worklist system can be used to lock a case from review once it is assigned to or reserved by a particular physician. There are several ways for assigning a study to a physician. First, a shared worklist provides all available studies as available for review. Physicians use their own judgement and motives for selecting a study. Alternatively, the assignment of a particular study to a physician may be done by administrative staff or by a computerized workflow engine based upon the criteria provided by practice management. Current workflow engines take into account general information about physicians and their current worklists but do not take into consideration content of study to be assigned other than the imaging modality and body part.

The worklist management system disclosed herein provides an intelligent computerized worklist engine that uses diagnostic AI computer vision in order to optimize the assignment of studies to worklists. Various image analysis systems can be used to infer diagnostic information directly from images. Quantitative image features such as tumor sizing measures can be used for treatment response tracking. CADe and CADx systems can be used to detect and diagnose various types of lesions. As another example, CADt can be used for triaging high urgency cases such as an intracranial hemorrhage (ICH) from head CT in the emergency room that requires immediate attention.

Accordingly, a worklist management system can utilize an AI system to perform computer vision (CV) in order to analyze the content of an imaging study (e.g., one or more images or image series in the study). This information can be used to estimate the difficulty of interpreting a given imaging study, which can be used to influence the likely time and quality for a given physician to interpret the case. The advantage of this approach is that it brings a formal and mathematically optimizable method (from the group practice perspective) for distributing the workload of medical image interpretation in a group practice setting. In comparison, a human administrator requires extra personnel and is based on subjective judgement and bias while letting physicians choose for themselves from a universal worklist is subject to the cherry-picking phenomenon where studies may be individually competed for based on likely ease of interpretation. Conventional worklist engines do not take into consideration any diagnostic information from medical images.

In some embodiments, the worklist management system comprises an intelligent worklist engine that uses a study routing recommendation system or subsystem or module that takes into account information from one or more sources such as, for example, 1) a database of historical and demographic data about physicians, 2) the current state of physicians' worklists, 3) diagnostic information derived from the imaging study itself, or any combination thereof.

Figure 33:
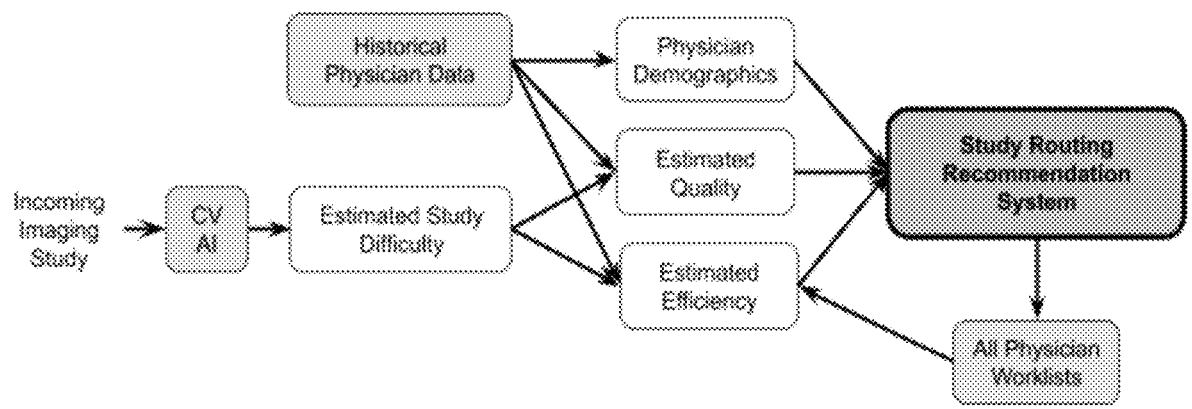
FIG. 33 shows a flow chart illustrating a process for worklist management.

FIG. 33 provides an illustrative diagram of an intelligent worklist engine overview. Incoming study to be assigned to a physician worklist is processed by computer vision/artificial intelligence (CV/AI) system to produce an estimate of study difficulty. Study routing is based on 1) physician demographics (e.g., credentials), 2) estimated study quality derived from both historical physician data and the incoming imaging study, and 3) estimated study efficiency derived from both historical physician data, the incoming imaging study, and the current status of the physician's worklist. In this example, the result of the recommendation is to select a specific physician's worklist for routing the study for interpretation.

Disclosed herein are systems, software, and methods for intelligent worklist management. In some embodiments, the intelligent worklist management system is configured to: receive an unassigned image study; perform computer vision analysis on the image study to generate an estimated difficulty for analysis of the image study; and route or assign the image study to a user selected from a plurality of users based on at least the estimated difficulty and historical user data. In some embodiments, the intelligent worklist management system is configured to: receive an image study; determine an output comprising an estimated difficulty for analysis of the image study; and route or assign the image study to a user selected from a plurality of users based on at least the estimated difficulty and historical user data. In some embodiments, the worklist management system uses a study routing recommendation system or subsystem or module that recommends the user selected from the plurality of users based on physician demographics, estimated quality, estimated efficiency, or any combination thereof. In some embodiments, the estimated quality and estimated efficiency are generated based on the historical user data (e.g., historical physician data) and estimated study difficulty or difficulty for analysis of the image study.

In some embodiments, the worklist management system utilizes an historical physician data source. This intelligent worklist may be a component of a larger web-based system composed of all the tools a user needs to do their job (e.g., intelligent worklist management can be part of an overall system integrating any combination of the systems/subsystems and modules disclosed herein for various functions relating to image review, analysis, report generation, and management). In some embodiments, the Its primary functionalities include image viewing, report generation and worklist management. As users view images, generate reports and go through various patient cases their interaction with the system can be stored in a database. For example, whenever a physician selects and interprets a patient study from the worklist, usage and interaction data may be tracked and stored in a database. Furthermore, peer review data can also be performed and stored within the web-based system, allowing for estimates of the diagnostic quality of individual physicians as judged by their peers on a statically sampled basis.

In some embodiments, physician demographic data includes but is not limited to items such as subspecialty training and qualifications, state licensure and credentials, years of practice, work schedule, or any combination thereof. Estimated quality and estimated efficiency can be determined using at least physician-specific information and/or study-specific information. Physician quality metrics are derived primarily from the aforementioned peer review process. This peer review process may be performed either external to the medical practice or internally, requiring other physicians to review (or "overread") selected prior interpretations and identify discrepancies including their severity and clinical significance. Another source of peer review data is from the aforementioned AI-assisted quality metrics described within this patent. Physician efficiency metrics can include but are not limited to study turnaround time (TAT) and interpretation time, with adjustments for interruptions (see aforementioned communications hub in this patent), for diagnostic difficulty (both from report content analysis as well as by computer vision as described in this patent), and for time spent on setup tasks where a setup task is any task the user performs outside of looking at image pixels and creating reports such as selecting a layout for image viewing and dragging and dropping the appropriate series into the layout.

Physician Worklists. In some embodiments, in order to provide load balancing across physician worklists, the worklist management system takes into consideration one or more load balancing factors. For example, the system may incorporate information regarding the distribution of studies across all physician worklists at the time of study assignment. One or more rules can be used to incorporate the one or more load balancing factors into the worklist management process. For example, physicians with shorter current worklists are more likely to be assigned an image study all other things being equal. In some embodiments, physicians work schedules are taken into consideration so that worklist completion coincides with the end of their scheduled workday. The ability to manually request lesser or greater work can also be taken into consideration.

AI Estimated Study Difficulty. In some embodiments, the worklist management system estimates the difficulty in interpreting and reporting the results. Certain embodiments employ AI-assisted detection of findings to assess the diagnostic content of the imaging study with the number of imaging findings weighted by their uncertainty, for example, |1-probability of finding|. Certain embodiments also include increased weighting for rare, low-prevalence findings and/or for low image quality.

In some embodiments, physician quality metrics and AI estimated study difficulty are combined in order to produce an estimate of diagnostic quality anticipated for a given study. Two or more of physician efficiency metrics, AI estimated study difficulty, and the current state of physician worklists can be combined in order to produce an estimate of interpretation efficiency for a given study. These mathematical combinations may be produced by, but are not limited to, linear combinations, non-linear combinations such as power-law or exponentiated combinations, or machine learning functions that may be trained to learn the combination of these inputs that most accurately predicts actual quality and efficiency for a given set of imaging studies.

In some embodiments, in order to make study assignments to physician worklists, physician demographics, estimated quality, and estimated efficiency are combined using criteria and heuristics as defined by the medical practice in order to balance between overall efficiency (TAT for the practice) and overall quality (aggregate peer review metrics for the practice) while meeting individual physician preferences and medico-legal duties. In certain embodiments, the mathematical function that is maximized to produce the study assignments to physician worklists is an artificial neural network. In some embodiments, the artificial neural network is trained using reinforcement learning where the recommendation system is the agent with assignments as actions, trying to maximize rewards of combined efficiency and quality. Over long enough periods of time, the reinforcement learning algorithm for recommendations is able to continually improve combined efficiency and quality by adjusting worklist recommendation policy.

AI-Enabled Quality Metrics

Described herein are systems, software, and methods for facilitating AI-assisted interpretation and reporting of medical images. In some cases, the systems, software, and methods utilize natural language processing (NLP) and/or computer vision to enable better over-reads of imaging studies for quality assessment. NLP can be applied to comparative studies in order to auto-generate the necessary over-read statistics as required by the government. In some cases, studies that have been interpreted by one group of users such as a senior radiologist are fed into the workflow of another user group (e.g., junior radiologists), and NLP and machine learning are used to perform automatic over-reading and measurement of clinical quality. In some cases, computer vision and NLP are used to perform one or more of the following: (1) compute report text quality metrics, (2) enable automated comparison of over-read studies, and (3) enable a fully automated over-read for quality assurance. These processes can be implemented via a system, subsystem, or module, which can be stand-alone or part of a larger platform or system as disclosed herein.

In diagnostic radiology, peer review is the process of assessing accuracy of a radiology report by another user. Currently, this involves the subjective opinion of either the second user or a different third party. The reviewer may use a standardized rating scale. For example, a three-point scale may distinguish between (1) concurrence, (2) discrepancy where the finding would not necessarily be expected to be noted, and (3) discrepancy where the finding should be made all the time. Discrepancies can be noted as being clinically significant or not. Note that this is distinct from double reads, second reads, or over-reads where two users read a study independently, and distinct from joint reporting where two users reach a consensus opinion. This peer review can be used for quality assurance or quality improvement purposes. Flowcharts illustrating the clinical workflow for producing a radiology report and the workflow for peer review are shown in FIG. 10.

As an example, the American College of Radiology (ACR) offers the annual fee-based RADPEER system. In this web-based program, a study and report are submitted without the original radiologist name and the results are presented back to the radiology practice chairman. In the US, the Medicare Improvements for Patients & Providers Act of 2008 (MIPPA) created criteria for accreditation with CMS that include peer review, such as with RADPEER. Costs of RADPEER are approximately $80-160 per physician per year.

According to the Donabedian framework, quality measures or metrics can be categorized as structural, process, or outcome measures. Structural measures are typically relating to safety and technical equipment measures. Process measures are commonly used due to their ease of measure and include things like report completion times, patient waiting times, etc. Outcome measures which are the most desirable are also the hardest to measure. Currently, peer-review is used as a proxy for true diagnostic accuracy and implemented in systems such as RADPEER.

Figure 11:
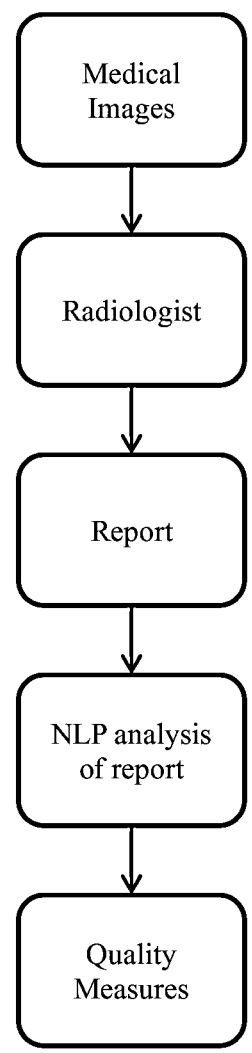
FIG. 11 shows a flow chart illustrating a non-limiting example of AI-assisted or automated analysis of the language of the radiology report to produce quality or performance metrics.
Figure 12:
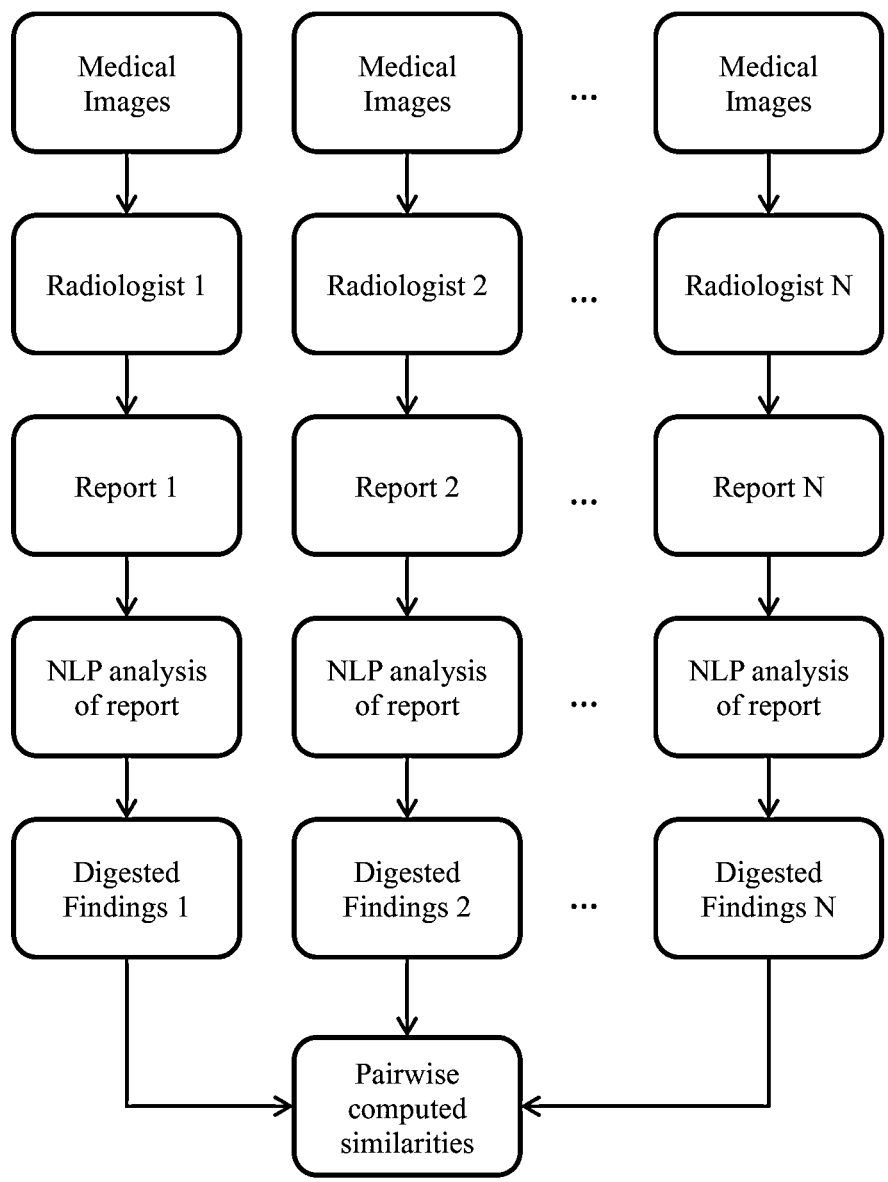
FIG. 12 shows a flow chart illustrating a non-limiting example of an over-read comparison process in which natural language processing is used to create digested findings for each report which can then be compared in a pairwise manner.

Accordingly, in some aspects, the systems, software, and methods disclosed herein perform AI-assisted or automated analysis of the language of the radiology report to produce quality metrics. For instance, reports that use phrases to indicate uncertainty, often referred to as "hedging" are discouraged by referring physicians. Therefore, the NLP system disclosed herein can be configured to detect phrases indicating hedging and first produce warnings and/or suggestions to the user as they dictate the report. Additionally, the system can quantify and track tendencies to hedge over time so as to identify negative trends and patterns that can be improved upon. These trends and/or patterns can also be scored or assessed with a quality control metric in order to provide feedback or guidance to the radiologist or user. For example, a performance report may be provided that includes a quality control assessment, such as, for example, one or more of the following: a comparison of the user's usage of hedging language relative to the average for the practice group, a breakdown of the types of images/analyses and their corresponding use of hedging language to help identify strengths/weaknesses, and an accompanying suggestion or guidelines to decrease use of hedging language. An overview of this improved quality review workflow is shown in FIG. 11. The current system of peer review (see FIG. 10) has the peer reviewer reading the case with the user's report available to them which has the potential to lead to bias. One of the features of the NLP system disclosed herein is the ability to digest radiology report free text into a structured format of individual findings that follow a specific information model (anatomic location, observation, severity). Once in this structured format, the findings can be statistically compared. This enables a new paradigm for over-reads where more than one user reads a study without even having knowledge of participating in a peer-review process and then the reports are compared later. This enables for a completely blinded review process. FIG. 12 shows a flowchart illustrating this over-read comparison process in which natural language processing is used to create a systematic list of digested findings for each report which can then be compared in a pairwise manner.

Figure 13:
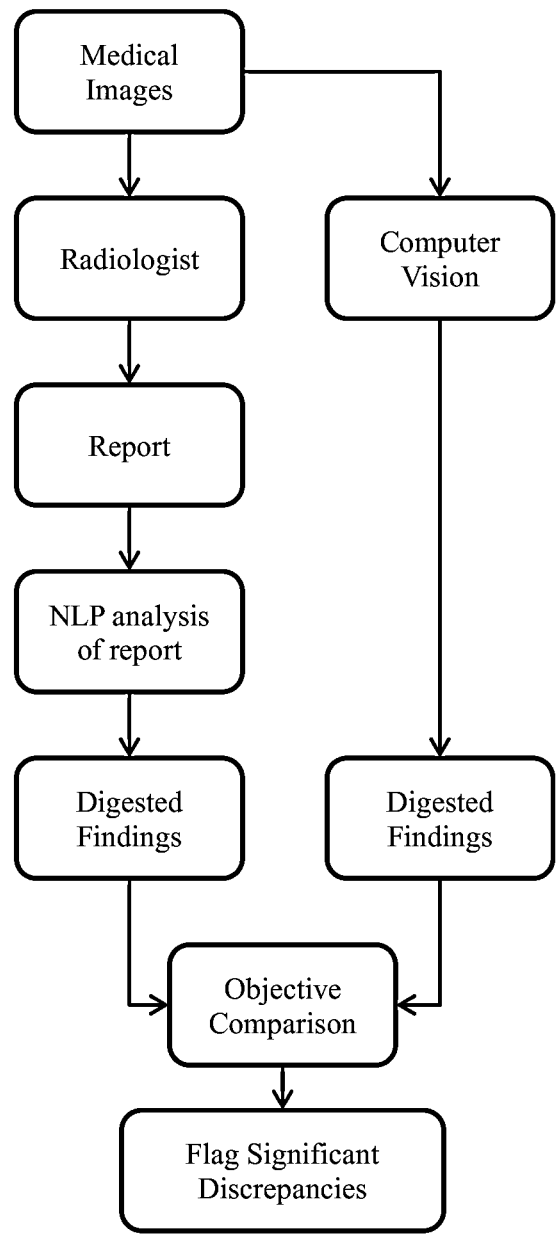
FIG. 13 shows a flow chart illustrating a non-limiting example of a process of automated review using AI computer vision to create a systematic list of digested findings that can then be compared to the NLP digested radiologist report for an objective comparison.

In some aspects, the systems, software, and methods disclosed herein enable detection of findings in a manner analogous to what the user records in the "FINDINGS" section of their report. This can be produced in same format as the NLP-interpreted digested findings discussed throughout the present disclosure. Within this design, the AI computer vision and the NLP systems act as a separate over-read without requiring any extra user effort, thus enabling a fully automated quality assurance system. In some cases, the system automatically flags reports that contain significant discrepancy between user and the AI computer vision system for further inspection and review. FIG. 13 shows a flowchart illustrating this process of automated review using AI computer vision to create a systematic list of digested findings that can then be compared to the NLP digested radiologist report for an objective comparison.

AI-Assisted Self-Improvement

Described herein are systems, software, and methods for facilitating AI-assisted interpretation and reporting of medical images. In some cases, the systems, software, and methods utilize machine learning to analyze data on how users engage with the computer vision and/or NLP systems to predict the quality of the users' process (e.g., analytics), and optionally offer tips for improving the quality and efficiency of their process. This information can also be used to determine the key images in a case using machine learning. A byproduct of users using the systems disclosed herein is that data can be gathered and analyzed for how the most productive and experienced radiologists engage with the system/software, especially when compared to the less productive and less experienced radiologists. Using this data, machine learning methods can be employed to inform and train radiologists to use and engage with the system/software in the same way the most productive, experienced radiologists do. These processes can be implemented via a system, subsystem, or module, which can be stand-alone or part of a larger platform or system as disclosed herein.

The systems, software, and methods disclosed herein can be configured to determine or estimate quality. As described throughout the present disclosure, interpretive quality may be determined by various metrics, including methods such as peer-review and AI-assisted or automated quality measures. These metrics can be stored and tracked over time, enabling identification of trends or progression of individual radiologists. Over time, these peer-review measures allow identification of usage patterns of radiologists associated with the highest quality.

The systems, software, and methods disclosed herein can be configured to capture image navigation information. During free search when the user is not being prompted by AI as to where to concentrate, the system can capture information about which images are being examined and in what pattern. For instance, some users might choose not to examine some series (e.g., scout images) due their sub-diagnostic quality. However, other users may choose to examine those series due to medico-legal reasons. The system can record and analyze these differences amongst users. In some cases, the system records which images in a stack of images are viewed and for how long. Additional information that can be recorded and analyzed include eye gaze or gaze fixation information using eye-tracking hardware. The system can analyze this information to find differences in patterns between users with different quality assessments. In some cases, when a user is scrolling through images too fast or not spending enough time looking at peripheral areas of anatomy compared to higher performing radiologists, these differences may be noted and reported to the user for self-improvement. UI related measures such as mouse odometer measurements may be made in order to determine ergonomic impediments to accurate and efficient interpretation. Information regarding interruptions to the interpretation process may also be inferred and tracked.

Figure 14:
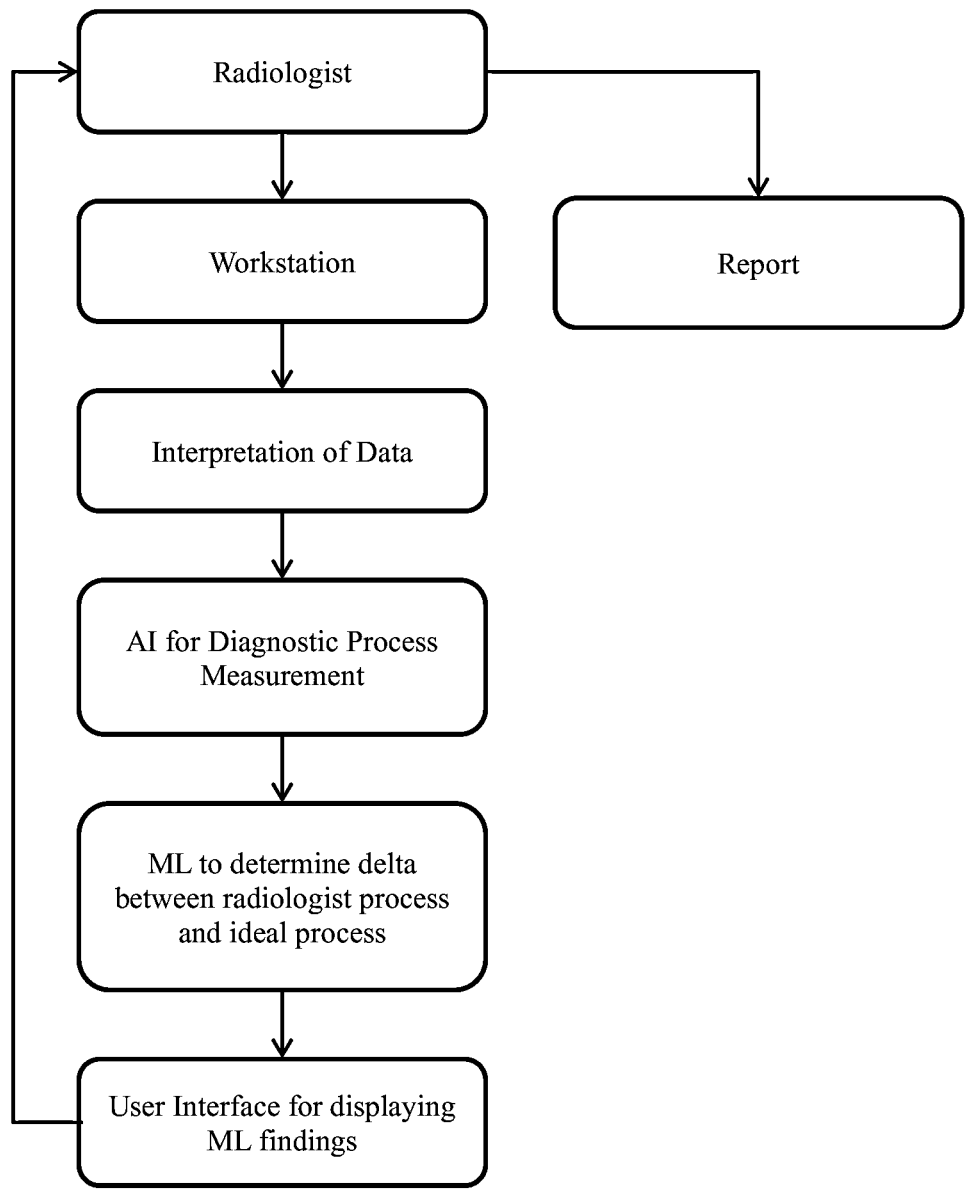
FIG. 14 shows a flow chart illustrating a non-limiting example of a process for assessing and comparing the radiologist's findings to the "ideal" finding/process (e.g., from a more experienced/skilled radiologist) according to one or more performance or quality metrics.

The systems, software, and methods disclosed herein can be configured to capture AI interaction information. The AI systems disclosed herein can present potential findings to the user in as least constraining a way as possible. For instance, the findings might be presented and/or navigated in order of decreasing confidence or probability. Alternatively or in combination, the findings may be navigated in spatial order (e.g., from inferior to superior) or by organ system. Differences in patterns between users can be algorithmically analyzed to determine which patterns lead to the highest quality interpretations. Users with lower ranking or anomalous patterns may be notified to provide the opportunity for self-improvement. FIG. 14 shows a flowchart illustrating this process. As shown, the user uses the workstation to access and interpret the medical data to generate findings for insertion into the report. The report is generated, but in addition, a process for assessing and comparing the user's findings to the "ideal" finding/process from a more experienced/skilled radiologist is carried out. Specifically, the AI algorithm analyzes the findings to generate one or more performance or quality measures/metrics. The findings are then compared to determine the delta or difference in performance. Finally, the results of this comparative analysis can be provided to the user.

Artificial Intelligence for Hanging Protocols

Described herein are systems, software, and methods for facilitating AI-assisted interpretation and reporting of medical images. In some cases, the systems, software, and methods provide automated generation of hanging protocols. When a user opens a case, a "hanging protocol" is used to display the images in the configuration the user likes to view them in. Currently, the user must create these "hanging protocols" manually, which is an inefficient process. Accordingly, in some cases, machine learning is applied to user engagement data and the medical image header data to automate the process of determining the way the images should be aligned on the screen. This allows for each case to be displayed according to the user's preference. Such customization and automation provide for a more streamlined and efficient process for image interpretation and report generation. These processes can be implemented via a system, subsystem, or module, which can be stand-alone or part of a larger platform or system as disclosed herein.

The system for generating or provisioning hanging protocols can be referred to as a hanging protocols system or subsystem or module. The hanging protocols system or subsystem or module can be implemented to provide hanging protocols functionality alongside one or more of the other systems, subsystems, or modules disclosed herein. As an illustrative example, a system for AI-assisted interpretation and reporting of medical images can comprise a hanging protocols system/subsystem/module that identifies or applies the appropriate hanging protocol alongside other systems/subsystems/modules such as those involved in AI-assisted image segmentation, feature identification or image labeling, intelligent worklist management, etc.

Due to differences in imaging hardware, differences in study protocols, and changes over time, the set of imaging series acquired in a study and their textual descriptions may vary significantly making it difficult to match series between current and prior study. An analysis of the technical imaging parameters (e.g., TE and TR in MRI) allows for a detailed comparison between series. In some cases, machine learning methods are used to determine series similarity by analyzing a vector of standardized technical acquisition parameters from the DICOM images.

In healthcare environments where patient medical images are interpreted and reports are generated, various methods are used for displaying multiple images simultaneously. Historically, when analog light boxes were used to view films, the term "hanging protocol" referred to the physician's preferred layout of the multiple films in a given patient imaging study. With digital imaging as the current dominant paradigm, hanging protocols now refers to the mapping of specific image series (or specific images) to a multitude of viewports spanning a rectangular grid, often across multiple computer displays. As exemplified by the DICOM standard, the process flow for hanging protocols consists of two stages: (1) hanging protocol definition, which includes selection, and (2) hanging protocol display, which includes processing and layout.

During the hanging protocol definition stage, when given an imaging study in selection, the goal is to match against an archive of potentially applicable hanging protocols that will define the display and layout of the images or image series on the computer display(s). Matching criteria can include modality, anatomy, laterality, procedure, reason for procedure, the number of priors, or any combination thereof. Also included in the matching process can be display environment including number of displays, resolution of displays, and/or bit depth of the displays. Finally, an image set can be defined by matching specific image or image series attribute values against the set defined in the hanging protocol. However, this often fails due to the dependence on a free text series description tag that varies from site to site and operator to operator.

During the hanging protocol display stage, in processing, image sets are mapped to display sets as specified by the hanging protocol by reformatting (e.g., MPR, 3D rendering), filtering (e.g., "axial"), sorting (along axis or by acquisition time), or other criteria. This stage can also define the ordered image box set. In layout, the mapping of image boxes to display locations can be performed according to the ordering defined in the processing step.

Conventional approaches to hanging protocols generally use simple attribute value matching criteria for both definition as well as display, which tend to be brittle and unable to handle variability from expected attribute values. However, in real-world practice, there is significant variability in attribute values, which causes a high rate of failure of existing hanging protocols. Even when machine learning approaches are used for definition and/or display, the task is framed as a search process with either one correct match of image series to viewport or no match at all. In selection, the image study metadata attribute values are examined in order to find the single matching protocol, either by simple attribute values matching rules or by machine learning applied to attribute values or other high level information regarding the study. In display, the process of matching images or image series against an expected list follows the same search process matching paradigm. In both cases, brittleness against modest deviation from expectations regarding the metadata ensues. For example, a slight difference in the study description string (e.g., using "LT KNEE" rather than "LEFT KNEE") in a new study may result in no match to any known hanging protocol. As another example at the series level, a minor variation in metadata (e.g., "T1w AX" rather than "T1 AXIAL") may result in a failure to match an in the image set and thus, a viewport goes empty.

Disclosed herein are systems, software, and methods for improved provisioning of hanging protocols. An advantage of the present disclosure is a reframing of the problem from one of search/matching discrete entities (e.g., imaging study to hanging protocol; display sets to image boxes) to a numerical optimization problem. In some embodiments, the hanging protocol system described herein optimizes a set of criteria that define a desirable selection and layout of image series. As an illustrative example, rather than defining the hanging protocol by saying "put this exact type of image in this exact location," the systems, software, and methods disclosed herein allow the user to define the criteria, either explicitly or by providing example(s), that will be optimized. There is no hard coding of what information must or must not be present. Instead, the system is far less brittle because the numerical optimization only operates on the information at hand, whether or not it fits into an inflexible, preconceived schema.

In some embodiments, disclosed herein is a method for providing a hanging protocol, comprising: receiving user input defining one or more criteria for optimization; and providing a hanging protocol based on said one or more criteria. In some embodiments, disclosed herein is a method for providing a hanging protocol, comprising: obtaining an image study or image series comprising one or more images; receiving user input defining one or more criteria for optimization; and providing a hanging protocol optimized for said image study based on said one or more criteria. In some embodiments, the hanging protocol is not optimized based on hard coding (e.g., preset rules establishing requisite criteria) of criteria that is allowed or not allowed. In some embodiments, the hanging protocol is optimized based on numerical optimization. The hanging protocol systems, software, and methods can be used in combination with any of the other systems, software, and methods disclosed herein to the extent they relate to viewing, reviewing, analyzing, or otherwise interacting with images (e.g., AI-assisted findings, automated report generation, etc.). As an illustrative example, a user may use a system that performs AI-assisted image segmentation and generation of findings for automated/semi-automated report generation, which utilizes a hanging protocol system/subsystem for provisioning the display and layout of images as part of the review of the medical image. In some embodiments, the criteria correspond to one or more study attributes. In some embodiments, the criteria comprise one or more prior image studies. In some embodiments, the criteria comprise one or more prior image studies comprising one or more images or image series. In some embodiments, one or more prior image studies are selected by a user to establish criteria. As an illustrative example, a user selects several exemplar image studies or image series relating to chest X-rays to set criteria for future chest X-ray image studies or image series. The relevant features from these prior image studies or image series are extracted and used to determine the one or more attributes used to optimize the hanging protocol that is ultimately used for the current image study or image series. In some embodiments, the hanging protocol is optimized based on one or more attributes extracted from the one or more prior image studies. In some embodiments, optimization of the hanging protocol comprises selection of an optimal hanging protocol from a plurality of hanging protocols based on one or more attributes extracted from one or more prior image studies. In some embodiments, optimization of the hanging protocol comprises obtaining information from at least one of imaging order, clinical text, metadata (e.g., DICOM metadata), or image data (e.g., DICOM pixel data) for the image study. In some embodiments, optimization of the hanging protocol comprises using a natural language processing algorithm to extract one or more relevant features from the imaging order, clinical text, or both. In some embodiments, optimization of the hanging protocol comprises extracting relevant features from the image data using a computer vision algorithm. For example, the computer vision algorithm can be configured to identify or extract visual features that provide information about study attributes. In some embodiments, optimization of the hanging protocol extracting features from the metadata (e.g., DICOM metadata). In some embodiments, optimization of the hanging protocol comprises providing extracted features as input to a machine learning classifier to generate as output one or more attributes. In some embodiments, the hanging protocol is optimized according to the one or more attributes generated by the machine learning classifier.

Study-level Classification. In some embodiments, study-level classification is performed. Study attributes can be defined, for example, by the RadLex Playbook, and include one or more attributes such as modality (e.g., MR), modality modifier (e.g., angiography), procedure modifier (e.g., transjugular), population (e.g., pediatric), body region (e.g., neck), anatomic focus (e.g., spine), laterality (e.g., left), reason for exam (e.g., screening), technique (e.g., dual energy CT), pharmaceutical (e.g., with IV contrast), view (e.g., lateral), or any combination thereof.

In some embodiments, these attributes are inferred by a machine learning classifier that takes into consideration one or more sources of information, for example, the imaging order, clinical text, DICOM metadata, and/or DICOM pixel data. In some embodiments, natural language processing (NLP) is used to determine the text-based features that are in part relevant for determining the study attributes. In some embodiments, supervised document classification is used to predict the study attribute values for one or more of the aforementioned study attributes. DICOM metadata values can be divided into unstructured strings (e.g., study description) and categorical or continuous values (e.g., echo time or repetition time). In some embodiments, from a training dataset, unstructured strings are tokenized and then vectorized. In some embodiments, categorical data are one-hot encoded while continuous values are used directly to create a metadata vector that is passed into the classifier. In some embodiments, pixel data are fed through a computer vision model to predict study attributes. In some embodiments, convolutional neural networks such as ResNet-50 are used to predict study attribute values where the model is trained either image by image or series by series and the results are aggregated to create a study-level estimate of each study attribute.

Figure 34:
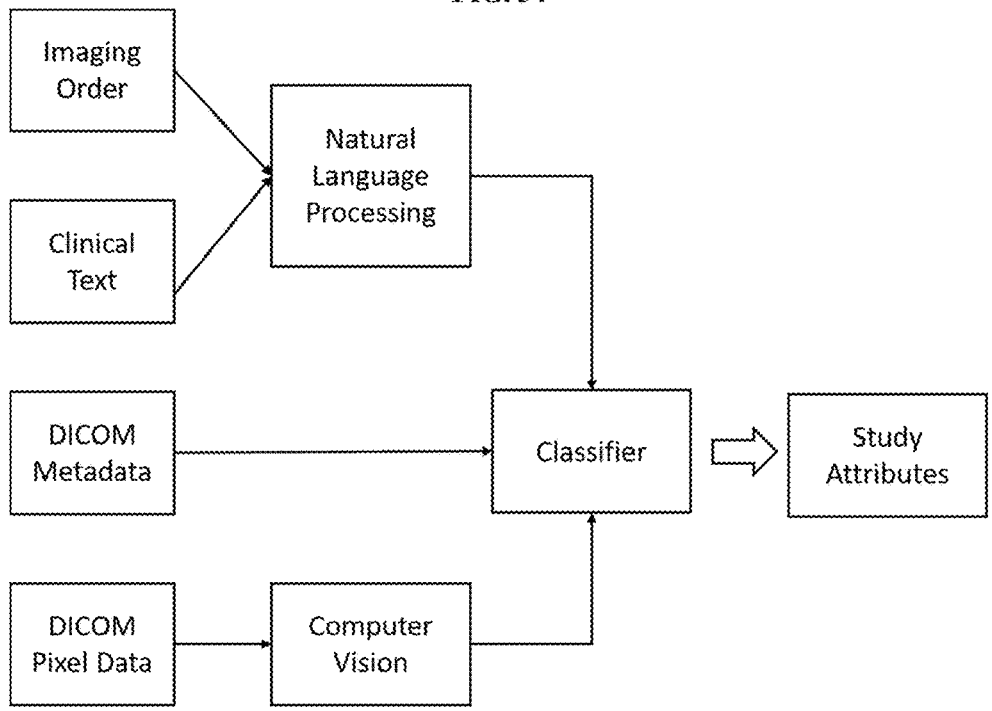
FIG. 34 shows an illustrative diagram illustrating a process for study-level classification using imaging orders.

An illustrative diagram of a process for determining study attributes is shown in FIG. 34 FIG. 34 shows a diagram illustrating a process for study-level classification using imaging orders, clinical text, DICOM metadata, and DICOM pixel data as input. Natural language processing is used to extract relevant features from imaging orders and clinical text that provide some information about study attributes. Computer vision is used to extract visual features that provide information about study attributes. A machine learning classifier is then used to combine these along with DICOM metadata in order to produce a list of study attributes.

In some embodiments, the systems, software, and methods disclosed herein optimizes the display of images to include one or more prior studies relevant to a current image study or image series. The process of identifying relevant prior studies or images can be referred to as "relevant prior determination". Optimizing the display of images via an optimal hanging protocol can include display of one or more prior studies that are relevant to the current study under review. Patients may have prior imaging studies that are not relevant, for instance if the current study is a head CT but there is a prior study that is an X-ray of the ankle. In some embodiments, the extracted study attributes are used to determine relevant priors (e.g., image studies, image series/images) from a list of all patient prior imaging studies by allowing the user to select the criteria for relevance, which optionally includes matching or partially matching body region, anatomic focus, laterality, or any combination thereof. In some embodiments, computer vision is used to determine which body parts are imaged, which enables a level of performance of relevant prior determination that has not been achieved before. Conventional methods that use only metadata such as a series description may be able to determine that an MRI is of a lower extremity but unable to distinguish between knee, leg, ankle, or foot, whereas the natural language processing and computer vision-based methods described herein are able to solve this commonly encountered problem.

In some embodiments, the systems, software, and methods for optimizing hanging protocols disclosed herein are directed to image study level classification or image series level classification. There is no current solution for characterizing different image series. Accordingly, in some embodiments, the systems, software, and methods disclosed herein provide a classification schema for image series as well as a mechanism for determining the values of each series attribute.

The image series schema attributes can include type (e.g., source image, scout/localizer, secondary capture, document), orientation/view (e.g., axial, coronal, etc.), weighting/tissue selection (e.g., T1w, STIR), contrast (e.g., intravenous), phase/timepoint (e.g., peak arterial phase), acquisition (e.g., thin slice), reconstruction (e.g., bone kernel), or any combination thereof. Similar to the study-level classification process, metadata (e.g., DICOM metadata) and/or image data (e.g., DICOM pixel data) can be fed into a machine learning classifier to produce a list of series attributes such as those listed above. One advantage of using this image series attribute schema is that effectively identical series are easily identifiable as having the same series attributes values. This may occur when a series is re-acquired due to some problem with the first acquisition such as excessive patient motion. Typically, the interpreting physician does not want to display the first acquisition in the hanging protocol. This method for classifying multiple series attributes is in contrast to the commonly described method that enumerates all possible series as a flat list.

Figure 35:
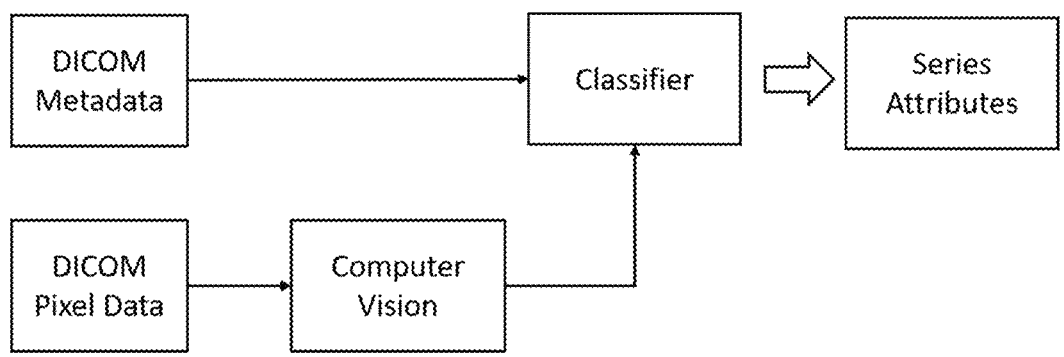
FIG. 35 shows an illustrative diagram of a process for series-level classification.

FIG. 35 shows an illustrative diagram of a process for series-level classification. As shown in FIG. 35, series-level classification is performed using DICOM metadata and DICOM pixel data as input. Computer vision is used to extract visual features that provide information about series attributes. A machine learning classifier is used to combine these along with DICOM metadata in order to produce a list of study attributes.

The systems, software, and methods disclosed herein can carry out relevant series determination and display preference. In defining the hanging protocol, users may indicate the series attributes values for the series they expect to find and then define the rules for display and layout, either explicitly or by example. Accordingly, the display can be defined as displaying a 2D image stack, a multiplanar reformat (e.g., sagittal from axial acquisition), curved planar reformat, volumetric rendering, or some other suitable format. Users may indicate specific series they do not wish to include, such as secondary captures or documents. In some embodiments, if a user has neither defined how they want to display a type of series nor excluded it, then it is indeterminate. Conventional hanging protocol systems often fail to match exact metadata values (e.g., series description) and will thus fail to include that series for display, even though the user may wish to have it displayed. By contrast, the present systems, software, and methods are configured such that the indeterminate series, neither explicitly included nor excluded, are displayed by default using a basic 2D image stack display. An advantage of the series attribute scheme described herein is that it allows for a generalized classification of all image series that allows for flexibility not achieved by conventional systems.

The systems, software, and methods disclosed herein can configure a layout for the display. Conventional hanging protocol layout definition requires pre-defining the size of the viewport grid on each display (e.g., 3×4) and defining the exact series to be displayed in each viewport. By contrast, disclosed herein are systems, software, and methods that that do not require a pre-defined viewport grid and does not require explicit definition of the series to be displayed in each viewport. This is advantageous because if a user interprets images in different settings with different display hardware (e.g., home vs. office), the dynamic layout engine described herein is able to adaptively adjust to each situation while respecting the general user preferences for display. Additionally, because of the heterogeneity of how many relevant series exist and how many relevant prior studies exist, the number of needed viewports may vary on a patient-by-patient basis. Yet another advantage of the dynamic layout engine is that the user may wish to toggle on/off certain series such as a third or fourth prior study, and the dynamic layout will adjust in real time with an optimized overall layout.

Figure 36:
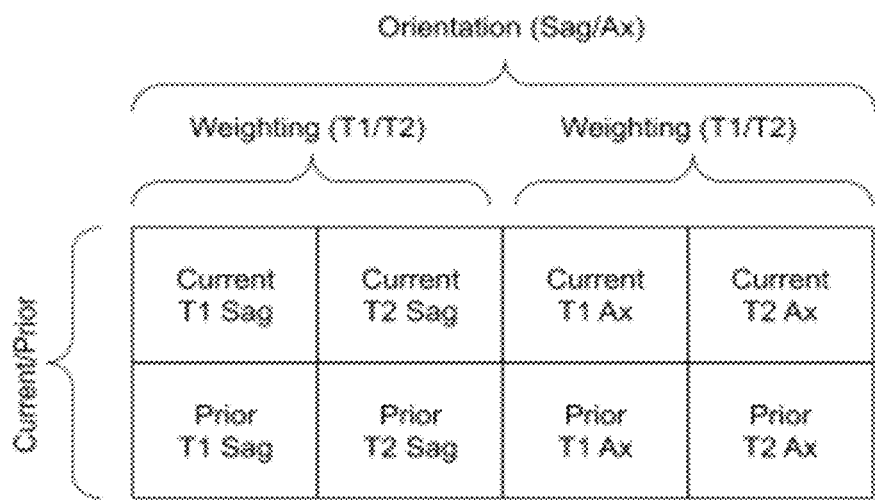
FIG. 36 provides an illustrative example of a desired layout of a current and prior MRI study into a 2×8 viewport layout.

FIG. 36 provides an illustrative example of a desired layout of a current and prior MRI study into a 2×8 viewport layout. The current/prior attribute is on rows while the coarsest column attribute is orientation (sag/ax) and the most granular column attribute is weighting (T1/T2). The ordering of values within each attribute is also defined (Sag<Ax, T1<T2).

In the specific example of a method for specifying layout illustrated via FIG. 36, each series attribute is associated with either rows or with columns. For rows and for columns, the ordering of the associated series attributes is done from coarse to granular. Finally, for each series attribute, the individual values are ordered according to user preference. In the illustrative example of a method for specifying layout, the user manually drags and drops image series into viewports until they are satisfied. The row vs. column assignment, the coarse to granular ordering, and the attribute value ordering are inferred from the provided example. It is possible that the user provides an inconsistent ordering in which case the more predominant case can be used to define the layout rule, with ties being broken by system default choices. Additionally, the user's actions in rearranging hanging of image studies may be tracked over time with a weighted running average of the learned rules used to improve performance.

In some cases, an issue that can arise is how to arrange the layout if certain viewports are unfilled. For example, if a hanging protocol expects a current T2 axial series that does not exist. This problem can occur often across current and prior studies where the image acquisition protocol, or even the imaging modality, may vary. Rather than leaving numerous blank viewports, the system described herein allows for defining an optimization scheme that can place higher value on filling as many viewports as possible over following the exact row/column ordering rules. For example, each rule is given a weight such that when satisfied, the objective function for that layout increases by that weight. A different weight may be given for each filled viewport. Additionally, other considerations for layout optimality may be considered with different weight such as the aspect ratio and size of each viewport. Accordingly, in some embodiments, layout is optimized based on a plurality of weighted rules.

Medical Image Data

In some cases, the systems, software, and methods disclosed herein comprise one or more models or algorithms for analyzing or interpreting a medical image or medical imaging data. A medical image can be collected from a subject using various medical imaging techniques and can be selected from one or more of the following non-limiting examples: a radiographic image such as an X-ray image, a magnetic resonance imaging (MRI) image, an ultrasound image, an endoscopy image, an elastography image, a thermogram image, an echocardiography image, a magnetic particle image, a photoacoustic image, an electrical impedance tomography image, a corneal topography image, a positron emission tomography (PET) image, a single photon emission computed tomography (SPECT) image, an optical coherence tomography (OCT) image, an X-ray computed tomography (CT) image or computed axial tomography (CAT) image, a microscopy image, and a medical photography image.

The medical image can be directed to specific portions of the anatomy or tissues. In some cases, a set of medical images are taken of the same anatomical feature or tissue. The medical image can be 2-dimensional, 3-dimensional, or in some cases, higher dimensional such as, for example, a time-series of 3D images showing progression of a tumor. A 4-dimensional image may include x/y/z 3-D coordinates and also the time (t) dimension. Additional dimensions are also possible, for example, 5-dimensional images that include x/y/z coordinates and 2 additional dimensions such as time (t) and color-coding to indicate spectral or wavelength dimension of the imaging technique.

The medical image or medical imaging data can be stored within a database. The database can be a local database such as on a local server or a remote network or cloud database. In some instances, the database includes metadata and/or data non-image related medical information of a specific subject, such as medical history, known allergies, vaccinations, illnesses, and other potentially relevant information. In some cases, the database includes the subject's treatment plan or procedure information. A computer processor as disclosed herein can access the data contained within the database and provide the user access to this data.

Algorithms and Machine Learning Methods

Various algorithms can be used to carry out the processes disclosed herein such as natural language processing, speech to text translation, gaze fixation point detection, quality metric generation and/or comparison, image and/or communications queueing, computer vision including image segmentation, clinical finding generation, or any combination thereof. In some instances, machine learning methods are applied to the generation of models for evaluating information in carrying out these processes. Such models can be generated by providing a machine learning algorithm with training data in which the expected output is known in advance, e.g., the correct segmentation and labeling are known for the image.

The model, classifier, or trained algorithm of the present disclosure can comprise one feature space. In some cases, the classifier comprises two or more feature spaces. The two or more feature spaces may be distinct from one another. Each feature space can comprise types of information about a case, such as biomarker expression or genetic mutations. The training data is fed into the machine learning algorithm, which processes the input features and associated outcomes to generate a model or trained algorithm. In some cases, the machine learning algorithm is provided with training data that includes the classification, thus enabling the algorithm to "learn" by comparing its output with the actual output to modify and improve the model. This is often referred to as supervised learning. Alternatively, in some instances, the machine learning algorithm is provided with unlabeled or unclassified data, which leaves the algorithm to identify hidden structure amongst the cases (e.g., clustering). This is referred to as unsupervised learning. Sometimes, unsupervised learning is useful for identifying the representations that are most useful for classifying raw data (e.g., identifying distinct segments within an image such as vertebrae in an X-ray of the spine).

An algorithm may utilize a predictive model such as a neural network, a decision tree, a support vector machine, or other applicable model. Using the training data, an algorithm can form a classifier for classifying the case according to relevant features. The features selected for classification can be classified using a variety of viable methods. In some instances, the trained algorithm comprises a machine learning algorithm. The machine learning algorithm may be selected from the group consisting of a supervised, semi-supervised and unsupervised learning, such as, for example, a support vector machine (SVM), a Naïve Bayes classification, a random forest, an artificial neural network, a decision tree, a K-means, learning vector quantization (LVQ), self-organizing map (SOM), graphical model, regression algorithm (e.g., linear, logistic, multivariate, association rule learning, deep learning, dimensionality reduction and ensemble selection algorithms. In some embodiments, the machine learning algorithm is selected from the group consisting of: a support vector machine (SVM), a Naïve Bayes classification, a random forest, and an artificial neural network. Machine learning techniques include bagging procedures, boosting procedures, random forest algorithms, and combinations thereof. Illustrative algorithms for analyzing the data include but are not limited to methods that handle large numbers of variables directly such as statistical methods and methods based on machine learning techniques. Statistical methods include penalized logistic regression, prediction analysis of microarrays (PAM), methods based on shrunken centroids, support vector machine analysis, and regularized linear discriminant analysis.

Machine learning algorithms that are useful for image analysis such as image segmentation may include artificial neural networks, specifically convolutional neural networks (CNN). Artificial neural networks mimic networks of neurons based on the neural structure of the brain. They process records one at a time, or in a batch mode, and "learn" by comparing their classification of the case (which can be at the case level or at a pixel level) (which, at the outset, may be largely arbitrary) with the known actual classification of the case. Artificial neural networks are typically organized in layers which comprise an input layer, an output layer, and at least one hidden layer, wherein each layer comprises one or more neurons. Deep learning neural networks tend to include many layers. Each node in a given layer is usually connected to the nodes in the preceding layer and the nodes in the subsequent layer. Typically, a node receives input from the neurons in the preceding layer, changes its internal state (activation) based on the value of the received input, and generates an output based on the input and activation that is then sent towards the node in the subsequent layer. The connections between neurons or nodes are represented by a number (weight) which can be positive (indicative of activating or exciting the subsequent node) or negative (indicative of suppression or inhibition of the subsequent node). A larger weight value indicates a stronger influence the node in a preceding layer has on the node in the subsequent layer. Accordingly, the input propagates through the layers of the neural network to generate a final output.

The input nodes may correspond to selected parameters relevant to the output. In the case of images, the input nodes can correspond to the pixels in the image. In some cases, the errors from the initial output relative the training label are propagated back into the network and are used to modify the network's weights in an iterative process as it is fed training data.

Advantages of neural networks include high noise tolerance and the ability to classify patterns on which they have not been trained.

During training, the neural network typically processes the records in the training data one at a time, using the weights and functions in the hidden layers, then compares the resulting outputs against the desired outputs. Errors are then propagated back through the system, causing the system to adjust the weights for application to the next record to be processed. This process occurs over and over as the weights are continually tweaked. During the training of a network the same set of data may be processed many times as the connection weights are continually refined.

Natural Language Processing

In some cases, the systems, software, and methods disclosed herein apply natural language processing (NLP) algorithm(s) to provide labels for training the computer vision model(s) (e.g., image analysis algorithm/model) and/ or generate reports from model outputs (e.g., reports comprising findings presented in human readable format such as complete sentences). The reporting text can be processed using natural language processing to generate such human readable reports.

Figure 16:
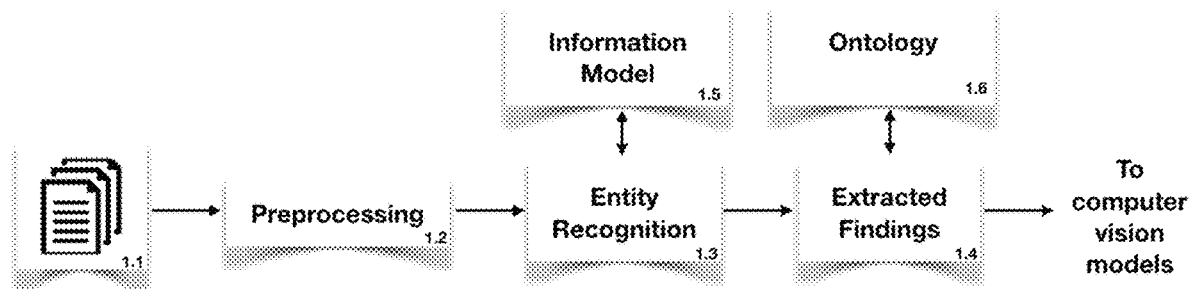
FIG. 16 shows a flow chart illustrating a non-limiting example of a label extraction pipeline.

A non-limiting example of the label extraction pipeline is shown in FIG. 16. This pipeline allows the extraction of structured findings from unstructured text in order to provide training labels for the computer vision models. As shown FIG. 16, radiology report documents (1.1) enter the pipeline. During the preprocessing step (1.2), the reports are split into sections (e.g., Clinical History, Findings, Impressions) using regex pattern matching. In some cases, the pipeline focuses on free-text in the Findings and Impressions sections. This text can be further split into sentences. These extracted findings can be analyzed using the Information Model (1.5) to determine what classes of entities to search for in these sentences, and the Ontology (1.6) for specific instances of classes.

The Information Model can define what types of structured elements will be extracted from free-text. In some cases, the model is based on relevant classes described in published models, including observations (e.g., herniation, edema), anatomy and location (e.g., C2-C3 vertebral disc), certainty (e.g., likely, negated), temporality (e.g., present or past finding), and modifiers such as severity or laterality. The Ontology can represent concepts, their synonyms, their relations (hierarchical or otherwise) and mappings to external databases. It can include dictionaries listing valid examples of Information Model classes such as, for example, all valid observations and their seventies. This Ontology can be based on various publicly available resources such as the RadLex radiology ontology and/or the UMLS and its associated Metamap.

In some cases, regex pattern matching is used to filter for sentences which may contain "frames" of interest; that is, phrases that contain observations and other elements of the Information Model. These filtered sentences can then be tokenized and parsed using natural language processing programs/libraries such as NLTK. The results can be passed to the Stanford NLP Bllip parser, trained on the Genia and PubMed corpuses to generate dependency graphs. This approach allows for retention of syntactic information which can then be leveraged in the Entity Recognition step (1.3) of FIG. 16. This step can leverage pattern matching tied to the Ontology as well rules to extract frames of findings. In some cases, a search is first performed for an observation of interest in the dependency graph. Then Semgrex patterns are used to find dependent modifiers such as severity. Additional logic similar to that of NegEx can be incorporated to ensure that dependencies are within a set span of words from their roots. Sometimes anatomy is not explicitly stated, in which case the Ontology can be leveraged to recover implied location (e.g. "foraminal spinal stenosis" implies the "foramen" as anatomy). In some cases, Semgrex pattern matching is leveraged on dependency graphs along with hard-coded rules to determine certainty/negation.

The results or Extracted Findings (1.4) in FIG. 16 generated following the Entity Recognition step can then be passed to the computer vision training pipeline as full "frames" including as much of the Information Model as can be extracted. Results can be appended to a report database to facilitate search.

Figure 17:
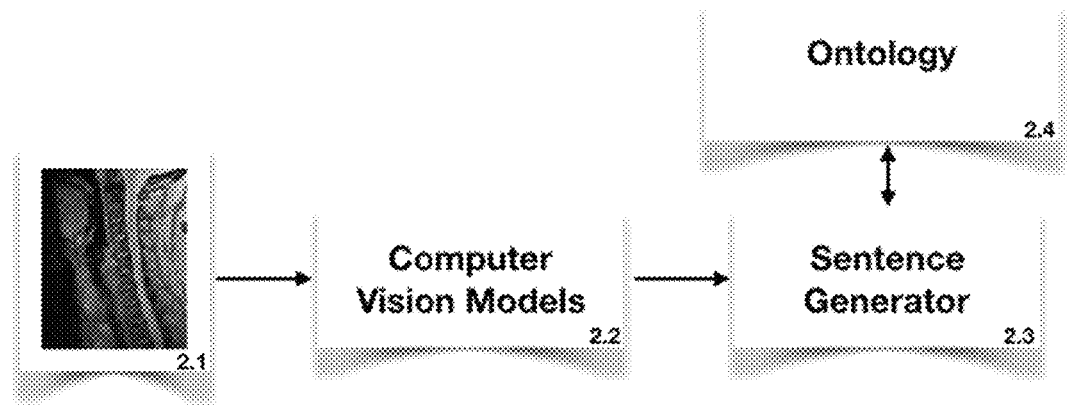
FIG. 17 shows a flow chart illustrating a non-limiting example of an NLP pipeline for generating text from computer vision model outputs.

A non-limiting example of the NLP pipeline for generating text from computer vision model outputs is shown in FIG. 17. Once trained, the computer vision models can accept as input MRI, CT, X-ray or other images and output both the location of findings in the image and their classes according to our Information Model, e.g. "anatomy: left foramen, observation: stenosis, severity: moderate, location: C2-C3." The NLP task at this stage is to construct natural language sentences from these outputs (2.3), e.g. "C2-C3: There is moderate stenosis of the left foramen."

This NLP pipeline can largely comprise a rules-based concatenation process but optionally with added complexity due to idiosyncrasies of different types of findings. For instance, some spine conditions relate to the vertebral body (e.g., endplate change), while others relate to vertebral spans (e.g., lordosis) and must be reported as such. The information embedded in the Ontology can be leveraged to handle such cases. Additionally, the Ontology can contain hierarchical information as well as synonyms, which allows for the aggregation and ordering of findings appropriate for communication to end users.

Computer Vision of Medical Images

Described herein are systems, software, and methods for facilitating AI-assisted interpretation and reporting of medical images. In some cases, the systems, software, and methods comprise identifying/labeling and/or predicting a diagnosis or severity of medical disorders, conditions, or symptoms (e.g., a pathology). As used herein, pathology may be used to refer to a medical disorder, condition, or symptom, for example, a fracture or disc herniation. In some cases, provided herein is the identification and severity prediction of a handful of orthopedic related findings across different anatomies including, but not limited to, the spine, knee, shoulder, and hip. The relevant findings for the given anatomical area can be generated using a system of machine learning algorithms or models for carrying out image analysis (e.g., image segmentation and/or labeling) such as convolutional neural networks. A neural network system can perform image analysis using a process comprising two main phases. The first phase (optional) is a first machine learning algorithm or model such as a first neural network that is responsible for segmenting out the relevant anatomical structures for the given larger anatomy (see, e.g., FIG. 18), which can be referred to as the segmentation step. The second phase is a second machine learning algorithm or model such as a second neural network that is responsible for taking a region of interest in the given anatomy (e.g., a region identified by the first network) and predicting the presence of one or more findings and optionally their relative severity (see, e.g., FIG. 19), which can be referred to as the findings step.

Figure 18:
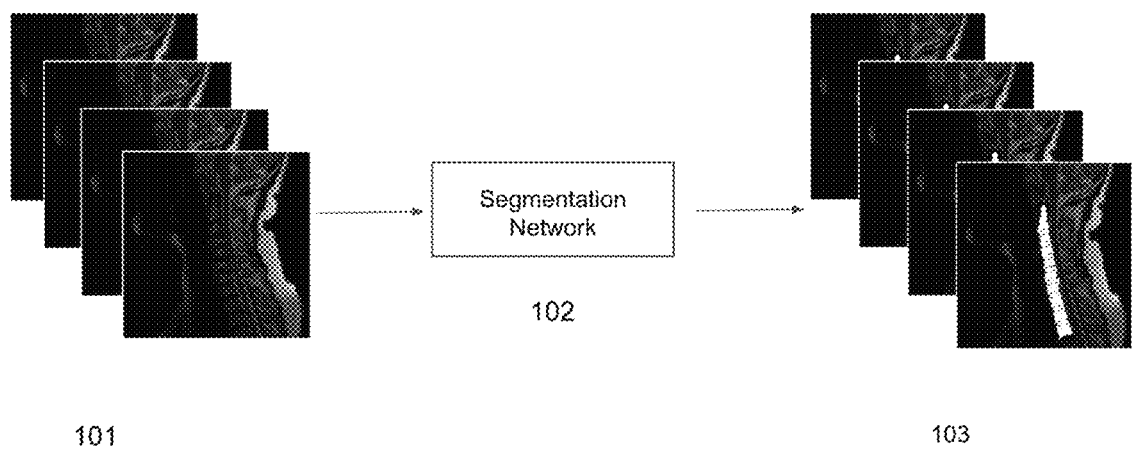
FIG. 18 shows a non-limiting example of a process for image segmentation using a neural network.

FIG. 18 shows an illustrative example of a process for image segmentation using a neural network. For the segmentation step, the neural network intakes a set of images from a given patient (101), that could have been acquired using a number of medical imaging techniques (e.g., magnetic resonance imaging (MRD, computed tomography (CT), and radiographs (X-ray)). MRI images can also come from various sequences such as, for example, T1, T1 with contrast, T2, and T2* (T2-"star"). These imaging scans can be acquired from a number of different viewpoints including axial, sagittal, and coronal orientations. These set of images are then fed into a segmentation neural network (102) that predicts the location of the desired anatomical structures (103). The segmentation neural network can be based on variations of U-Net and Mask-RCNN architectures (103). These networks can be trained on patient images with anatomical structures that were manually annotated by experts.

The predicted segmentation structures can include various anatomic structures. For example, the predicted segmentation structures for spinal scans include but are not limited to: all the vertebral bodies spanning from the first cervical vertebrae all the way to the last sacral vertebrae, all discs in between the vertebral bodies, and all the associated spinous processes. The predicted segmentation structures for knee scans include but are not limited to: the trochlea, medial/lateral anterior/posterior menisci, medial/lateral femoral condyle, medial collateral ligament (MCL), anterior cruciate ligament (ACL), posterior cruciate ligament (LCL), patellar tendon, tibial cartilage, patellar bone, tibial bone, and femoral bone.

Figure 19:
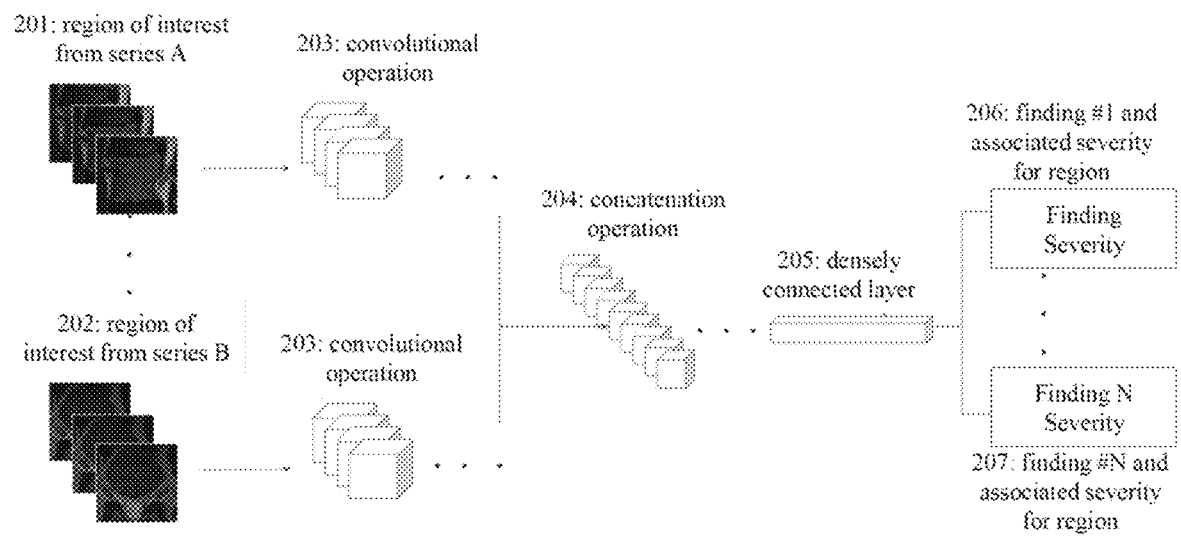
FIG. 19 shows a non-limiting example of a process for generating predictions about one or more anatomic structures in a medical image.

FIG. 19 shows an illustrative process for generating predictions about one or more anatomic structures in a medical image. For the findings step, a set of images from a given patient from at least one imaging type and sequence that represents a region of interest (201) is used as input to the network. Multiple image sets from different sequences or orientations of the same patient can be used as additional inputs (202). This region of interest may be acquired using the segmentations from the segmentation step (see, e.g., FIG. 18) or traditional image pre-processing techniques on the original image (for example cropping around the shoulder joint). Each image set is fed through at least one 2D or 3D convolutional layer (203). A convolutional layer can include a number of regularization steps such as batch normalization, maximum or averaging pooling, and L2 regularization. The output of a convolutional layer can have an activation function applied to it that includes but is not limited to a rectified linear unit (ReLU) or sigmoid function. After at least one convolutional layer operation on a given input image set, if there is more than one input image set, then all input image sets can be concatenated along the channel dimension (204). The concatenated image block can then undergo one or more convolutional layers and one or more densely connected layers (205). A densely connected layer can then be created to predict at least one finding of interest and/or its severity (206). Each additional finding to be predicted may have its own densely connected layer (207). These networks can be trained on the findings information extracted from the associated patient reports using natural language processing (NLP).

Various predicted findings can be generated using the systems, software, and methods disclosed herein. Non-limiting examples of predicted findings such as for spinal cases include but are not limited to: foraminal stenosis, central canal stenosis, disc bulging, disc herniation, disc desiccation, synovial cysts, nerve compression, Schmorl's nodes, vertebrae fractures, and scoliosis across the different vertebral bodies and discs. The predicted findings for knee cases include but are not limited to tears, lesions, and fractures across the various pieces of anatomy described above. The predicted findings for shoulder and hip cases include but are not limited to tears, fractures, and dislocations across the different joints, bones, and ligaments in that anatomical region.

Systems for AI-Assisted Image Interpretation and Medical Report Generation

Described herein are systems, software, and methods for facilitating AI-assisted interpretation and reporting of medical images. In some cases, the systems, software, and methods utilize one or more input components or sensors, e.g., eye-tracking equipment, microphone or audio detection component, and/or other input devices such as mouse, keyword, trackpad, controller, or touchscreen, for obtaining user input and/or dictation. In some instances, the system comprises a display for showing a visualization of one or more medical images and/or reports or associated findings.

In some cases, the display shows an indicator of the user's gaze fixation or selection (e.g., portion of the image the mouse cursor is hovering over).

In some cases, the systems, software, and methods disclosed herein utilize a network element for communicating with a server. In some cases, the server is part of the system. In some cases, the system is configured to upload to and/or download data from the server. In some cases, the server is configured to store sensor data, haptic feedback type(s) and degree(s), and/or other information for the subject. In some cases, the server is configured to store historical data for the subject. In some cases, the server is configured to backup data from the system or apparatus. In some cases, a system as described herein is configured to perform any of the methods described herein.

In some cases, a system as described herein comprises a processor; a hand-held component operatively coupled to the processor; and a non-transitory computer readable storage medium encoded with a computer program configured to communicate with the processor. In some cases, a processor disclosed herein is part of or linked to a computer and includes or is operatively coupled to a display, input device(s), a processor.

In some cases, the system or apparatus is configured to encrypt data. In some cases, data on the server is encrypted. In some cases, the system or apparatus comprises a data storage unit or memory for storing data. In some cases, data encryption is carried out using Advanced Encryption Standard (AES). In some cases, data encryption is carried out using 128-bit, 192-bit, or 256-bit AES encryption. In some cases, data encryption comprises full-disk encryption of the data storage unit (e.g., encrypting the entire hard drive on a server or apparatus). In some cases, data encryption comprises virtual disk encryption (e.g., encrypting a folder containing image data files). In some cases, data encryption comprises file encryption (e.g., encrypting image data files for a subject). In some cases, data that is transmitted or otherwise communicated between the system or apparatus and other devices or servers is encrypted during transit. In some cases, wireless communications between the system or apparatus and other devices or servers is encrypted, e.g., using a Secure Sockets Layer (SSL). In some cases, access to data stored on the system or apparatus as described herein requires user authentication. In some cases, access to data stored on the server as described herein requires user authentication.

An apparatus as described herein comprises a digital processing device that includes one or more hardware central processing units (CPUs) and possibly one or more general purpose graphics processing units (GPGPUs) or tensor processing units (TPUs) that carry out specific computations. The digital processing device further comprises an operating system configured to perform executable instructions. The digital processing device is optionally connected to a computer network. The digital processing device is optionally connected to the Internet such that it accesses the World Wide Web. The digital processing device is optionally connected to a cloud computing infrastructure. Suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein.

Typically, a digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some cases, the operating system is provided by cloud computing including non-limiting examples such as Amazon Web Services (AWS), Google Cloud Platform (GCP), or Microsoft Azure.

A digital processing device as described herein either includes or is operatively coupled to a storage and/or memory device. The storage and/or memory device is one or more physical apparatuses used to store data or programs on a temporary or permanent basis. In some cases, the device is volatile memory and requires power to maintain stored information. In some cases, the device is non-volatile memory and retains stored information when the digital processing device is not powered. In further cases, the non-volatile memory comprises flash memory. In some cases, the non-volatile memory comprises dynamic random-access memory (DRAM). In some cases, the non-volatile memory comprises ferroelectric random access memory (FRAM). In some cases, the non-volatile memory comprises phase-change random access memory (PRAM). In other cases, the device is a storage device including, by way of non-limiting examples, CD-ROMs, DVDs, solid-state drives, magnetic disk drives, magnetic tapes drives, optical disk drives, and cloud computing based storage. In further cases, the storage and/or memory device is a combination of devices such as those disclosed herein.

Some embodiments of the systems described herein are computer based systems. These embodiments include a CPU including a processor and memory which may be in the form of a non-transitory computer-readable storage medium. These system embodiments further include software that is typically stored in memory (such as in the form of a non-transitory computer-readable storage medium) where the software is configured to cause the processor to carry out a function. Software embodiments incorporated into the systems described herein contain one or more modules.

In various cases, an apparatus comprises a computing device or component such as a digital processing device. In some of the embodiments described herein, a digital processing device includes a display to send visual information to a user. Non-limiting examples of displays suitable for use with the systems and methods described herein include a liquid crystal display (LCD), a thin film transistor liquid crystal display (TFT-LCD), an organic light emitting diode (OLED) display, an OLED display, an active-matrix OLED (AMOLED) display, or a plasma display.

A digital processing device, in some of the embodiments described herein includes an input device to receive information from a user. Non-limiting examples of input devices suitable for use with the systems and methods described herein include a keyboard, a mouse, trackball, track pad, stylus, microphone, gesture recognition device, eye tracking device, or camera. In some embodiments, the input device is a touch screen or a multi-touch screen.

The systems and methods described herein typically include one or more non-transitory computer-readable storage media encoded with a program including instructions executable by the operating system of an optionally networked digital processing device. In some embodiments of the systems and methods described herein, the non-transitory storage medium is a component of a digital processing device that is a component of a system or is utilized in a method. In still further embodiments, a computer-readable storage medium is optionally removable from a digital processing device. In some embodiments, a computer-readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Typically the systems and methods described herein include at least one computer program or use of the same. A computer program includes a sequence of instructions, executable in the digital processing device's CPU, written to perform a specified task. Computer-readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages. The functionality of the computer-readable instructions may be combined or distributed as desired in various environments. In some cases, a computer program comprises one sequence of instructions. In some cases, a computer program comprises a plurality of sequences of instructions. In some cases, a computer program is provided from one location. In other cases, a computer program is provided from a plurality of locations. In some cases, a computer program includes one or more software modules. In some cases, a computer program includes, in part or in whole, one or more web applications, one or more mobile applications, one or more standalone applications, one or more web browser plug-ins, extensions, add-ins, or add-ons, or combinations thereof. In some cases, a software module comprises a file, a section of code, a programming object, a programming structure, or combinations thereof. In some cases, a software module comprises a plurality of files, a plurality of sections of code, a plurality of programming objects, a plurality of programming structures, or combinations thereof. In some cases, the one or more software modules comprise, by way of non-limiting examples, a web application, a mobile application, and a standalone application. In some cases, software modules are in one computer program or application. In other cases, software modules are in more than one computer program or application. In some cases, software modules are hosted on one machine. In other cases, software modules are hosted on more than one machine. In further cases, software modules are hosted on cloud computing platforms. In some cases, software modules are hosted on one or more machines in one location. In other cases, software modules are hosted on one or more machines in more than one location.

Typically, the systems and methods described herein include and/or utilize one or more databases. In view of the disclosure provided herein, those of skill in the art will recognize that many databases are suitable for storage and retrieval of baseline datasets, files, file systems, objects, systems of objects, as well as data structures and other types of information described herein. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some cases, a database is internet-based. In some cases, a database is web-based. In some cases, a database is cloud computing-based. In other cases, a database is based on one or more local computer storage devices.

The systems and methods described herein may include one or more controlled terminologies or lexicons to describe biomedical concepts. One skilled in the arts will recognize that numerous formats may be suitable including web ontology language (OWL) or Resource Description Framework (RDF) and that queries may be made using a query language such as SPARQL. Relevant ontologies and related resources include non-limiting examples such as RadLex, the Foundational Model of Anatomy (FMA), SNOMED Clinical Terms, or the UMLS Metathesaurus.

Figure 15:
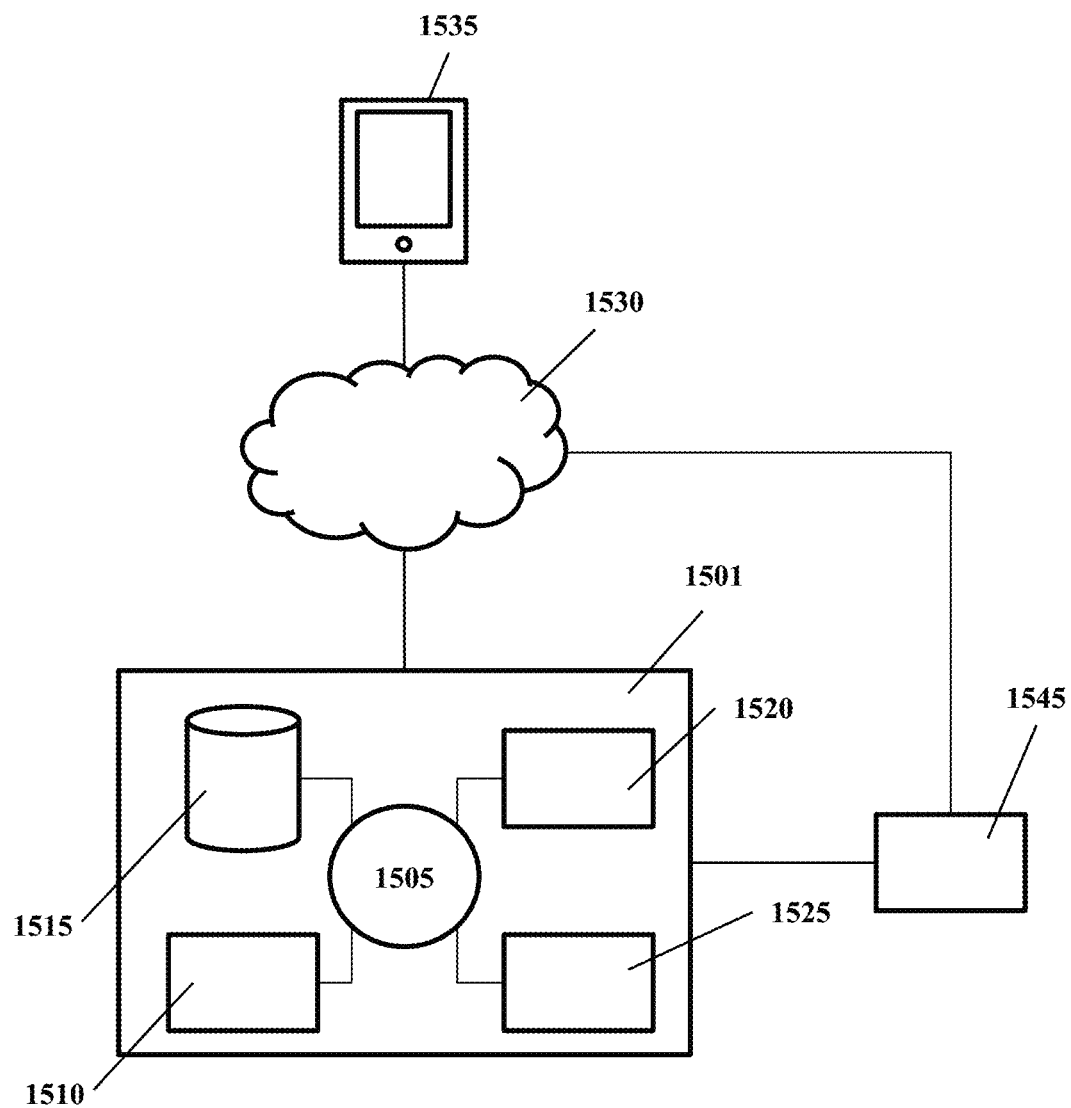
FIG. 15 shows a non-limiting embodiment of a computer system for carrying out any of the processes or methods as described herein.

FIG. 15 shows exemplary embodiments of a system as described herein comprising an apparatus such as a digital processing device 1501. The digital processing device 1501 includes a software application configured to determine a type and degree of haptic feedback to a user. The digital processing device 1501 may include a central processing unit (CPU, also "processor" and "computer processor" herein) 1505, which can be a single core or multi-core processor, or a plurality of processors for parallel processing. The digital processing device 1501 also includes either memory or a memory location 1510 (e.g., random-access memory, read-only memory, flash memory), electronic storage unit 1515 (e.g., hard disk), communication interface 1520 (e.g., network adapter, network interface) for communicating with one or more other systems, and peripheral devices, such as cache. The peripheral devices can include storage device(s) or storage medium 1565 which communicate with the rest of the device via a storage interface 1570. The memory 1510, storage unit 1515, interface 1520 and peripheral devices are configured to communicate with the CPU 1505 through a communication bus 1525, such as a motherboard. The digital processing device 1501 can be operatively coupled to a computer network ("network") 1530 with the aid of the communication interface 1520. The network 1530 can comprise the Internet. The network 1530 can be a telecommunication and/or data network.

The digital processing device 1501 includes input device(s) 1545 to receive information from a user, the input device(s) in communication with other elements of the device via an input interface 1550. The digital processing device 1501 can include output device(s) 1555 that communicates to other elements of the device via an output interface 1560.

The CPU 1505 is configured to execute machine-readable instructions embodied in a software application or module. The instructions may be stored in a memory location, such as the memory 1510. The memory 1510 may include various components (e.g., machine readable media) including, but not limited to, a random access memory component (e.g., RAM) (e.g., a static RAM "SRAM", a dynamic RAM "DRAM, etc.), or a read-only component (e.g., ROM). The memory 1510 can also include a basic input/output system (BIOS), including basic routines that help to transfer information between elements within the digital processing device, such as during device start-up, may be stored in the memory 1510.

The storage unit 1515 can be configured to store files, such as health or risk parameter data, e.g., individual health or risk parameter values, health or risk parameter value maps, and value groups. The storage unit 1515 can also be used to store operating system, application programs, and the like. Optionally, storage unit 1515 may be removably interfaced with the digital processing device (e.g., via an external port connector (not shown)) and/or via a storage unit interface. Software may reside, completely or partially, within a computer-readable storage medium within or outside of the storage unit 1515. In another example, software may reside, completely or partially, within processor(s) 1505.

Information and data can be displayed to a user through a display 1535. The display is connected to the bus 1525 via an interface 1540, and transport of data between the display other elements of the device 1501 can be controlled via the interface 1540.

Methods as described herein can be implemented by way of machine (e.g., computer processor) executable code stored on an electronic storage location of the digital processing device 1501, such as, for example, on the memory 1510 or electronic storage unit 1515. The machine executable or machine readable code can be provided in the form of a software application or software module. During use, the code can be executed by the processor 1505. In some cases, the code can be retrieved from the storage unit 1515 and stored on the memory 1510 for ready access by the processor 1505. In some situations, the electronic storage unit 1515 can be precluded, and machine-executable instructions are stored on memory 1510.

In some embodiments, a remote device 1502 is configured to communicate with the digital processing device 1501, and may comprise any mobile computing device, non-limiting examples of which include a tablet computer, laptop computer, smartphone, or smartwatch. For example, in some embodiments, the remote device 1502 is a smartphone of the user that is configured to receive information from the digital processing device 1501 of the apparatus or system described herein in which the information can include a summary, sensor data, types and degrees of haptic feedback, or other data. In some embodiments, the remote device 1502 is a server on the network configured to send and/or receive data from the apparatus or system described herein.

Certain Definitions

As used herein, the singular forms "a", "an" and "the" include plural references unless the context clearly dictates otherwise. For example, the term "a sample" includes a plurality of samples, including mixtures thereof. Any reference to "or" herein is intended to encompass "and/or" unless otherwise stated.

As used herein, the phrases "at least one of a, b, c, and d" and "at least one of a, b, c, or d" refer to a, b, c, or d, and any and all combinations comprising two or more than two of a, b, c, and d.

As used herein, the term "artificial intelligence" or "AI" refers to any computer-assistance algorithm including, for example, machine learning algorithms such as a neural network or a support vector machine.

As used herein, the term "machine learning" or "machine learning algorithm" refers to algorithms and/or models or classifiers that are used by computer systems to perform a task without explicit instructions. For example, the tasks can be carried out using models/classifiers that have been trained with a relevant data set to make predictions or inferences of outcomes or categorizations when presented with new data.

As used herein, the terms "radiology" and "radiologist" are used as representative of the larger area of medical imaging. Non-limiting examples that are encompassed by these terms include the many possible medical subspecialties and clinicians that handle medical images (e.g., radiology, nuclear medicine, pathology, cardiology, OB/GYN, emergency medicine, etc.).

As used herein, the term "healthcare provider" or "healthcare practitioner" are used as representatives of any person or entity that provides healthcare or healthcare-related products and/or services. Non-limiting examples that are encompassed by these terms include the many healthcare or medicine related workers such as radiologists, radiologic technicians, surgeons, family doctors, internal medicine physicians, pediatricians, obstetrician/gynecologists, dermatologists, infectious disease physicians, nephrologists, ophthalmologists, pulmonologists, neurologists, anesthesiologists, oncologists, nurses, nursing assistants, medical assistants, clinical laboratory technicians, and physical therapists.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1—Image Segmentation

Image segmentation is performed on an image of the spine. Input images to the segmentation module are MRI T2-weighted sagittal images of the spine. Image segmentation is performed to distinguish between the following four classes: vertebra, intervertebral disc, spinal cord, and background. At this stage, all the visible vertebrae are segmented as a single class and all of the visible discs are segmented as a single class with no attempt to distinguish between individual vertebrae (e.g., L1 vs L2 vs L3, etc.; see FIG. 22). Image segmentation is performed using a 2.5D fully convolutional network (FCN) using cross entropy loss with an Adam optimizer (Long J et al., arXiv 2015). The images are resized and intensity normalized. Hyperparameter search is performed via a grid search. Regularizations include early stopping criteria, batch normalization, and dropout. A single FCN model is used for segmentation of cervical, thoracic, and lumbar spine imaging studies. As shown in FIG. 22, the anatomic navigator shows spine segmentation with the original source images shown on left and computed segmentation shown on right with vertebral bodies in yellow and intervertebral discs in blue.

Example 2—Image Labeling

Image region labeling subdivides the region representing all vertebrae into individual vertebrae (C1 through S1) and the region representing all intervertebral discs into individual discs (C1-C2 through L5-S1), as shown in FIG. 23. It also places points corresponding to left/right foramen and left/right facet joints at each intervertebral disc level. For lumbar studies, a single point is placed at the conus medullaris. The user may turn on or off visualization any of these regions/points and/or text labels if so desired. Also, the entire spine model with labels may also be visualized in 3D. Vertebra and disc labeling is performed using a 2.5D DeepLab v3 neural network using cross entropy loss with an Adam optimizer (Chen L C et al., IEEE PAMI 2018). Images are resized and intensity normalized. Hyperparameter search is performed via a grid search. Regularizations include early stopping criteria, batch normalization, and dropout. Landmark detection of left/right foramen, left/right facet joints, and conus are performed using a Convolutional Pose Machine (CPM), which combines the long-range image sequence advantages of pose machines with the feature detection and spatial context awareness advantages of convolutional neural networks (Wei S E et al., arXiv 2016). These networks are evaluated through Euclidean distance metrics and Percentage Correct Keypoint (PCK) metrics.

Example 3—User Check Step

Figure 24:
FIG. 24 shows an illustrative example of an anatomic navigator-enabled image providing a user with the option to confirm accuracy of segmentation and labeling, reject, or edit segmentation and labeling.

A process is provided for the user to doublecheck the labeled regions and take one of three actions: accept, reject, or edit (see FIG. 24). If user accepts the results, the labeled regions are then used to translate 3D coordinates into anatomic descriptors as described below. If user rejects results, then no anatomic descriptors are provided to the reporter and the reporter falls back to basic interactions where the user clicks on template regions in the reporter window or uses the forward and backward keys on the dictaphone. If the user selects edit, they may edit the pixels included in each region (segmentation editing) and/or the labels for each region (label editing). For segmentation editing, a set of editing tools are provided including a paintbrush to add or remove pixels and erosion/dilation tools. For label editing, the user may click on the label and choose a new label either by voice or by a contextual dropdown menu.

Example 4—Anatomic Mapper

For the various modes of navigation described herein, the anatomic mapper module takes as input the labeled image regions accepted by the user as described in example 3. In one mode of interaction, the user clicks on the image and the 3D coordinates (in DICOM Reference Coordinates System within a given DICOM Frame of Reference) are mapped to an anatomic descriptor by a direct pixel lookup in the labeled segmentation map. The reporter text input cursor is simply placed in the field corresponding to that descriptor. If the result is a background label, the catch-all "Additional Information:" template field is selected.

In another mode of navigation, the user selects a report template field and the anatomic descriptor for that field is converted into a padded bounding box as follows. A tight bounding box for that pixel label in the labeled segmentation map is computed as the min/max x-y-z bounds and, in order to provide the context of surrounding anatomy, an extra 50% padding is added to the bounding box in all directions. When the image viewports are scrolled, panned, and zoomed to fit this bounding box, first, each image viewport is scrolled and panned so that the bounding box center is at the center of the image viewport. The maximum zoom is set that fully includes each padded bounding box in each image viewport.

In order to reduce the amount of "look away" back to the reporter window, visual feedback of the anatomic descriptor is provided in real time. As the mouse is moved across an image viewport, anatomic descriptors are looked up and the corresponding text is displayed as an annotation in the image viewport. Additionally, the geometry of the labeled region is displayed with a translucent colored boundary.

For another mode of interaction, the anatomic descriptor is provided by speech-to-text. As in the other two modes of interaction, the corresponding template field is selected, the image viewports are scrolled, panned, and zoomed appropriately, and visual feedback of the image region is provided.

Example 5—Algorithm Development

A dataset of imaging data is acquired and de-identified for generating the algorithm/model. For this dataset, acquisition is sequential with training and validation sets coming from the initial 1600 studies and the test set coming from the final 400 studies. Training and validations sets are sourced from different image centers with a different mix of scanner models and manufacturers in order to demonstrate external validity.

Two thousand spine MRI studies of adults were selected from typical workflow and fully de-identified. The split between training, validation, and test sets is 50%/30%/20%. Standard data augmentations are used including translation, rotation, cropping, and shearing. Data annotations on 2000 imaging studies have been performed by a team of annotators, all with prior medical image annotation experience. Annotations are provided in the form of a set of 2D contours for each individual vertebra and each intervertebral disc.

Labels for the specific vertebrae and discs are also provided by the annotators. For cervical spine, they begin labeling starting from C2 and going inferiorly. For lumbar spine, labeling starts from S1 and proceeds superiorly. For thoracic spine, there is not an obvious anchor vertebra so the sagittal localizer image that has the entire spine in the field of view is used, in which point annotations are added starting from C2 and going inferiorly. Annotation of the spinal cord is performed using an intensity-based 3D region-filling tool. Pointwise annotations of foramen, facet joints and the conus are performed using a pointwise labeling image annotation tool.

Example 6—Algorithm Testing

Bench testing is carried out on the segmentation and labeling algorithms of the anatomic navigator module. Firstly, the segmentation accuracy for each class of volumetric segmented structure (vertebrae, discs, spinal cord) is tested. The reference standard segmentations is performed by two board-certified musculoskeletal radiologists or neuroradiologists. For the spinal cord and each individual vertebra and disc, if the Dice score between the two radiologists is lower than 0.8, a third senior MSK or neuroradiologist will either select the more accurate segmentation or annotate their own if neither is acceptable. If the Dice score is greater than or equal between to 0.8, the union of the two will be used to determine a single reference standard region.

For pointwise landmarks, if the distance between landmark points is greater than 8 mm for the two radiologists, the points is similarly adjudicated. Otherwise, the centroid of the two radiologists' points will be used as the single reference standard. Segmentation accuracy for each class of regions (all vertebrae, all discs, spinal cord) are reported as an overall Dice score, per-pixel sensitivity, and per-pixel specificity.

Secondly, the labeling accuracy is tested for each of the repeating structures including vertebrae, discs, foramen, and facet joints. For labeling accuracy on repeating structures, we aim to detect cases of "off by one or more" levels. A segmented volumetric structure is considered to have the correct label if it has a Dice score of greater than or equal to 0.5 with the reference standard individually labeled structure. Pointwise structures are considered to be correctly labeled if within 8 mm of the reference standard defined above. Labeling accuracy is reported as overall percentage accuracy. Sub-analyses will be performed breaking down the dataset by spinal region (cervical/thoracic/lumbar), patient gender and age, scanner field strength, scanner manufacturer and model, and pulse sequence parameter (TE/TR/TI), and image pixel spacing.

Example 7—AI-Assisted Dictation of Findings

A user turns on his radiology image analysis workstation and accesses the software for AI-assisted image analysis. The user selects a radiological image from a workflow in the software. The user points at and uses the computer mouse to click on a specific part of the anatomy in the radiological image, which then sets the anatomic context for the software. The software uses this anatomic context in order to keep the images being displayed in synchronization with the report text, which may use templates to support structuring the text.

Each piece of anatomy in the system has a tag which describes the type of anatomy. This is a unique identifier for each type of anatomy in the software's ontology. This identifier is what is used to set the anatomic context globally such that all other user actions occur in this context. The tags are generated using the image segmentation and labeling techniques disclosed herein.

The user is then presented with a list possible clinical findings relevant to that part of the anatomy. In this case, the list of findings is generated by a computer aided detection/diagnosis module that creates a list of possible findings at that particular region of the image where the inference is specific to this particular patient. A score or probability is given for each possible finding and the findings are presented in decreasing order. These possible findings are generated using an image analysis algorithm that includes a module or classifier that identifies possible pathologies or features in the anatomy shown in the image.

When the user selects a particular finding from the list, a structured representation of the finding is generated. This finding is represented through a knowledge graph that represents various concepts including the anatomic location and the type of observation. For each concept, one or more modifiers are associated with it including sub-anatomic location and severity of the observation.

Finally, the structured representation of the imaging finding is then converted into natural text for insertion into the report. This natural text representation is created through a query into a database of previous imaging findings and their structured representation as a knowledge graph. In addition, the natural text representation can also be created through a simple set of production rules given the structure of the knowledge graph.

Example 8—Mapping of User Inputs and Anatomic Context to Preexisting Sentences

User input is obtained as described in example 7, for example, through menu selections or dictation. The user inputs are then matched to pre-written sentences stored in a database.

In the case of voice-driven user inputs (e.g., user dictation), a simple keyword match is performed with heuristics. Sentences are matched using keywords users dictate, or synonyms thereof using word embeddings. Heuristics are also applied, for example, taking word order into account and returning sentences with the highest ratio of matching tokens to total tokens.

Alternatively, for voice-driven user inputs, a keyword match with inference (instead of heuristics) can be performed. In this case, a layer of inference is introduced that maps from keywords to formulas for findings and leverages those mappings, along with anatomic context, to limit the number of findings users could mean. These findings formulas contain all the variables that go into a valid finding. Values for these variables are defined in the ontology. The formula for a "foraminal spinal stenosis" finding includes variables for disc level, laterality and severity. The formula for "canal stenosis" finding includes only disc level and severity. When a user dictates "bilateral" and "stenosis", it is inferred that they likely mean "foraminal spinal stenosis" rather than "canal stenosis". Accordingly, this approach promotes efficiency by preventing the user from having to say two words ("foraminal spinal"), along with disc level, which is obtained from the anatomic navigator context. This approach relies on having previously mapped existing sentences to their canonical meaning. This can be done using whole NLP parsing/mini-graph representation. When the user inputs are menu-driven instead of voice-driven, menu selections by the user can allow a mini-graph to be matched to preexisting and pre-parsed sentences.

Example 9—Auto-Measurement Function

User input can be obtained as described in Example 7 and utilized for an automatic measurement function, which can be provided alone or in combination with the AI-assisted dictation of findings. In the semi-manual version of the auto-measure tool, as soon as the measurement tool is activated, a magnified version of the image near the mouse pointer is overlaid on the non-magnified image and the mouse movements in manipulating the ruler endpoints is done in the magnified image in order to avoid the problem described above. Additionally, assistance is provided to ensure that the ruler endpoint is placed as close to images in the image as possible. This is accomplished by computing an edge potential map of the image, I (see FIG. 28A). The image gradient is computed using convolution with derivative of Gaussian kernels, G, as used in the well-known Canny edge detector (Canny, IEEE TPAMI 1986). The edge potential map, g, is computed using any function that varies inversely with image gradient magnitude such as the formula in FIG. 28B.

From the original position of the placed ruler endpoint, the desired endpoints are computed by performing a line search along the line defined by the two ruler endpoints. The edge potential map is used to allow the ruler endpoints to fall into the local minimum, at which point they become the desired endpoints. Thus, as long as the ruler endpoints are initially placed close to an image edge, they will automatically find the edge and stick to it.

In the fully automated version of the auto-measure tool, the user defines a single point on the image (e.g., using a mouse click or eye tracking) to initiate the tool. Linear measurements are made at numerous angles and the user chooses either the single longest for a 1D measurement, or the longest measurement and the measurement(s) perpendicular to it for a 2D or 3D measurement.

From the initially placed point near the center of the object, a star shaped pattern is used to perform directional line searches at various angles (e.g., every 45 degrees). Each search is terminated when a local minimum of sufficient depth (e.g., <50% of the edge potential at the initial point) is reached.

For both the semi-manual and the fully automated measurement methods, the user is able to adjust the measurement in an automated fashion by either using voice input to increase/decrease the desired endpoints (saying "larger" or "smaller") or by using the mouse scroll wheel.

Example 10—Comparative Case Flow

User input can be obtained as described in Example 7 and utilized for comparative case flow, which can be provided alone or in combination with the AI-assisted dictation of findings. For example, the AI-assisted dictation of findings described in Example 7 can incorporate a comparative case flow function that utilizes the described anatomic segmentation and labeling functions. When comparing image stacks such as the current and prior image stacks, the segmentation and labeling of the relevant anatomy will have already been computed. Compared to the general case of 3D to 3D image registration, a simplifying assumption is made such that the registration is 1D where given an image in one image stack, the nearest matching image in the other image stack is desired without full 3D rotation.

The current image in the fixed image stack is selected by the user and the comparative case flow process finds the image in the moving image stack that is closest in matching the anatomy of the fixed image. In order to consider this as a 1D problem, centroid of each 3D anatomic labeled region is computed and then projected onto the line perpendicular to the image stack. This is done for both fixed and moving image stacks. The distances between matching pairs of anatomic regions, d, are computed and their squared sum, D, is computed as shown in FIG. 29A. This sum is minimized in order to find the optimal 1D translation between the fixed image and the moving image as shown in FIG. 29B in which four anatomic region centroids (circles) are computed and projected onto the lines perpendicular to each image stack (thin horizontal lines) for both fixed (above) and moving (below) image stacks. The pairwise distances are shown in thick horizontal lines.

Example 11—Image Query Function

User input can be obtained as described in Example 7 and utilized for an image query function, which can be provided alone or in combination with the AI-assisted dictation of findings. A deep convolutional neural network is generated for each of 50 different abnormalities for spine MRI images. Each network is trained on a data set of at least 5,000 segmented MRI images with appropriate labels for the specific abnormality. Each network is configured to output a numerical value that corresponds to severity of the abnormality (normalized to between 0 and 1). The numerical value is divided into categories of severity of the abnormality (0-0.2 low, 0.2<to 0.7 moderate, 0.7<to 1 severe).

The image is pre-evaluated using the trained neural networks before the user begins evaluating the image, evaluated once the user begins evaluating the image, or evaluated after the user selects a portion of the image and initiates the query. For example, when the user is evaluating the image such as during the AI-assisted findings process in Example 7, the user initiates a query using either a designated mouse button, a keyboard hotkey, or by voice command ("What's this?"). At the time of query, the image position is defined either using the mouse or by other computer input devices such as an eye-tracking device.

If a candidate lesion (abnormality) identified by the trained neural networks is close enough to the designated image location and has a probability or score above a given threshold, the query will present this result to the user and form a full text sentence describing this finding. The user will then be prompted to either accept or reject the sentence into the findings section of the medical report.

What is claimed is:

1. A computer based system for medical report generation, comprising:
   (a) a processor;
   (b) a display configured to show a graphical user interface for evaluating a medical image;
   (c) a non-transitory computer readable storage medium encoded with a computer program that causes said processor to:
      (i) analyze a medical image with an artificial intelligence-assisted image segmentation algorithm to label a plurality of image features;
      (ii) generate a result comprising a computer-generated finding comprising a diagnosis and an anatomic variant, wherein said result is based on said medical image and said plurality of image features; and
      (ii) generate a medical report including said computer-generated finding when a user accepts inclusion of said computer-generated finding within said medical report.

2. The system of claim 1, wherein the image segmentation algorithm partitions said medical image into multiple pixel segments corresponding to the plurality of image features.

3. The system of claim 2, wherein said plurality of image features are organized in a hierarchy.

4. The system of claim 1, wherein each of said plurality of image features corresponds to an anatomical structure, a tissue type, a tumor or tissue abnormality, a contrast agent, or any combination thereof.

5. The system of claim 4, wherein said plurality of image features comprises one or more of nerve, blood vessel, lymphatic vessel, organ, joint, bone, muscle, cartilage, lymph, blood, adipose, ligament, or tendon.

6. The system of claim 1, wherein said medical report comprises one or more sentences or phrases describing or assessing at least one feature of said plurality of image features.

7. The system of claim 1, wherein said system further comprises an audio detection component configured to detect or record an input that indicates when said user accepts inclusion of said computer-generated finding.

8. The system of claim 1, wherein said medical image is a radiographic image, a magnetic resonance imaging (MM) image, an ultrasound image, an endoscopy image, an elastography image, a thermogram image, a positron emission tomography (PET) image, a single photon emission computed tomography (SPECT) image, an optical coherence tomography (OCT) image, a computed tomography (CT) image, a microscopy image, or a medical photography image.

9. The system of claim 1, wherein said computer program is configured to cause said processor to analyze said medical image using a machine learning classifier algorithm, thereby generating said result comprising said computer-generated finding.

10. The system of claim 9, wherein said computer-generated finding comprises an identification or evaluation of a pathology.

11. The system of claim 10, wherein said identification or evaluation of said pathology comprises at least one of a severity, quantity, measurement, presence, or absence of said pathology or a sign or symptom thereof.

12. The system of claim 10, wherein said computer-generated finding is included in said medical report when said computer-generated finding comprises a positive identification or said pathology.

13. The system of claim 1, wherein said system uses a cloud-based server or network to perform at least one of analysis of said medical image and generation of said medical report.

14. The system of claim 1, wherein said processor is configured to provide a worklist management interface allowing said user to reserve one or more cases comprising one or more images from a plurality of cases available for review.

15. The system of claim 1, wherein said processor is configured to determine congruence between said computer-generated finding and a user-finding included in said medical report.

16. The system of claim 1, wherein said processor is configured to automatically populate a portion of said medical report based on a determination of congruence between at least one feature of said plurality of features and an input from said user.

17. The system of claim 15, wherein said processor is configured to present said computer-generated finding to said user for acceptance and optionally editing, wherein an accepted computer-generated finding is automatically populated into said portion of said medical report.

18. The system of claim 17, wherein said computer-generated finding comprises a full text sentence.

19. The system of claim 1, wherein said medical report comprises a radiology report.

* * * * *

UNITED STATES PATENT AND TRADEMARK OFFICE
CERTIFICATE OF CORRECTION

Page 1 of 1

PATENT NO. : 11,894,114 B2
APPLICATION NO. : 17/143808
DATED : February 6, 2024
INVENTOR(S) : David Seungwon Paik et al.

It is certified that error appears in the above-identified patent and that said Letters Patent is hereby corrected as shown below:

In the Claims

Claim 1 Column 66, Line 37, delete "(ii) generate a medical report including said computer-" and insert --(iii) generate a medical report including said computer- -- therefor.

Signed and Sealed this
Fifth Day of March, 2024

Katherine Kelly Vidal
*Director of the United States Patent and Trademark Office*